US012056607B2

(12) United States Patent
Heifets et al.

(10) Patent No.: US 12,056,607 B2
(45) Date of Patent: *Aug. 6, 2024

(54) SYSTEMS AND METHODS FOR CORRECTING ERROR IN A FIRST CLASSIFIER BY EVALUATING CLASSIFIER OUTPUT IN PARALLEL

(71) Applicant: Atomwise Inc., San Francisco, CA (US)

(72) Inventors: Abraham Samuel Heifets, San Francisco, CA (US); Izhar Wallach, Albany, CA (US); Kong Thong Nguyen, San Jose, CA (US)

(73) Assignee: ATOMWISE INC., San Francisco, CA (US)

( * ) Notice: Subject to any disclaimer, the term of this patent is extended or adjusted under 35 U.S.C. 154(b) by 1179 days.

This patent is subject to a terminal disclaimer.

(21) Appl. No.: 16/746,692

(22) Filed: Jan. 17, 2020

(65) Prior Publication Data

US 2020/0334528 A1 Oct. 22, 2020

Related U.S. Application Data

(63) Continuation of application No. 15/473,980, filed on Mar. 30, 2017, now Pat. No. 10,546,237.

(51) Int. Cl.
*G06N 3/08* (2023.01)
*G06F 18/00* (2023.01)
(Continued)

(52) U.S. Cl.
CPC .............. *G06N 3/08* (2013.01); *G06F 18/00* (2023.01); *G06F 18/214* (2023.01);
(Continued)

(58) Field of Classification Search
None
See application file for complete search history.

(56) References Cited

U.S. PATENT DOCUMENTS

| 5,048,100 A | 9/1991 | Kuperstein |
|---|---|---|
| 5,491,627 A | 2/1996 | Zhang et al. |

(Continued)

FOREIGN PATENT DOCUMENTS

| CN | 102930181 A | 2/2013 |
|---|---|---|
| JP | 2009-007302 A | 1/2009 |

(Continued)

OTHER PUBLICATIONS

Khan, et al., One-Class Classification: Taxonomy of Study and Review of Techniques, The Knowledge Engineering Review, (2014) pp. 1-30 (Year: 2014).*

(Continued)

*Primary Examiner* — Wilbert L Starks

(57) ABSTRACT

Systems and methods for classifying a test object are provided. For each respective target object in a plurality of target objects, a first procedure is performed comprising (a) posing the test object against the respective target thereby obtaining an interaction between the test and target, and (b) scoring the interaction with a first classifier. Each such score across the plurality of targets forms a test vector that is inputted into a second classifier thereby obtaining an indication of a target object. The second classifier is trained on training vectors, each being the output from instances of the first classifier after inputting a corresponding training object in a plurality of training objects in accordance with the first procedure. Each object in one subset of the training objects is uniquely associated with one of the targets. Another subset of the training objects is not associated with the targets.

20 Claims, 18 Drawing Sheets

(51) Int. Cl.
| | |
|---|---|
| G06F 18/214 | (2023.01) |
| G06F 18/2413 | (2023.01) |
| G06N 3/04 | (2023.01) |
| G06N 3/045 | (2023.01) |
| G06N 5/04 | (2023.01) |
| G06V 10/774 | (2022.01) |
| G16B 40/00 | (2019.01) |
| G16C 20/30 | (2019.01) |
| G16C 20/70 | (2019.01) |
| G06N 3/126 | (2023.01) |
| G06N 5/01 | (2023.01) |
| G06N 7/01 | (2023.01) |
| G06N 20/10 | (2019.01) |
| G16B 35/20 | (2019.01) |
| G16C 20/64 | (2019.01) |

(52) U.S. Cl.
CPC ........... G06F 18/2413 (2023.01); G06N 3/04 (2013.01); G06N 3/045 (2023.01); G06N 5/04 (2013.01); G06V 10/774 (2022.01); G16B 40/00 (2019.02); G16C 20/30 (2019.02); G16C 20/70 (2019.02); G06N 3/126 (2013.01); G06N 5/01 (2023.01); G06N 7/01 (2023.01); G06N 20/10 (2019.01); G16B 35/20 (2019.02); G16C 20/64 (2019.02)

(56) References Cited

U.S. PATENT DOCUMENTS

| | | |
|---|---|---|
| 7,747,070 B2 | 6/2010 | Puri |
| 9,190,053 B2 | 11/2015 | Penn et al. |
| 9,202,144 B2 | 12/2015 | Wang et al. |
| 9,373,059 B1 | 6/2016 | Heifets et al. |
| 9,965,719 B2 | 5/2018 | Choi |
| 10,002,312 B2 | 6/2018 | Heifets et al. |
| 10,235,771 B2 | 3/2019 | Rad |
| 10,296,796 B2 | 5/2019 | Cosatto |
| 10,297,070 B1 | 5/2019 | Zhu |
| 10,482,355 B2 | 11/2019 | Heifets |
| 10,546,237 B2 * | 1/2020 | Heifets ................. G06F 18/214 |
| 2002/0038184 A1 | 3/2002 | Waldman et al. |
| 2002/0042785 A1 | 4/2002 | Raz |
| 2002/0090631 A1 | 7/2002 | Gough et al. |
| 2005/0228592 A1 | 10/2005 | Ahuja et al. |
| 2006/0034495 A1 | 2/2006 | Miller et al. |
| 2006/0089335 A1 | 4/2006 | Liu et al. |
| 2006/0178862 A1 | 8/2006 | Chan et al. |
| 2007/0061118 A1 | 3/2007 | Friesner et al. |
| 2007/0111257 A1 | 5/2007 | Kohne |
| 2009/0006059 A1 | 1/2009 | Arora |
| 2013/0280238 A1 | 10/2013 | Evans et al. |
| 2015/0112182 A1 | 4/2015 | Sharma et al. |
| 2015/0134315 A1 | 8/2015 | Sarmiento |
| 2015/0238148 A1 | 8/2015 | Georgescu et al. |
| 2015/0278441 A1 | 10/2015 | Min et al. |
| 2019/0164021 A1 | 5/2019 | Heifets |

FOREIGN PATENT DOCUMENTS

| | | |
|---|---|---|
| JP | 2010-113473 A | 5/2010 |
| JP | 2018-529159 | 10/2018 |
| WO | WO 2015/168774 A1 | 11/2015 |
| WO | WO 2017/034820 | 3/2017 |

OTHER PUBLICATIONS

Extended European search report for EP 18776308.1, dated Jan. 27, 2020, 9 pages.
Abel-Hamid et al., "Exploring Convolutional Neural Network Structures and Optimization Techniques for Speech Recognition", Aug. 1, 2013, Interspeech 2013.
Chae et al., 2010,"Predicting protein complex geometries with a neural network," Proteins: Structure, Function and Bioinformatics 78.4 (2010): 1026-1039, 14 pages.
Clevert et al., 2014, "Rectified Factor Networks and Dropout," Deep Learning and Representation Learning Workshop, in conjunction with Neural Information Processing Systems (NIPS).
Da and Kireey, 2014, J. Chem. Inf. Model. 54, pp. 2555-2561, "Structural Protein-Ligand Interaction Fingerprints (SPLIF) for Structure-Based Virtual Screening: Method and Benchmark Study".
Dean et al., "Large Scale Distributed Deep Networks", Google AI, NIPS 2012.
Extended European search report for EP 16854180.3, dated Jun. 3, 2019, 5 pages.
Durrant et al., "NNScore 2.0: A Neural-Network Receptor-Ligand Scoring Function", Journal of Chemical Information and Modeling American Chemical Society USA, vol. 51, No. 11, Nov. 28, 2011.
Fariselli et al., 2002, "Prediction of protein-protein interaction sites in heterocomplexes with neural networks," Eur. J. Biochem., 269, pp. 1356-1361.
Giguere et al., "Learning a peptide-protein binding affinity predictor with kernel ridge regression", Jul. 31, 2012, arXiv:1207.7253v1 [q-bio.QM].
Khamis et al., "Deep Learning is competing random forest in computational docking", Arvix.org, Cornell University Library, Aug. 24, 2016.
Khan et al., "One-Class Classification: Taxonomy of Study and Review of Techniques", The Knowledge of Engineering Review, 2004, p. 1-35.
Kitchen et al. 2004, "Docking and scoring in virtual screening for drug discovery: methods and applications," Nat. Rev Drug Discov. 3, No. 11, pp. 935-949.
Krizheysky et al., 2012, "ImageNet Classification with Deep Convolutional Neural Networks," in *Advances in Neural Information Processing Systems* 25 (NIPS 2012), eds. Pereira et al.
LeCun et al., "Gradient-Based Learning Applied to Document Recognition", Nov. 1998, Proc. of the IEEE, vol. 86, Issue 11.
LeCun et al., "Learning Methods for Generic Object Recognition and Invariance to Pose and Lighting", CVPR, Washington D.C., 2004.
Lobanov et al., "Using artificial neural networks to drive virtual screening of combinatorial libraries", Drug Discovery Today, Biosilico, Elsevier, Avenel, US, vol. 2, No. 4, Jul. 1, 2004.
Morris et al., 2009, "AutoDock 4 and AutoDockTools4: Automated Docking with Selective Receptor Flexibility," in *J Compt Chem.* Dec. 2009; 30(16): 2785-2791.
Muegge et al., "Advances in virtual screening", Drug Discovery Today: Technologies, Elsevier, Amsterdam, NL, vol. 3, No. 4, Jan. 30, 2007, pp. 405-4011.
Nukada et al., "High Performance 3D Convolution for Protein Docking on IBM Blue Gene," Parallel and Distributed Processing and Applications, Springer Berlin Heidelberg, 2007, pp. 958-969.
Ramsundar et al., Feb. 6, 2015, "Massively Multitask Networks for Drug Discovery," arXiv:1502.02072v1.
Rarey et al., 1996, "A Fast Flexible docking Method using an Incremental Construction Algorithm," in *Journal of Molecular Biology* (1996) 261, pp. 470-489.
Seifert et al., "Targeted scoring functions for virtual screening", Drug Discovery Today, Elsevier, Amsterdam, NL, vol. 14, No. 11-12, Jun. 1, 2009.
Senanayake et al., "Machine Learning based search space optimisation for drug discovery", 2013 IEEE Symposium on Computational Intelligence in Bioinformatics and Computational Biology (CIBCB), IEEE, Apr. 16, 2013, pp. 68-75.
Stahl et al., "Mapping of protein surface cavities and prediction of enzyme class by a self-organizing neural network," *Protein Engineering*, 2000, vol. 13 no. 2, pp. 83-88.
Unterthiner et al., 2014, "Deep Learning as an Opportunity in Virtual Screening," Deep Learning and Representation Learning Workshop, in conjunction with Neural Information Processing Systems (NIPS).
Unterthiner et al., Mar. 4, 2015, "Toxicity Prediction using Deep Learning," arXiv:1503.01445.

(56) References Cited

OTHER PUBLICATIONS

Vanhoucke et al., "Improving the speed of neural networks on CPUs", Google AI, NIPS 2011.

Volkamer et al., "Analyzing the topology of active sites: on the prediction of pockets and subpockets," Journal of chemical information and modeling 50.11 (2010): 2041-2052, 12 pages.

Wallach et al., Oct. 10, 2015, arXiv:1510.02855.1, "AtomNet: A Deep Convolutional Neural Network for Bioactivity Prediction in Structure-based Drug Discovery".

Wriggers et al., "Topology representing neural networks reconcile biomolecular shape, structure, and dynamics," *Neurocomputing* 56, 2004, pp. 365-379.

Xu et al., "Deep Convolutional Neural Network for Image Deconvolution", NIPS 2014.

Zeng et al., "Convolutional Neural Network Architectures for predicting DNA-protein binding", *Bioinformatics*, vol. 32, No. 12, Jun. 15, 2016.

International Search Report and Written Opinion for International Patent Application No. PCT/CA2015/000296, Jul. 24, 2015, 7 pages.

International Search Report and Written Opinion for International Patent Application No. PCT/US2016/055369.

International Search Report and Written Opinion for International Patent Application No. PCT/US2018/024474, Oct. 18, 2018, 7 pages.

* cited by examiner

| 202 | A computer 100 system and method for classification of a test object 72 are provided. The computer system comprises at least one processor 74 and nontransitory memory 90/92 addressable by the at least one processor. The nontransitory memory stores one or more programs for execution by the at least one processor. The one or more programs comprise instructions for enacting the method. |

| 204 | A description of the test object 72 is obtained. |
| 206 | The test object 72 is a chemical compound having a molecular weight of less than 2000 Daltons. |
| 208 | The test object 72 is a chemical compound that satisfies the Lipinski rule of five criterion. |
| 209 | The test object 72 is a chemical compound, and the description of the test object comprises modeled atomic coordinates for the chemical compound. |

| 210 | For each respective target object 58 in a first plurality of target objects, perform a first procedure: |
| 212 | Pose the description 60 of the test object against the respective target object thereby obtaining a description of an interaction between the test object and the respective target object. |
| 214 | Each target object 58 in the first plurality of different target objects is a polymer (e.g., a protein, a polypeptide, a polynucleic acid, a polyribonucleic acid, a polysaccharide, or an assembly of any combination thereof). |
| 216 | A respective target object 58 in the first plurality of target objects is a polymer, and the posing the description of the test object against the respective target object comprises posing the description of the test object against spatial coordinates for the respective target object in the form of a set of three-dimensional coordinates $\{x_1, ..., x_N\}$ for a crystal structure of the polymer resolved at a resolution of 3.3 Å or better, or at a resolution of 2.5 Å or better. |
| 218 | A respective target object 58 in the first plurality of target objects is a polymer, and the posing the description of the test object against the respective target object comprises posing the description of the test object of the target object against spatial coordinates for the respective target object in the form of an ensemble of three-dimensional coordinates for the polymer determined by nuclear magnetic resonance, neutron diffraction, or cryo-electron microscopy. |

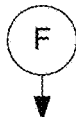

The second classifier 108 is trained on a plurality of training vectors 116. Each respective training vector in the plurality of training vectors is the output from the first classifier 102 after inputting a corresponding training object 113 in a first plurality of training objects as a test object in accordance with the first procedure. Each training object 113 in a first subset of the first plurality training objects is uniquely associated with a corresponding target object in the first plurality of target objects. Each training object in a second subset of the first plurality of training objects is associated with no target object in the first plurality of target objects. — 274

The first subset of the first plurality of training objects comprises 1000 training objects 113, and the first plurality of target objects 72 comprises 100 target objects. For each respective target object in the first plurality of target objects, the first subset of the first plurality of training objects includes at least five training objects that are uniquely associated with the respective target object, and the second subset of the first plurality of training objects comprises 10000 training objects. — 276

Each respective training object 113 in the first plurality of training objects is a chemical compound with a corresponding molecular fingerprint (e.g., Daylight fingerprint, a BCI fingerprint, an ECFP fingerprint, an ECFC fingerprint, an MDL fingerprint, an APFP fingerprint, a TTFP fingerprint, or a UNITY 2D fingerprint) that is dissimilar to the molecular fingerprint of any training object in the first plurality of training objects that is not uniquely associated with the same target object as the respective training object. — 278

The corresponding molecular fingerprint of the respective training object is deemed to be dissimilar to the molecular fingerprint of another training object in the first plurality of training objects when the Tanimoto coefficient between the respective training object and the molecular fingerprint of the other training object is less than 0.70, or less than 0.60, or less than 0.50. — 280

Fig. 2G $$f(\overrightarrow{x_1}, \overrightarrow{x_2}, \ldots, \overrightarrow{x_{100}}) = g(g_0(\overrightarrow{x_1}, \overrightarrow{x_2}, \ldots, \overrightarrow{x_{100}}), g_1(\overrightarrow{x_1}, \overrightarrow{x_2}, \ldots, \overrightarrow{x_{100}}), \ldots, g_n(\overrightarrow{x_1}, \overrightarrow{x_2}, \ldots, \overrightarrow{x_{100}}))$$

$$\overrightarrow{x_1} = (x_1^1, x_1^2, \ldots, x_1^{40})$$
$$\overrightarrow{x_2} = (x_2^1, x_2^2, \ldots, x_2^{40})$$

Fig. 10

SYSTEMS AND METHODS FOR CORRECTING ERROR IN A FIRST CLASSIFIER BY EVALUATING CLASSIFIER OUTPUT IN PARALLEL

CROSS REFERENCE TO RELATED APPLICATION

This application is a continuation of U.S. Pat. No. 10,546,237, issued Jan. 28, 2020, which is hereby incorporated by reference in its entirety.

TECHNICAL FIELD

This following relates generally to correcting error, such as bias, of a classifier through the evaluation of successive outputs from the classifier in a parallel fashion, where the classifier is tasked with classifying a test object.

BACKGROUND

The application of classifiers, such as deep learning techniques, can be used to generate relevant insights from large volumes of data. The use of classifiers is being explored across a variety of areas. Specifically, in healthcare, the American Recovery and Reinvestment Act of 2009 and the Precision Medicine Initiative of 2015 have widely endorsed the value of medical data in healthcare. Owing to several such initiatives, medical big data is expected to grow approximately 50-fold to reach 25,000 petabytes by 2020. See, Roots Analysis, Feb. 22, 2017, "Deep Learning in Drug Discovery and Diagnostics, 2017-2035," available on the Internet at rootsanalysis.com.

Classifiers can be used to generate valuable/meaningful insights using conventional data mining techniques. Lead identification and optimization in drug discovery, support in patient recruitment for clinical trials, medical image analysis, biomarker identification, drug efficacy analysis, drug adherence evaluation, sequencing data analysis, virtual screening, molecule profiling, metabolomic data analysis, EMR analysis and medical device data evaluation, off-target side-effect prediction, toxicity prediction, potency optimization, drug repurposing, drug resistance prediction, personalized medicine, drug trial design, agrochemical design, material science and simulations are examples of applications where the use of classifiers, such as deep learning based solutions are being explored.

The likely benefits associated with the use of classifier based solutions in the above mentioned areas is estimated to be worth several billions of dollars. For example, there are well-known instances where deep learning models have accelerated the drug discovery process and provided solutions to precision medicine. With applications in drug repurposing and preclinical research, the application of classifiers in drug discovery is likely to have great opportunity. In diagnostics, an increase in the speed of diagnosis based on classifiers is likely to have a profound impact in regions with large patient to physician ratios. The implementation of such solutions will increase the efficiency of physicians, thereby providing relief to the overly-burdened global healthcare system.

One drawback with classifiers is their error. Two main sources of classifier error are bias and variance. The error due to bias is taken as the difference between the expected (or average) prediction of a classifier and the correct value which the classifier is trying to predict. Because there is typically only one classifier used in an application, the concept of an expected or average prediction value for the classifier is counterintuitive. However, if one were to repeat the classifier training process more than once, each time using new training data and run a new analysis creating a new classifier, due to randomness in the underlying data sets, the resulting classifier will have a range of predictions. Bias measures how far off in general these classifier's predictions are from the correct value. For instance, using a phonebook to select participants in a survey used to train a classifier is a source of bias. By only surveying certain classes of people (those people that have a registered phone number), it skews the results in a way that will be consistent if we repeated the entire classifier building exercise. Similarly, not following up with respondents is another source of bias, as it consistently changes the mixture of responses obtained.

Classifier error due to variance is taken as the variability of a classifier prediction for a given data point. Again, if the entire classifier building process is repeated multiple times, the variance is how much the predictions for a given point vary between different realizations of the classifier. A small sample size for a training population is a source of variance. If the sample size is increased, the results would be more consistent each time the survey and prediction is repeated during classifier training. The results still might be highly inaccurate due to large sources of bias, but the variance of predictions will be reduced.

In the art, total error of the model has been minimized by a careful balancing of bias and variance. However, as classifiers, such as deep learning classifiers, get more complex and are applied to more types of data such as unstructured data and/or data for which very few replicates can be used in the training set, error becomes increasing more difficult to detect, let alone correct. Given the above background, there is a need for solutions that remove error, such as bias, in a classifier, in order to provide more accurate results. Removal or improvement in such error will have application in lead identification and optimization in drug discovery, support in patient recruitment for clinical trials, medical image analysis, biomarker identification, drug efficacy analysis, drug adherence evaluation, sequencing data analysis, virtual screening, molecule profiling, metabolomic data analysis, EMR analysis, medical device data evaluation, off-target side-effect prediction, toxicity prediction, potency optimization, drug repurposing, drug resistance prediction, personalized medicine, drug trial design, agrochemical design, material science and simulations to name a few practical applications where the use of improved classifiers have value.

SUMMARY

The present disclosure addresses the deficiencies identified in the background by providing systems and methods for improving classifier error, such as bias, in order to classify a test object. For each respective target object in a plurality of target objects, a first procedure is performed. The first procedure comprises posing the test object against the respective target object thereby obtaining an interaction between the test object and the target object. The first procedure further scores the interaction with a first classifier. Each such score across the plurality of target objects forms a test vector that is inputted into a second classifier thereby obtaining an indication of a target object from among the plurality of target objects. The second classifier is trained on training vectors, each being the output from instances of the first classifier after inputting a corresponding training object in a plurality of training objects in accordance with the first procedure. Each object in one subset of the training objects is uniquely associated with one of the targets. Another subset of the training objects is not associated with the targets. In this way, error in the first classifier, such as bias, is corrected by the second classifier.

One aspect of the present disclosure provides a computer system for classification of a test object. The computer system comprises at least one processor and nontransitory memory addressable by the least one processor. The nontransitory memory stores one or more programs for execution by the at least one processor. The one or more programs comprises instructions for obtaining a description of a test object.

For each respective target object in a first plurality of target objects, the one or more programs comprises instructions for performing a first procedure. The first procedure comprises posing the description of the test object against the respective target object thereby obtaining a description of an interaction between the test object and the respective target object. The first procedure comprises inputting the description of the interaction between the test object and the respective target object to a first classifier thereby obtaining a corresponding score for the interaction between the test object and the respective target object from the first classifier. In this way, each corresponding score for the interaction between the test object and a respective target object across the first plurality of target objects forms a test vector for the test object. The test vector for the test object is inputted to a second classifier thereby obtaining a transformation for the test vector as output from the second classifier. The transformation provides an indication of a single target object in the first plurality of target objects.

In accordance with this aspect of the present disclosure, the second classifier is trained on a plurality of training vectors. Each respective training vector in the plurality of training vectors is the output from the first classifier after inputting a corresponding training object in a first plurality of training objects as a test object in accordance with the first procedure. Each training object in a first subset of the first plurality training objects is uniquely associated with a corresponding target object in the first plurality of target objects. Each training object in a second subset of the first plurality of training objects is associated with no target object in the first plurality of target objects.

In some embodiments, the posing the description of the test object against the respective target object thereby obtaining a description of an interaction between the test object and the respective target object is performed by a second procedure that comprises: modeling the test object with the respective target object in each pose of a plurality of different poses, thereby creating a plurality of voxel maps, where each respective voxel map in the plurality of voxel maps comprises the test object in a respective pose in the plurality of different poses. Each voxel map in the plurality of voxel maps is unfolded into a corresponding first classifier input vector, thereby creating a plurality of first classifier input vectors, where each first classifier input vector in the plurality of first classifier input vectors is the same size. In such embodiments, the inputting the description of the interaction between the test object and the respective target object to a first classifier comprises inputting each respective first classifier input vector in the plurality of first classifier input vectors to the first classifier.

In some such embodiments, a respective target object in the first plurality of target objects is a polymer with an active site, the test object is a chemical composition, and the modeling the test object with the respective target object in each pose of a plurality of different poses comprises performing a molecular dynamics run of an atomic representation of the test object bound to an atomic representation of the respective target object thereby forming a trajectory of the test object and the respective target object together over time. In such embodiments, at least a subset of the plurality of different poses is obtained by taking snapshots of the trajectory over a period of time.

In some such embodiments, the first classifier comprises a network architecture that includes (i) an input layer for sequentially receiving respective first classifier input vectors in the plurality of first classifier input vectors, (ii) a plurality of convolutional layers, and (iii) a scorer. Further, the plurality of convolutional layers includes an initial convolutional layer and a final convolutional layer, and each layer in the plurality of convolutional layers is associated with a different set of weights. Responsive to the inputting of a respective first classifier input vector in the plurality of first classifier input vectors to the first classifier, the input layer feeds a first plurality of values into the initial convolutional layer as a first function of values in the respective first classifier input vector. Each respective convolutional layer, other than the final convolutional layer, feeds intermediate values, as a respective second function of (i) the different set of weights associated with the respective convolutional layer and (ii) input values received by the respective convolutional layer, into another convolutional layer in the plurality of convolutional layers. The final convolutional layer feeds final values, as a third function of (i) the different set of weights associated with the final convolutional layer and (ii) input values received by the final convolutional layer, into the scorer. In such embodiments, the second procedure further comprises obtaining a plurality of scores from the scorer, where each score in the plurality of scores corresponds to the input of a first classifier input vector in the plurality of first classifier input vectors into the input layer, and using the plurality of scores to obtain the description of the interaction between the test object and the respective target object.

In some such embodiments, the computer system further comprises a graphical processing unit having a graphical processing memory, and the graphical processing memory comprises the network architecture.

In some such embodiments, the scorer comprises a plurality of fully-connected layers and an evaluation layer, and a fully-connected layer in the plurality of fully-connected layers feeds into the evaluation layer.

In some such embodiments, the scorer comprises an implementation of decision tree, a multiple additive regression tree, a clustering algorithm, principal component analysis, a nearest neighbor analysis, a linear discriminant analysis, a quadratic discriminant analysis, a support vector machine, an evolutionary method, a projection pursuit, a logistic regression, or ensembles thereof.

In some such embodiments, a convolutional layer in the plurality of convolutional layers has a plurality of filters, and each filter in the plurality of filters convolves a cubic input space of $N^3$ with stride Y, wherein N is an integer of two or greater and Y is a positive integer. In some embodiments, the different set of weights associated with the convolutional layer are associated with respective filters in the plurality of filters.

In some embodiments, the scorer comprises a plurality of fully-connected layers and a logistic regression cost layer, and a fully-connected layer in the plurality of fully-connected layers feeds into the logistic regression cost layer.

In some such embodiments, each first classifier input vector in the plurality of first classifier input vectors is one-dimensional. In some embodiments, the plurality of different poses comprises 2 or more poses, 10 or more poses, 100 or more poses, or 1000 or more poses. In some embodiments, the plurality of different poses is obtained using a docking scoring function in one of a Markov chain Monte Carlo sampling, simulated annealing, a Lamarckian Genetic Algorithm, a genetic algorithm, or a deep convolutional neural net sampling. In some embodiments, the plurality of different poses is obtained by incremental search using a greedy algorithm.

In some embodiments, the second procedure further comprises obtaining a plurality of scores from the first classifier, where each score in the plurality of scores corresponds to the input of a first classifier input vector in the plurality of first classifier input vectors into the first classifier. The plurality of scores is used to obtain the description of the interaction between the test object and the respective target object. In such embodiments, the test object is a chemical compound. The using the plurality of scores to obtain the description of the interaction between the test object and the respective target object comprises taking a measure of central tendency of the plurality of scores. When the measure of central tendency satisfies a predetermined threshold value or predetermined threshold value range, the description of the interaction between the test object and the respective target object is deemed to have a first classification. When the measure of central tendency fails to satisfy the predetermined threshold value or predetermined threshold value range, the description of the interaction between the test object and the respective target object is deemed to have a second classification. In some such embodiments, the first classification is a prediction that the test object binds to the respective target object with an $IC_{50}$, $EC_{50}$, Kd, KI or percent inhibition that is below a first binding value, and the second classification is a prediction that the test object binds to the respective target object with an $IC_{50}$, $EC_{50}$, Kd, KI, or percent inhibition that is above the first binding value (e.g., one nanomolar, ten nanomolar, one hundred nanomolar, one micromolar, ten micromolar, one hundred micromolar, or one millimolar, etc.).

In alternative embodiments, the second procedure further comprises obtaining a plurality of scores from the first classifier, where each score in the plurality of scores corresponds to the input of a first classifier input vector in the plurality of first classifier input vectors into the first classifier, and the plurality of scores is sued to obtain the description of the interaction between the test object and the respective target object. The using the plurality of scores to obtain the description of the interaction between the test object and the respective target object comprises taking a weighted average of the plurality of scores. When the weighted average satisfies a predetermined threshold value or predetermined threshold value range, the test object is deemed to have a first classification. When the weighted average fails to satisfy the predetermined threshold value or predetermined threshold value range, the test object is deemed to have a second classification. In some such embodiments, the weighted average is a Boltzman average of the plurality of scores. In some such embodiments, the first classification is an $IC_{50}$, $EC_{50}$, Kd, KI, or percent inhibition for the test object with respect to the respective target object that is above a first binding value, and the second classification is an $IC_{50}$, $EC_{50}$, Kd, KI, or percent inhibition for the test object with respect to the respective target object that is below the first binding value (e.g., one nanomolar, ten nanomolar, one hundred nanomolar, one micromolar, ten micromolar, one hundred micromolar, or one millimolar, etc.). In some such embodiments, the first classification is a prediction that the test object binds to the respective target object with an $IC_{50}$, $EC_{50}$, Kd, KI or percent inhibition that is below a first binding value, and the second classification is a prediction that the test object binds to the respective target object with an $IC_{50}$, $EC_{50}$, Kd, KI or percent inhibition that is above the first binding value (e.g., one nanomolar, ten nanomolar, one hundred nanomolar, one micromolar, ten micromolar, one hundred micromolar, or one millimolar, etc.).

In some embodiments, each target object in the first plurality of different target objects is a polymer (e.g., a protein, a polypeptide, a polynucleic acid, a polyribonucleic acid, a polysaccharide, or an assembly of any combination thereof).

In some embodiments, a respective target object in the first plurality of target objects is a polymer, and the posing the description of the test object against the respective target object comprises posing the description of the test object against spatial coordinates for the respective target object in the form of a set of three-dimensional coordinates $\{x_1, \ldots, x_N\}$ for a crystal structure of the polymer resolved at a resolution of 3.3 Å or better, 2.5 Å or better, or 2.0 Å or better.

In some embodiments, a respective target object in the first plurality of target objects is a polymer and the posing the description of the test object against the respective target object comprises posing the description of the test object of the target object against spatial coordinates for the respective target object in the form of an ensemble of three-dimensional coordinates for the polymer determined by nuclear magnetic resonance, neutron diffraction, or cryo-electron microscopy.

In some embodiments, each respective target object in the first plurality of target objects is a polymer with an active site, the test object is a chemical composition, and the posing the description of the test object against the respective target object comprises docking an atomic representation of the test object into an atomic representation of the active site of the polymer.

In some embodiments, the first classifier comprises a plurality of weights and the method further comprising, prior to the obtaining a description of a test object, acquiring a training data set. The training data set comprises a second plurality of training objects, a second plurality of target objects, and a plurality of experimentally determined scores. Each respective experimentally determined score in the plurality of experimentally determined scores is for the interaction between a corresponding training object in the second plurality of training objects and a corresponding target object in the second plurality of target objects. For each respective training object in the second plurality of training objects, performing a second procedure comprises posing a description of the respective training object against a corresponding target object in the second plurality of target objects thereby obtaining a description of an interaction between the training object and the corresponding target object. The second procedure further comprises inputting the description of the interaction between the respective training object and the corresponding target object to the first classifier thereby obtaining a corresponding score for the interaction between the training object and the corresponding target object from the first classifier. The second procedure further comprises (iii) determining a differential between (1) the corresponding score from the first classifier for the description of the interaction between the respective training object and the corresponding target object and (2) the experimentally determined score for the interaction between the respective training object and the corresponding target object from the training data set. The second procedure further comprises (iv) applying the differential to the plurality of weights. In some such embodiments, the second plurality of target objects is the same as the first plurality of target objects. In some such embodiments, there is only partial overlap between the second plurality of target objects and the first plurality of target objects. In some such embodiments, there is no overlap between the second plurality of target objects and the first plurality of target objects. In some such embodiments, the first plurality of target objects is a subset of the second plurality of target objects. In some such embodiments, the second plurality of target objects is 50 or more target objects. In some such embodiments, the second plurality of target objects is 100 or more target objects. In some such embodiments, the second plurality of target objects is 250 or more target objects. In some such embodiments, the first plurality of training objects is the same as the second plurality of training objects. In some such embodiments, the first plurality of training objects is different than the second plurality of training objects.

In some embodiments, the first subset of the first plurality of training objects comprises 1000 training objects, the first plurality of target objects comprises 100 target objects and, for each respective target object in the first plurality of target objects, the first subset of the first plurality of training objects includes at least 5 target objects that are uniquely associated with the respective target object and the second subset of the first plurality of training objects comprises 10000 training objects.

In some embodiments, each respective training object in the first plurality of training objects is a chemical compound with a corresponding molecular fingerprint that is dissimilar to the molecular fingerprint of any training object in the first plurality of training objects that is not uniquely associated with the same target object as the respective training object. In some such embodiments, the corresponding molecular fingerprint is a Daylight fingerprint, a BCI fingerprint, an ECFP fingerprint, an ECFC fingerprint, an MDL fingerprint, an atom pair fingerprint (APFP fingerprint), a topological torsion fingerprint (TTFP fingerprint), or a UNITY 2D fingerprint of the respective training object. In some embodiments, the corresponding molecular fingerprint of the respective training object is deemed to be dissimilar to the molecular fingerprint of another training object in the first plurality of training objects when the Tanimoto coefficient between the respective training object and the molecular fingerprint of the other training object is less than 0.70 or less than 0.60.

In some embodiments, the first classifier comprises a neural network or a support vector machine.

In some embodiments, the second classifier comprises a logistic regression algorithm, a random forest, a nonlinear regression model, a linear regression algorithm, a kernel method, a decision tree, multivariate splines (MARS), or a multiple additive regression tree.

In some embodiments, the test object is a chemical compound having a molecular weight of less than 2000 Daltons. In some embodiments, the test object is a chemical compound that satisfies the Lipinski rule of five criterion. In some embodiments, the test object is a chemical compound, and the description of the test object comprises modeled atomic coordinates for the chemical compound.

In some embodiments, the test object is a chemical compound, the respective target object comprises a polymer with a binding pocket, and the posing the description of the test object against the respective target object comprises docking modeled atomic coordinates for the chemical compound into atomic coordinates for the binding pocket.

In some embodiments, the corresponding score for the interaction between the test object and the respective target object from the first classifier is a numerical score. In some embodiments, the corresponding score for the interaction between the test object and the respective target object from the first classifier is a numerical score between zero and one.

In some embodiments, the first plurality of target objects comprises 100 target objects, the test vector for the test object comprises 100 elements, and each element for the score for the interaction between the test object and a respective target object in the first plurality of target objects from the first classifier.

Another aspect of the present disclosure provides a method for classification of a test object. The method comprises performing any of the methods disclosed herein.

Another aspect of the present disclosure provides a method for classification of a test object. The method comprises obtaining a description of the test object. For each respective target object in a first plurality of target objects, the method comprises performing a first procedure. The first procedure comprises posing the description of the test object against the respective target object thereby obtaining a description of an interaction between the test object and the respective target object. The first procedure further comprises inputting the description of the interaction between the test object and the respective target object to a first classifier thereby obtaining a corresponding score for the interaction between the test object and the respective target object from the first classifier. Each corresponding score for the interaction between the test object and a respective target object across the first plurality of target objects forms a test vector for the test object. The method further comprises inputting the test vector for the test object to a second classifier thereby obtaining a transformation for the test vector as output from the second classifier. The transformation provides an indication of a single target object in the first plurality of target objects. The second classifier is trained on a plurality of training vectors. Each respective training vector in the plurality of training vectors is the output from the first classifier after inputting a corresponding training object in a first plurality of training objects as a test object in accordance with the first procedure. Each training object in a first subset of the first plurality training objects is uniquely associated with a corresponding target object in the first plurality of target objects. Each training object in a second subset of the first plurality of training objects is associated with no target object in the first plurality of target objects.

Another aspect of the present disclosure provides a non-transitory computer-readable storage medium having stored thereon instructions, which, when executed by a processor in a system for classification of a test object, cause the processor to perform the operations of any of the methods disclosed herein.

Another aspect of the present disclosure provides a non-transitory computer-readable storage medium having stored thereon instructions, which, when executed by a processor in a system for classification of a test object, cause the processor to perform the operations of obtaining a description of the test object. For each respective target object in a first plurality of target objects, the instructions further cause the processor to perform a first procedure comprising posing the description of the test object against the respective target object thereby obtaining a description of an interaction between the test object and the respective target object. The first procedure further comprises inputting the description of the interaction between the test object and the respective target object to a first classifier thereby obtaining a corresponding score for the interaction between the test object and the respective target object from the first classifier. Each corresponding score for the interaction between the test object and a respective target object across the first plurality of target objects forms a test vector for the test object. The instructions further cause the processor to input the test vector for the test object to a second classifier thereby obtaining a transformation for the test vector as output from the second classifier. The transformation provides an indication of a single target object in the first plurality of target objects. The second classifier is trained on a plurality of training vectors. Each respective training vector in the plurality of training vectors is the output from the first classifier after inputting a corresponding training object in a first plurality of training objects as a test object in accordance with the first procedure. Each training object in a first subset of the first plurality training objects is uniquely associated with a corresponding target object in the first plurality of target objects. Furthermore, each training object in a second subset of the first plurality of training objects is associated with no target object in the first plurality of target objects.

BRIEF DESCRIPTION OF THE DRAWINGS

In the drawings, embodiments of the systems and method of the present disclosure are illustrated by way of example. It is to be expressly understood that the description and drawings are only for the purpose of illustration and as an aid to understanding, and are not intended as a definition of the limits of the systems and methods of the present disclosure.

FIGS. 2A, 2B, 2C, 2D, 2E, 2F, 2G and 2H illustrate methods for correcting error, such as bias, of a classifier through the evaluation of successive outputs from the classifier in a parallel fashion, where the classifier is tasked with classifying a test object, and where optional steps are indicated by dashed boxes, in accordance with some embodiments.

FIG. 10 is a depiction of applying multiple function computation elements ($g_1$, $g_2$, ... ) to the voxel inputs ($x_1$, $x_2$, ..., $x_{100}$) and composing the function computation element outputs together using g( ), according to an embodiment.

Like reference numerals refer to corresponding parts throughout the several views of the drawings.

DETAILED DESCRIPTION

Figure 1A:
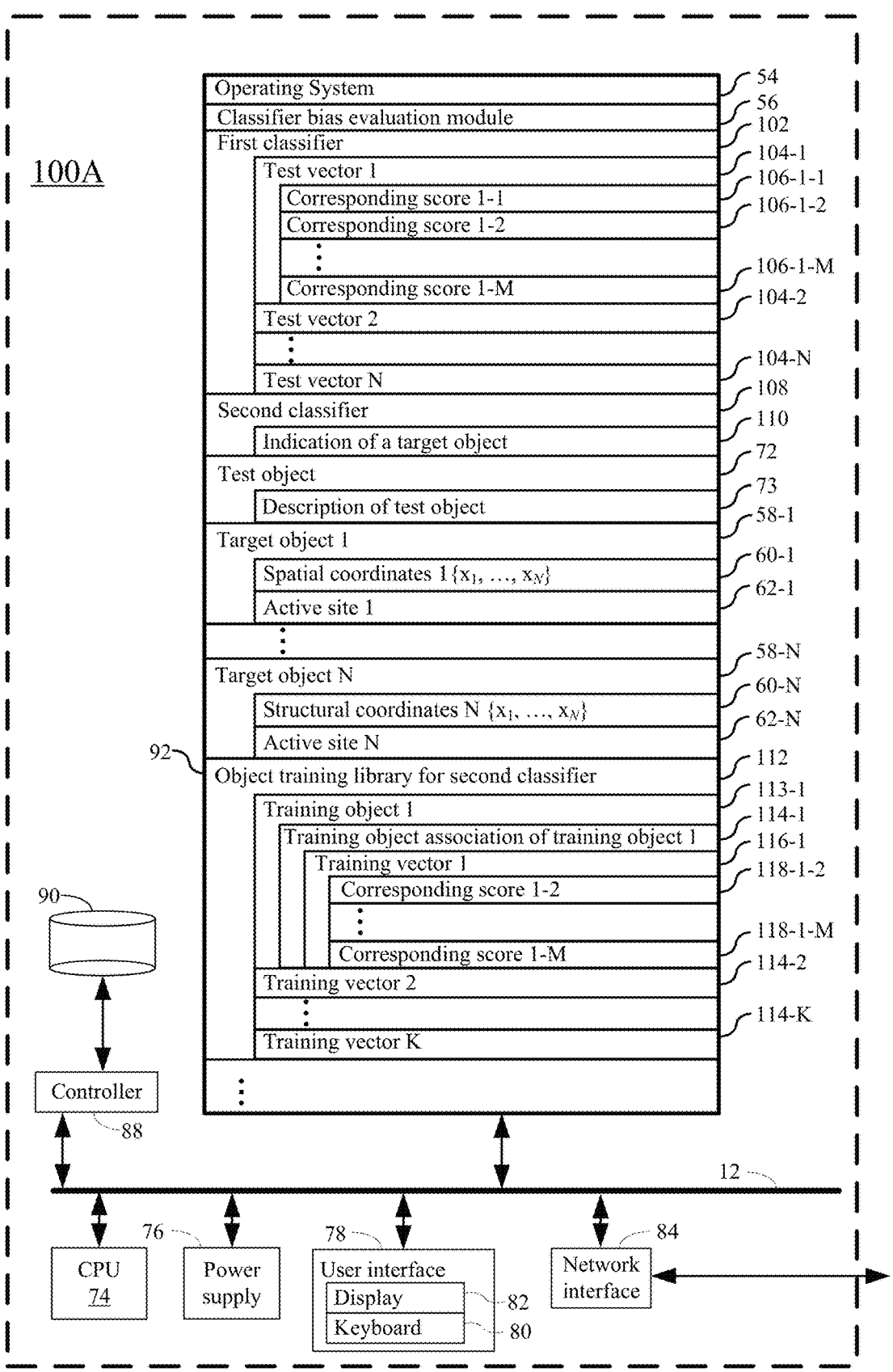
FIG. 1A illustrates a computer system for correcting error, such as bias, of a classifier through the evaluation of successive outputs from the classifier in a parallel fashion, where the classifier is tasked with classifying a test object in accordance with some embodiments.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The present disclosure provides systems and methods for classifying a test object using a first and second classifier. The second classifier works to minimize or reduce error such as bias, in the first classifier. The test object is classified against a plurality of target objects by the first and second classifier, and ultimately both the first and second classifier select which one of the target objects the test object is associated with. As an example, in some embodiments, the test object is a small molecule compound and each target object is a protein having an active site (e.g., an enzyme). The first and second classifier use the atomic coordinates of each target object and the test object to determine which target object, if any, the test object binds to. In the present disclosure this is done as follows. For each respective target object in the plurality of target objects, a first procedure is performed. In the first procedure the test object is posed against the respective target thereby obtaining an interaction between the test and target. For instance, in the small molecule example above, the small molecule is docked in the active site of the respective target object in some orientation. The first procedure continues by scoring the interaction between the test object and the target object with the first classifier. The first procedure is independently performed on the test object with each target object in the plurality of target objects to obtain a score for each such target object with the test object. Each such score across the plurality of target objects forms a test vector. Each element of the test vector is a score from the first classifier for the interaction between the test object and a respective target object. The test vector is inputted into the second classifier thereby obtaining an indication of the target object. Prior to performing the first procedure with the test object, the second classifier is trained on training vectors. Each such training vector is the output from an instance of the first classifier after inputting a corresponding training object in a plurality of training objects in accordance with the first procedure. That is, a training object, whose affinity to one or more target objects is known, is inputted into the first classifier in accordance with the first procedure. Thus, for each of the one or more target objects for which the affinity between the training object and the target object is known, the first classifier evaluates the interaction between the training object and the target object and compared to the actual affinity. These comparisons are then used to train the first classifier. Each object in one subset of the training objects is uniquely associated with one of the targets. For instance, in the example of the small molecule compound binding a protein, the small molecule binds to one of the target proteins but has no appreciable binding to the other target proteins. Another subset of the training objects is not associated with the targets.

FIG. 1 illustrates a computer system 100 that implements the methods described in the present disclosure. For instance, it can be used as a binding affinity prediction system to generate accurate predictions regarding the binding affinity of one or more test objects (e.g., chemical compounds) with a set of one or more target objects (e.g., polymers).

Figure 1B:
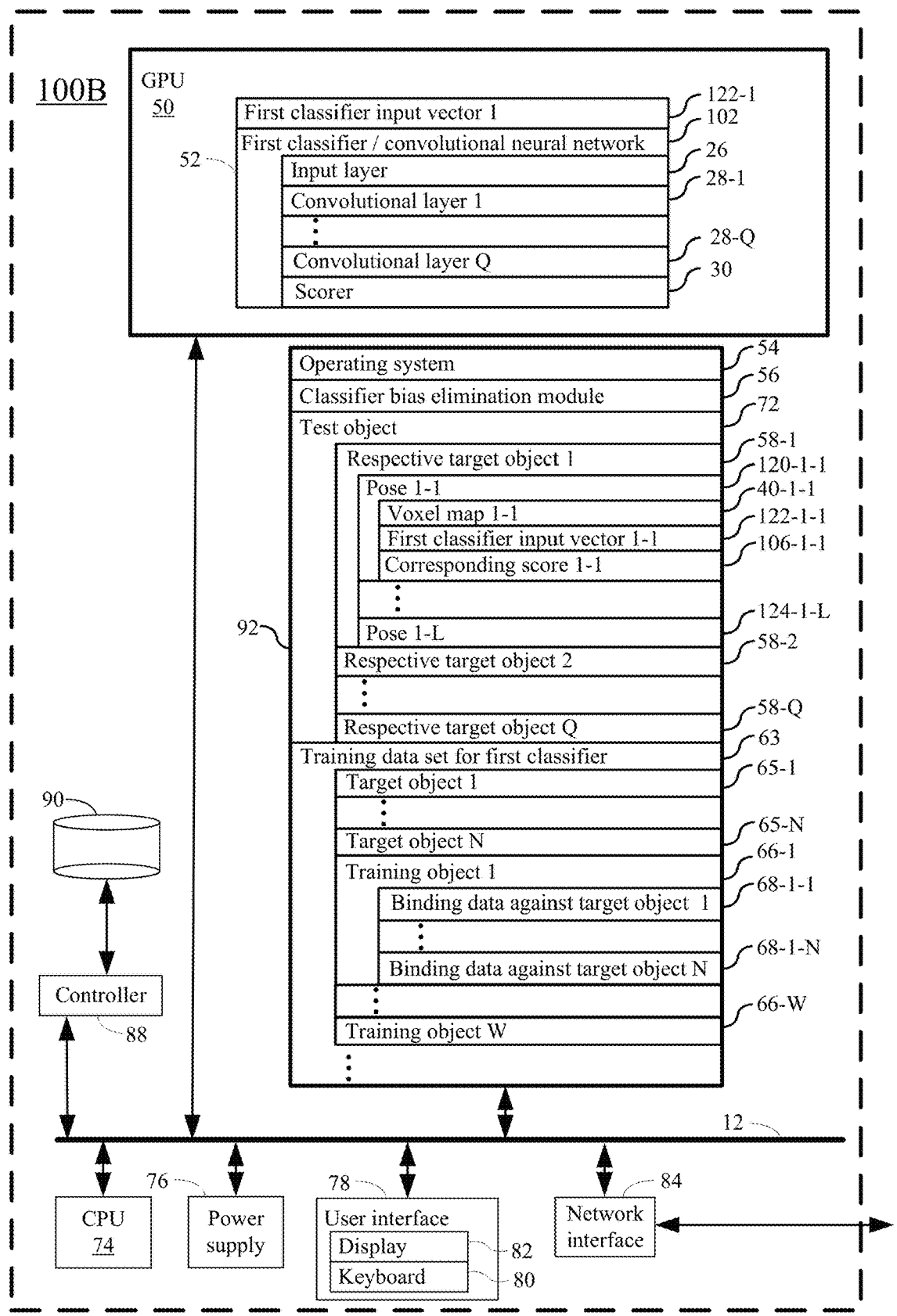
FIG. 1B illustrates a computer system for correcting error, such as bias, of a classifier through the evaluation of successive outputs from the classifier in a parallel fashion, where the classifier is tasked with classifying a test object in accordance with some embodiments.

Referring to FIGS. 1A and 1B, in typical embodiments, analysis computer system 100 comprises one or more computers. For purposes of illustration in FIGS. 1A and 1B, the analysis computer system 100 is represented as a single computer that includes all of the functionality of the disclosed analysis computer system 100. However, the disclosure is not so limited. The functionality of the analysis computer system 100 may be spread across any number of networked computers and/or reside on each of several networked computers. One of skill in the art will appreciate that a wide array of different computer topologies are possible for the analysis computer system 100 and all such topologies are within the scope of the present disclosure.

Turning to FIGS. 1A and 1B with the foregoing in mind, an analysis computer system 100A/100B comprises one or more processing units (CPU's) 74, a network or other communications interface 84, a user interface 78 (e.g., including a display 82 and keyboard 80 or other form of input device) a memory 92 (e.g., random access memory), one or more magnetic disk storage and/or persistent/non-volatile devices 90 optionally accessed by one or more controllers 88, one or more communication busses 12 for interconnecting the aforementioned components, and a power supply 76 for powering the aforementioned components. Data in memory 92 can be seamlessly shared with non-volatile memory 90 using known computing techniques such as caching. Memory 92 and/or memory 90 can include mass storage that is remotely located with respect to the central processing unit(s) 74. In other words, some data stored in memory 92 and/or memory 90 may in fact be hosted on computers that are external to analysis computer system 100A/100B but that can be electronically accessed by the analysis computer system over an Internet, intranet, or other form of network or electronic cable using network interface 84.

Turning to FIG. 1A, the memory 92 of analysis computer system 100A stores:
  an operating system 54 that includes procedures for handling various basic system services;
  a classifier bias evaluation module 56 for classification of a test object 72 (and training objects 66 of FIG. 1B) against target objects 58 using a first classifier 102 and a second classifier 108;
  a first classifier 102 for evaluating the interaction between a test/training object 72/66 and a respective target object 58/65;
  one or more test vectors 104, each element of a test vector 104 including a corresponding score 106 from the first classifier 102 for the interaction between a test object 72 and a respective target object 58 across a plurality of target objects;
  a second classifier 108 for transforming a test vector 104 into an indication of a single target object 110 (58) in a plurality of target objects;
  information for the test object 72, including a description 73 of the test object;
  data for the one or more target objects 58, including a description of the target objects such as structural data 60 and optionally active site information 62; and
  an object training library 112 for the second classifier 108 that includes, for each respective training object 113, the training object association 114 of the respective training object 113 in the form of a training vector 116 that includes one or more corresponding scores 118 from the first classifier 102 each such corresponding score 118 for the interaction between the respective training object 113 and a corresponding target object 58.

Turning to FIG. 1B, analysis computer system 100B further comprises a graphical processing unit (GPU) 50 with the GPU 52. The memory 92 of the analysis computer system 100B stores:
  an operating system 54 that includes procedures for handling various basic system services;
  a classifier bias evaluation module 56 for classification of a test object 72 (and training objects 66 of FIG. 1B) against target objects 58 using a first classifier 102 and a second classifier 108 (of FIG. 1A);
  information for a test object 72, the information including for each respective target object 58, one or more poses 120 of the test object 72 against the respective target object 58 and for each such pose, a voxel map 40 from which a first classifier input vector 122 is derived for the first classifier and a corresponding score 106 from the first classifier for the first classifier input vector 122; and a training data set 63 for the first classifier 102, the training data set comprising a plurality of target objects 65, a plurality of training objects 66, and for each such respective training object 66 measured interaction data (e.g., binding data) 68 for the interaction between the training object 66 and the target object.

The memory 52, or optionally memory 92, of the analysis computer system 100B stores a first classifier 24 in the form of a convolutional neural network that includes an input layer 26, one or more convolutional layers 28, and a terminal scorer 30. As such, in some embodiments, the analysis computer system 100 makes use of a first classifier 102 in the form of a convolutional neural network that is run from the memory 52 associated with one or more graphical processing units 50 in order to improve the speed and performance of the system. In some alternative embodiments, the analysis computer system 100 makes use of a convolutional neural network that is run from memory 92 rather than memory associated with a graphical processing unit 50.

In some implementations, one or more of the above identified data elements or modules of the analysis computer system 100A/100B are stored in one or more of the previously mentioned memory devices, and correspond to a set of instructions for performing a function described above. The above identified data, modules or programs (e.g., sets of instructions) need not be implemented as separate software programs, procedures or modules, and thus various subsets of these modules may be combined or otherwise re-arranged in various implementations. In some implementations, the memory 92 and/or 90 (and optionally 52) optionally stores a subset of the modules and data structures identified above. Furthermore, in some embodiments the memory 92 and/or 90 stores additional modules and data structures not described above.

Now that systems for correcting error, such as bias, of a classifier through the evaluation of successive outputs from the classifier in a parallel fashion, where the classifier is tasked with classifying a test object, methods for correcting such error is detailed with reference to FIG. 2 and discussed below.

Block 202

Referring to block 202 and FIGS. 1A and 1B, a computer system (e.g., system 100A of FIG. 1A or system 100B of FIG. 1B) and methods for classification of a test object 72 are provided. The computer system 100 comprises at least one processor 74 and nontransitory memory 90/92 addressable by the at least one processor. The nontransitory memory stores one or more programs for execution by the at least one processor. The one or more programs comprise instructions for enacting the method.

Referring to block 204 of FIG. 2A, a description of the test object 72 is obtained. In some embodiments, the test object 72 is a chemical compound having a molecular weight of less than 2000 Daltons (block 206). In some embodiments, the test object 72 is any organic compound having a molecular weight of less than 2000 Daltons, of less than 4000 Daltons, of less than 6000 Daltons, of less than 8000 Daltons, of less than 10000 Daltons, or less than 20000 Daltons.

In some embodiments, the test object 72 is a chemical compound that satisfies the Lipinski rule of five criterion (block 208). In some embodiments, the test object 72 is an organic compounds that satisfies two or more rules, three or more rules, or all four rules of the Lipinski's Rule of Five: (i) not more than five hydrogen bond donors (e.g., OH and NH groups), (ii) not more than ten hydrogen bond acceptors (e.g. N and O), (iii) a molecular weight under 500 Daltons, and (iv) a Log P under 5. The "Rule of Five" is so called because three of the four criteria involve the number five. See, Lipinski, 1997, Adv. Drug Del. Rev. 23, 3, which is hereby incorporated herein by reference in its entirety. In some embodiments, the test object 72 satisfies one or more criteria in addition to Lipinski's Rule of Five. For example, in some embodiments, the test object 72 has five or fewer aromatic rings, four or fewer aromatic rings, three or fewer aromatic rings, or two or fewer aromatic rings. In some embodiments, the test object 72 is a chemical compound, and the description of the test object comprises modeled atomic coordinates for the chemical compound (block 209).

In the present disclosure, training objects 66 are used to train a first classifier 102. In some embodiments, these training objects have any of the characteristics disclosed herein for a test object (e.g., in some embodiments a training object 66 is any organic compound having a molecular weight of less than 2000 Daltons, of less than 4000 Daltons, of less than 6000 Daltons, of less than 8000 Daltons, of less than 10000 Daltons, or less than 20000 Daltons). In some embodiments, training objects are associated with binding data 68 obtained from wet lab assays.

Blocks 210-258

Referring to block 210 of FIG. 2A, in the disclosed methods, for each respective target object 58 in a first plurality of target objects, a first procedure is performed. In some such embodiments, there are 10 or more target objects, 100 or more target objects, or 1000 or more target objects. In the first procedure, the description of the test object 72 is posed against the respective target object 58 thereby obtaining a description of an interaction between the test object and the respective target object (block 212). Then, the description of the interaction between the test object and the respective target object is inputted to a first classifier 102 thereby obtaining a corresponding score for the interaction between the test object and the respective target object from the first classifier. Now that a summary of the first procedure has been provided, more details of various embodiments of the first procedure are provided with reference to blocks 214 to 258.

In some embodiments, each target object 58 in the first plurality of different target objects is a polymer. Examples of polymers include, but are not limited to, proteins, polypeptides, polynucleic acids, polyribonucleic acids, polysaccharides, or assemblies of any combination thereof (block 214). A polymer, such as those studied using some embodiments of the disclosed systems and methods, is a large molecule composed of repeating residues. In some embodiments, the polymer is a natural material. In some embodiments, the polymer is a synthetic material. In some embodiments, the polymer is an elastomer, shellac, amber, natural or synthetic rubber, cellulose, Bakelite, nylon, polystyrene, polyethylene, polypropylene, polyacrylonitrile, polyethylene glycol, or a polysaccharide.

In some embodiments, a target object 58 is a heteropolymer (copolymer). A copolymer is a polymer derived from two (or more) monomeric species, as opposed to a homopolymer where only one monomer is used. Copolymerization refers to methods used to chemically synthesize a copolymer. Examples of copolymers include, but are not limited to, ABS plastic, SBR, nitrile rubber, styrene-acrylonitrile, styrene-isoprene-styrene (SIS) and ethylene-vinyl acetate. Since a copolymer consists of at least two types of constituent units (also structural units, or particles), copolymers can be classified based on how these units are arranged along the chain. These include alternating copolymers with regular alternating A and B units. See, for example, Jenkins, 1996, "Glossary of Basic Terms in Polymer Science," Pure Appl. Chem. 68 (12): 2287-2311, which is hereby incorporated herein by reference in its entirety. Additional examples of copolymers are periodic copolymers with A and B units arranged in a repeating sequence (e.g. (A-B-A-B-B-A-A-A-A-B-B-B)$_n$). Additional examples of copolymers are statistical copolymers in which the sequence of monomer residues in the copolymer follows a statistical rule. See, for example, Painter, 1997, *Fundamentals of Polymer Science*, CRC Press, 1997, p 14, which is hereby incorporated by reference herein in its entirety. Still other examples of copolymers that may be evaluated using the disclosed systems and methods are block copolymers comprising two or more homopolymer subunits linked by covalent bonds. The union of the homopolymer subunits may require an intermediate non-repeating subunit, known as a junction block. Block copolymers with two or three distinct blocks are called diblock copolymers and triblock copolymers, respectively.

In some embodiments, a target object 58 is in fact a plurality of polymers, where the respective polymers in the plurality of polymers do not all have the same molecular weight. In some such embodiments, the polymers in the plurality of polymers fall into a weight range with a corresponding distribution of chain lengths. In some embodiments, the polymer is a branched polymer molecule comprising a main chain with one or more substituent side chains or branches. Types of branched polymers include, but are not limited to, star polymers, comb polymers, brush polymers, dendronized polymers, ladders, and dendrimers. See, for example, Rubinstein et al., 2003, *Polymer physics*, Oxford; New York: Oxford University Press. p. 6, which is hereby incorporated by reference herein in its entirety.

In some embodiments, a target object 58 is a polypeptide. As used herein, the term "polypeptide" means two or more amino acids or residues linked by a peptide bond. The terms "polypeptide" and "protein" are used interchangeably herein and include oligopeptides and peptides. An "amino acid," "residue" or "peptide" refers to any of the twenty standard structural units of proteins as known in the art, which include imino acids, such as proline and hydroxyproline. The designation of an amino acid isomer may include D, L, R and S. The definition of amino acid includes nonnatural amino acids. Thus, selenocysteine, pyrrolysine, lanthionine, 2-aminoisobutyric acid, gamma-aminobutyric acid, dehydroalanine, ornithine, citrulline and homocysteine are all considered amino acids. Other variants or analogs of the amino acids are known in the art. Thus, a polypeptide may include synthetic peptidomimetic structures such as peptoids. See Simon et al., 1992, Proceedings of the National Academy of Sciences USA, 89, 9367, which is hereby incorporated by reference herein in its entirety. See also Chin et al., 2003, Science 301, 964; and Chin et al., 2003, Chemistry & Biology 10, 511, each of which is incorporated by reference herein in its entirety.

The target objects 58 evaluated in accordance with some embodiments of the disclosed systems and methods may also have any number of posttranslational modifications. Thus, a target object includes those polymers that are modified by acylation, alkylation, amidation, biotinylation, formylation, γ-carboxylation, glutamylation, glycosylation, glycylation, hydroxylation, iodination, isoprenylation, lipoylation, cofactor addition (for example, of a heme, flavin, metal, etc.), addition of nucleosides and their derivatives, oxidation, reduction, pegylation, phosphatidylinositol addition, phosphopantetheinylation, phosphorylation, pyroglutamate formation, racemization, addition of amino acids by tRNA (for example, arginylation), sulfation, selenoylation, ISGylation, SUMOylation, ubiquitination, chemical modifications (for example, citrullination and deamidation), and treatment with other enzymes (for example, proteases, phosphotases and kinases). Other types of posttranslational modifications are known in the art and are also included.

In some embodiments, a target object 58 is an organometallic complex. An organometallic complex is chemical compound containing bonds between carbon and metal. In some instances, organometallic compounds are distinguished by the prefix "organo-" e.g. organopalladium compounds.

In some embodiments, a target object 58 is a surfactant. Surfactants are compounds that lower the surface tension of a liquid, the interfacial tension between two liquids, or that between a liquid and a solid. Surfactants may act as detergents, wetting agents, emulsifiers, foaming agents, and dispersants. Surfactants are usually organic compounds that are amphiphilic, meaning they contain both hydrophobic groups (their tails) and hydrophilic groups (their heads). Therefore, a surfactant molecule contains both a water insoluble (or oil soluble) component and a water soluble component. Surfactant molecules will diffuse in water and adsorb at interfaces between air and water or at the interface between oil and water, in the case where water is mixed with oil. The insoluble hydrophobic group may extend out of the bulk water phase, into the air or into the oil phase, while the water soluble head group remains in the water phase. This alignment of surfactant molecules at the surface modifies the surface properties of water at the water/air or water/oil interface.

Examples of ionic surfactants include ionic surfactants such as anionic, cationic, or zwitterionic (ampoteric) surfactants. In some embodiments, a target object 58 is a reverse micelle or liposome.

In some embodiments, a target object 58 is a fullerene. A fullerene is any molecule composed entirely of carbon, in the form of a hollow sphere, ellipsoid or tube. Spherical fullerenes are also called buckyballs, and they resemble the balls used in association football. Cylindrical ones are called carbon nanotubes or buckytubes. Fullerenes are similar in structure to graphite, which is composed of stacked graphene sheets of linked hexagonal rings; but they may also contain pentagonal (or sometimes heptagonal) rings.

In some embodiments, a respective target object 58 in the first plurality of target objects is a polymer, and the posing the description of the test object 72 against the respective target object 58 comprises posing the description of the test object 58 against spatial coordinates for the respective target object in the form of a set of three-dimensional coordinates $\{x_1, \ldots, x_N\}$ for a crystal structure of the polymer resolved (e.g., by X-ray crystallographic techniques) at a resolution of 3.3 Å or better, 3.2 Å or better, 3.1 Å or better, 3.0 Å or better, 2.5 Å or better, 2.2 Å or better, 2.0 Å or better, 1.9 Å or better, 1.85 Å or better, 1.80 Å or better, 1.75 Å or better, or 1.70 Å or better (block 216).

In some embodiments, a respective target object 58 in the first plurality of target objects is a polymer, and the posing the description of the test object against the respective target object comprises posing the description of the test object of the target object against spatial coordinates for the respective target object in the form of an ensemble of ten or more, twenty or more or thirty or more three-dimensional coordinates for the polymer determined by nuclear magnetic resonance where the ensemble has a backbone RMSD of 1.0 Å or better, 0.9 Å or better, 0.8 Å or better, 0.7 Å or better, 0.6 Å or better, 0.5 Å or better, 0.4 Å or better, 0.3 Å or better, or 0.2 Å or better. In some embodiments the spatial coordinates are determined by neutron diffraction or cryo-electron microscopy (block 218).

In some embodiments, a target object 58 includes two different types of polymers, such as a nucleic acid bound to a polypeptide. In some embodiments, a target object 58 includes two polypeptides bound to each other. In some embodiments, a target object 58 includes one or more metal ions (e.g. a metalloproteinase with one or more zinc atoms). In such instances, the metal ions and or the organic small molecules may be included in the spatial coordinates 60 for the target object 58.

In some embodiments a target object 58 is a polymer and there are ten or more, twenty or more, thirty or more, fifty or more, one hundred or more, between one hundred and one thousand, or less than 500 residues in the polymer.

In some embodiments, the spatial coordinates 60 of a target object 58 are determined using modeling methods such as ab initio methods, density functional methods, semi-empirical and empirical methods, molecular mechanics, chemical dynamics, or molecular dynamics.

In an embodiment, the spatial coordinates 60 are represented by the Cartesian coordinates of the centers of the atoms comprising the target object. In some alternative embodiments, the spatial coordinates 60 for a target object 58 are represented by the electron density of the target object as measured, for example, by X-ray crystallography. For example, in some embodiments, the spatial coordinates 60 comprise a $2F_{observed}-F_{calculated}$ electron density map computed using the calculated atomic coordinates of a target object 58, where $F_{observed}$ is the observed structure factor amplitudes of the target object and Fc is the structure factor amplitudes calculated from the calculated atomic coordinates of the target object 58. Thus spatial coordinates 60 for a target object may be received as input data from a variety of sources, such as, but not limited to, structure ensembles generated by solution NMR, co-complexes as interpreted from X-ray crystallography, neutron diffraction, or cryo-electron microscopy, sampling from computational simulations, homology modeling or rotamer library sampling, and combinations of these techniques.

In some embodiments, each respective target object 72 in the first plurality of target objects is a polymer with an active site, the test object is a chemical composition, and the posing the description of the test object against the respective target object comprises docking an atomic representation of the test object into an atomic representation of the active site of the polymer (block 220). Nonlimiting examples of such docking are disclosed in Liu and Wang, 1999, "MCDOCK: A Monte Carlo simulation approach to the molecular docking problem," Journal of Computer-Aided Molecular Design 13, 435-451; Shoichet et al., 1992, "Molecular docking using shape descriptors," Journal of Computational Chemistry 13(3), pp. 380-397; Knegtel et al., 1997 "Molecular docking to ensembles of protein structures," Journal of Molecular Biology 266, pp. 424-440, Morris et al., 2009, "AutoDock4 and AutoDockTools4: Automated Docking with Selective Receptor Flexibility," J. Comput. Chem. 30(16), pp. 2785-2791; Sotriffer et al., 2000, "Automated docking of ligands to antibodies: methods and applications," Methods: A Companion to Methods in Enzymology 20, pp. 280-291; Morris et al., 1998, "Automated Docking Using a Lamarckian Genetic Algorithm and Empirical Binding Free Energy Function," Journal of Computational Chemistry 19: pp. 1639-1662; and Rarey et al., 1996, "A Fast Flexible Docking Method Using an Incremental Construction Algorithm," Journal of Molecular Biology 261, pp. 470-489, each of which is hereby incorporated by reference. In some such embodiments, the test object is a chemical compound, the respective target object comprises a polymer with a binding pocket, and the posing the description of the test object against the respective target object comprises docking modeled atomic coordinates for the chemical compound into atomic coordinates for the binding pocket (block 222).

In some embodiments, the first classifier 102 comprises a neural network or a support vector machine (block 224). See Duda et al., *Pattern Classification*, Second Edition, 2001, John Wiley & Sons, Inc., New York, Chapter 6, pp. 282-349, which is hereby incorporated by reference, for example disclosure on neural networks. See Duda et al., *Pattern Classification*, Second Edition, 2001, John Wiley & Sons, Inc., New York, pp. 259-265, which is hereby incorporated by reference, for example disclosure on support vector machines. In some embodiments, the first classifier 102 is a convolutional neural network. See Wallach et al., 2015, "AtomNet: A Deep Convolutional Neural Network for Bioactivity Prediction in Structure-based Drug Discovery," arXiv:1510.02855, which is hereby incorporated by reference.

Figure 2B:
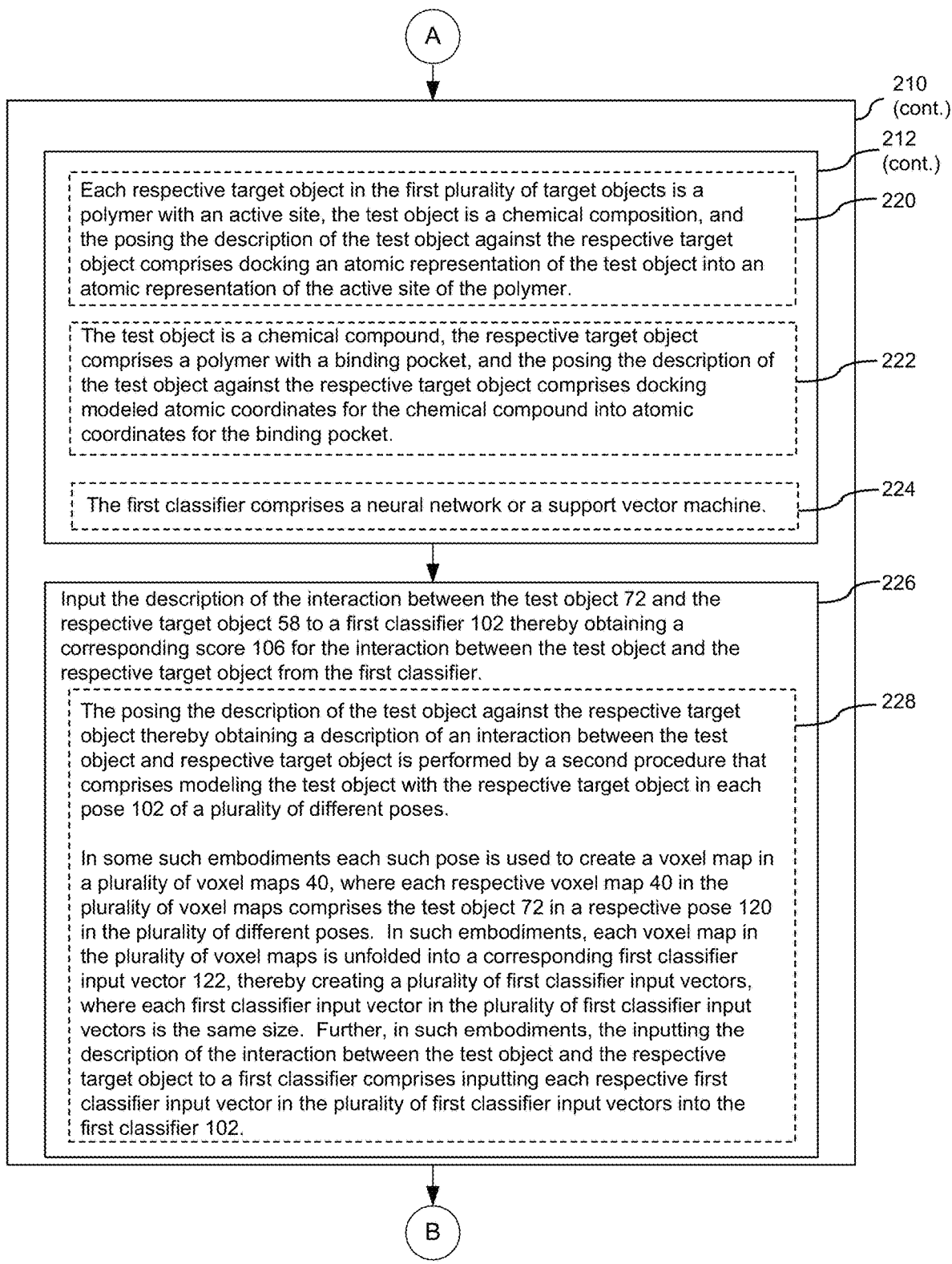

Referring to block 226 of FIG. 2B, once the description of the interaction between the test object 72 and the respective target object 58 has been made, it is inputted to the first classifier 102 thereby obtaining a corresponding score 106 for the interaction between the test object and the respective target object from the first classifier. In some embodiments, this score 106 is a scalar score, for instance a real number between 0 and 1. In some embodiments, the score 106 is a categorical score. For instance, in some embodiments, the score 106 is one of two possible values (e.g., "0" or "1"). In some embodiments, the score 106 is one of two possible categories ("not binding" or "binding"). In some embodiments, the score 106 is one of three possible categories ("not binding," "medium binding," and "strongly binding"). Any number of categories for the score 106 are contemplated and all such categories are with the scope of the present disclosure.

Referring to block 228 of FIG. 2B, in some embodiments, the posing the description of the test object 72 against the respective target object thereby obtaining a description of an interaction between the test object 72 and respective target object 58 is performed by a second procedure that comprises modeling the test object 72 with the respective target object 58 in each pose 102 of a plurality of different poses. In some embodiments, the target object 58 is a polymer with an active site, the test object 72 is a chemical compound, and the posing the description of the test object 72 against the respective target object 58 comprises docking the test object into the active site of the polymer.

In some embodiments, the interaction between a test object and a target object is determined by docking test object onto the target object 58 a plurality of times to form a plurality of poses. In some such embodiments, the test object 72 is docked onto the target object 58 twice, three times, four times, five or more times, ten or more times, fifty or more times, 100 or more times, or a 1000 or more times (block 232). Each such docking represents a different pose of the test object 72 onto the target object 58. In some embodiments, the target object 58 is a polymer with an active site and the test object 72 is docked into the active site in each of plurality of different ways, each such way representing a different pose. It is expected that many of these poses are not correct, meaning that such poses do not represent true interactions between the test object 72 and the target object 58 that arise in nature. In such embodiments, the first classifier is first trained using training objects 65, for which binding data 68 against the target object is known, in the same manner. That is, each training object 66 is docked against a target object a plurality of times and the interactions of the plurality of dockings is inputted into the first classifier to obtain a first classifier result. A differential between the first classifier result and the actual binding data 68 for the training object against the target object is used to refine the first classifier. Thus, advantageously, during training with the training objects 66, the first classifier 102 will be able to filter out (down weight) incorrect poses (incorrect dockings) because no consistent patterns will arise between the incorrect poses and the training object binding data. Without intending to be limited by any particular theory, it is expected that inter-object (e.g., intermolecular) interactions observed among incorrect poses will cancel each other out like white noise whereas the inter-object interactions formed by correct poses formed by training objects 66 will reinforce each other and thus train the weights of the network over time. Thus, during training mode regarding incorrect poses, the first classifier 102 would fail to find patterns which explain the difference between the active training objects 66 and the inactive training objects 66 (e.g., to discriminate between the binding data 68 of the training objects). With respect to incorrect poses, the first classifier 102 would learn the weight of the training objects 66, their size, and similar global summary descriptors, but none of the real intermolecular interactions that are formed between the training objects and the test object in nature. Thus, advantageously, the disclosed systems and methods are not sensitive to incorrect poses, particularly when more than 10 poses per training object 66, more than one hundred poses per training object 66, or more than one thousand poses per training object 66 are taken. Likewise, when a test object 72 is sampled, a plurality of poses is also taken in such embodiments. Thus, even within one test or training object, it is expected that the wrong poses will cancel each other out, and the poses that are close enough to imply something close to the kind of inter-object interactions (e.g., intermolecular bonding) that arises in nature, that such poses would be the ones that contribute to the final signal generated by the plurality of poses for a single test or training object.

In some embodiments, training objects 66 and test objects 72 are docked by either random pose generation techniques, or by biased pose generation.

In some embodiments, the plurality of different poses is obtained using a docking scoring function in one of a Markov chain Monte Carlo sampling, simulated annealing, a Lamarckian Genetic Algorithm, a genetic algorithm, or a deep convolutional neural net sampling (block 234). The plurality of different poses is obtained by incremental search using a greedy algorithm (block 236). For instance, in some embodiments, training objects 66 and/or test objects 72 are docked by Markov chain Monte Carlo sampling. In some embodiments, such sampling allows the full flexibility of training objects and/or test objects in the docking calculations and a scoring function that is the sum of the interaction energy between the training (or test) object and the target object 58 as well as the conformational energy of the training (or test) object. See, for example, Liu and Wang, 1999, "MCDOCK: A Monte Carlo simulation approach to the molecular docking problem," Journal of Computer-Aided Molecular Design 13, 435-451, which is hereby incorporated by reference. In some embodiments, algorithms such as DOCK (Shoichet, Bodian, and Kuntz, 1992, "Molecular docking using shape descriptors," Journal of Computational Chemistry 13(3), pp. 380-397; and Knegtel, Kuntz, and Oshiro, 1997 "Molecular docking to ensembles of protein structures," Journal of Molecular Biology 266, pp. 424-440, each of which is hereby incorporated by reference) are used to find a plurality of poses for the test object 72 against each of the target objects 58. Such algorithms model the target object and the test (or training) object as rigid bodies. The docked conformation is searched using surface complementary to find poses. In some embodiments, algorithms such as AutoDOCK (Morris et al., 2009, "AutoDock4 and AutoDockTools4: Automated Docking with Selective Receptor Flexibility," J. Comput. Chem. 30(16), pp. 2785-2791; Sotriffer et al., 2000, "Automated docking of ligands to antibodies: methods and applications," Methods: A Companion to Methods in Enzymology 20, pp. 280-291; and "Morris et al., 1998, "Automated Docking Using a Lamarckian Genetic Algorithm and Empirical Binding Free Energy Function," Journal of Computational Chemistry 19: pp. 1639-1662, each of which is hereby incorporated by reference) are used to find a plurality of poses for each of the test objects 72 and/or training objects 66 against each of the target objects 58. AutoDOCK uses a kinematic model of the ligand and supports Monte Carlo, simulated annealing, the Lamarckian Genetic Algorithm, and Genetic algorithms. Accordingly, in some embodiments the plurality of different poses (for a given test object-target object pair or a given training object-test object pair) are obtained by Markov chain Monte Carlo sampling, simulated annealing, Lamarckian Genetic Algorithms, or genetic algorithms, using a docking scoring function. In some embodiments, algorithms such as FlexX (Rarey et al., 1996, "A Fast Flexible Docking Method Using an Incremental Construction Algorithm," Journal of Molecular Biology 261, pp. 470-489, which is hereby incorporated by reference) are used to find a plurality of poses for each of the test objects 72 and/or training objects 66 against each of the target objects 58. FlexX does an incremental construction of the test object 72 and/or training object 66 at the active site of a target object 58 using a greedy algorithm. Accordingly, in some embodiments the plurality of different poses (for a given test object-target object pair or a given training object-test object pair) are obtained by a greedy algorithm.

In some embodiments, algorithms such as GOLD (Jones et al., 1997, "Development and Validation of a Genetic Algorithm for flexible Docking," Journal Molecular Biology 267, pp. 727-748, which is hereby incorporated by reference) are used to find a plurality of poses for each of the test objects 72 and/or training objects 66 against each of the target objects 58. GOLD stands for Genetic Optimization for Ligand Docking. GOLD builds a genetically optimized hydrogen bonding network between the test object 72 and/or training object 66 and the target object 58.

In some embodiments, the posing comprises performing a molecular dynamics run of the target object and the test object. During the molecular dynamics run, the atoms of the target object and the test object are allowed to interact for a fixed period of time, giving a view of the dynamical evolution of the system. The trajectory of atoms in the target object and the test object (or training object) are determined by numerically solving Newton's equations of motion for a system of interacting particles, where forces between the particles and their potential energies are calculated using interatomic potentials or molecular mechanics force fields. See Alder and Wainwright, 1959, "Studies in Molecular Dynamics. I. General Method,". J. Chem. Phys. 31 (2): 459; Bibcode, 1959, J. Ch. Ph. 31, 459A, doi:10.1063/1.1730376, and Brooks, 1983, "CHARMM: A program for Macromolecular Energy, Minimization, and Dynamics Calculations," Journal of Computational Chemistry 4, 187-217, each of which is hereby incorporated by reference. Thus, in this way, the molecular dynamics run produces a trajectory of the target object and the test object together over time. This trajectory comprises the trajectory of the atoms in the target object and the test object. In some embodiments, a subset of the plurality of different poses is obtained by taking snapshots of this trajectory over a period of time.

In some embodiments, poses are obtained from snapshots of several different trajectories, where each trajectory comprise a different molecular dynamics run of the target object interacting with the test object. In some embodiments, prior to a molecular dynamics run, a test object (or a training object) is first docketed into an active site of a target object using a docking technique.

Regardless of what modeling method is used, what is achieved for any given test object 72/training object 66-target object 58 pair is a diverse set of poses of the test/training object with the target object with the expectation that one or more of the poses is close enough to the naturally occurring pose to demonstrate some of the relevant intermolecular interactions between the given test object 72/training object 66-target object 58 pair.

Figure 3:
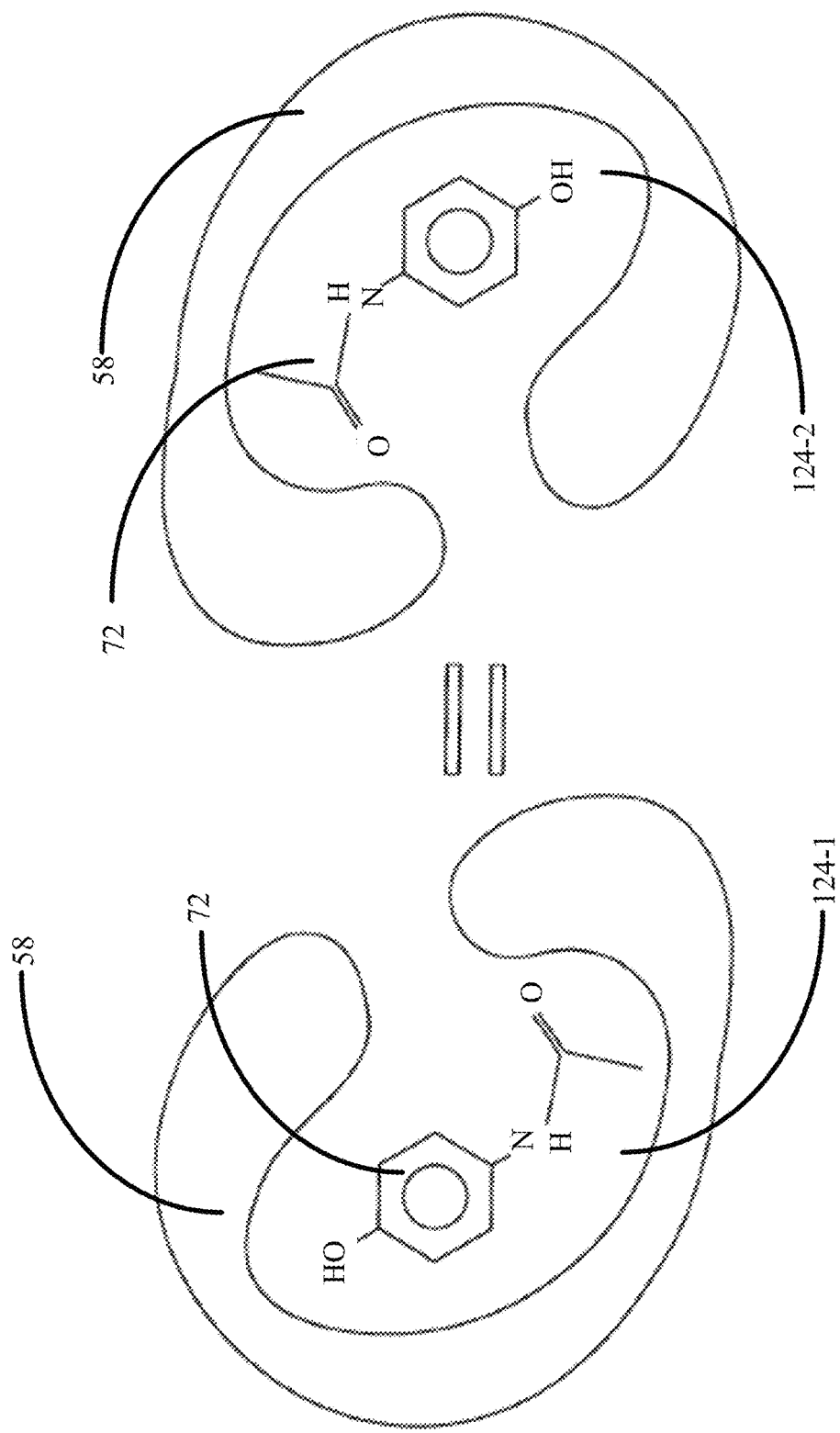
FIG. 3 is a schematic view of an example test object in two different poses relative to a target object, according to an embodiment.

In some embodiments an initial pose of the test object or training object in the active site of a target object 58 is generated using any of the above-described techniques and additional poses are generated through the application of some combination of rotation, translation, and mirroring operators in any combination of the three X, Y and Z planes. Rotation and translation of the test or training object may be randomly selected (within some range, e.g. plus or minus 5 Å from the origin) or uniformly generated at some pre-specified increment (e.g., all 5 degree increments around the circle). FIG. 3 provides a sample illustration of a test object 72 in two different poses 302 in the active site of a target object 58.

Continuing to refer to block 228 of FIG. 2B, in some embodiments, each such pose is used to create a voxel map 40, thereby creating a plurality of voxel maps, where each respective voxel map 40 in the plurality of voxel maps comprises the test object 72 in a respective pose 120 in the plurality of different poses. In some embodiments, each respective voxel map 40 in the plurality of voxel maps is created by a method comprising: (i) sampling the test object 72 (or training object 68), in a respective pose in the plurality of different poses, and the target object 58 on a three-dimensional grid basis thereby forming a corresponding three dimensional uniform space-filling honeycomb comprising a corresponding plurality of space filling (three-dimensional) polyhedral cells and (ii) populating, for each respective three-dimensional polyhedral cell in the corresponding plurality of three-dimensional cells, a voxel (discrete set of regularly-spaced polyhedral cells) in the respective voxel map 40 based upon a property (e.g., chemical property) of the respective three-dimensional polyhedral cell. Thus, if a particular test object has ten poses relative to a target object, ten corresponding voxel maps are created, if a particular test object has one hundred poses relative to a target object, one hundred corresponding voxel maps are created, and so forth. Examples of space filling honeycombs include cubic honeycombs with parallelepiped cells, hexagonal prismatic honeycombs with hexagonal prism cells, rhombic dodecahedra with rhombic dodecahedron cells, elongated dodecahedra with elongated dodecahedron cells, and truncated octahedra with truncated octahedron cells.

In some embodiments, the space filling honeycomb is a cubic honeycomb with cubic cells and the dimensions of such voxels determine their resolution. For example, a resolution of 1 Å may be chosen meaning that each voxel, in such embodiments, represents a corresponding cube of the geometric data with 1 Å dimensions (e.g., 1 Å×1 Å×1 Å in the respective height, width, and depth of the respective cells). However, in some embodiments, finer grid spacing (e.g., 0.1 Å or even 0.01 Å) or coarser grid spacing (e.g. 4 Å) is used, where the spacing yields an integer number of voxels to cover the input geometric data. In some embodiments, the sampling occurs at a resolution that is between 0.1 Å and 10 Å (227). As an illustration, for a 40 Å input cube, with a 1 Å resolution, such an arrangement would yield 40*40 * 40=64,000 input voxels.

In some embodiments, the test object 72 (or training object 66) is a first compound and the target object 58 is a second compound, a characteristic of an atom incurred in the sampling (i) is placed in a single voxel in the respective voxel map by the populating (ii), and each voxel in the plurality of voxels represents a characteristic of a maximum of one atom. In some embodiments, the characteristic of the atom consists of an enumeration of the atom type. As one example, for biological data, some embodiments of the disclosed systems and methods are configured to represent the presence of every atom in a given voxel of the voxel map 40 as a different number for that entry, e.g., if a carbon is in a voxel, a value of 6 is assigned to that voxel because the atomic number of carbon is 6. However, such an encoding could imply that atoms with close atomic numbers will behave similarly, which may not be particularly useful depending on the application. Further, element behavior may be more similar within groups (columns on the periodic table), and therefore such an encoding poses additional work for the first classifier to decode.

In some embodiments, the characteristic of the atom is encoded in the voxel as a binary categorical variable. In such embodiments, atom types are encoded in what is termed a "one-hot" encoding: every atom type has a separate channel. Thus, in such embodiments, each voxel has a plurality of channels and at least a subset of the plurality of channels represent atom types. For example, one channel within each voxel may represent carbon whereas another channel within each voxel may represent oxygen. When a given atom type is found in the three-dimensional grid element corresponding to a given voxel, the channel for that atom type within the given voxel is assigned a first value of the binary categorical variable, such as "1", and when the atom type is not found in the three-dimensional grid element corresponding to the given voxel, the channel for that atom type is assigned a second value of the binary categorical variable, such as "0" within the given voxel.

While there are over 100 elements, most are not encountered in biology. However, even representing the most common biological elements (i.e., H, C, N, O, F, P, S, Cl, Br, I, Li, Na, Mg, K, Ca, Mn, Fe, Co, Zn) may yield 18 channels per voxel or 10,483*18=188,694 inputs to the receptor field. As such, in some embodiments, each respective voxel in a voxel map 40 in the plurality of voxel maps comprises a plurality of channels, and each channel in the plurality of channels represents a different property that may arise in the three-dimensional space filling polyhedral cell corresponding to the respective voxel. The number of possible channels for a given voxel is even higher in those embodiments where additional characteristics of the atoms (for example, partial charge, presence in ligand versus protein target, electronegativity, or SYBYL atom type) are additionally presented as independent channels for each voxel, necessitating more input channels to differentiate between otherwise-equivalent atoms.

In some embodiments, each voxel has five or more input channels. In some embodiments, each voxel has fifteen or more input channels. In some embodiments, each voxel has twenty or more input channels, twenty-five or more input channels, thirty or more input channels, fifty or more input channels, or one hundred or more input channels. In some embodiments, each voxel has five or more input channels selected from the descriptors found in Table 1 below. For example, in some embodiments, each voxel has five or more channels, each encoded as a binary categorical variable where each such channel represents a SYBYL atom type selected from Table 1 below. For instance, in some embodiments, each respective voxel in a voxel map 40 includes a channel for the C.3 (sp3 carbon) atom type meaning that if the grid in space for a given test object-target object (or training object-target object) complex represented by the respective voxel encompasses an sp3 carbon, the channel adopts a first value (e.g., "1") and is a second value (e.g. "0") otherwise.

TABLE 1

| SYBYL Atom Types | |
|---|---|
| SYBYL ATOM TYPE | DESCRIPTION |
| C.3 | sp3 carbon |
| C.2 | sp2 carbon |
| C.ar | aromatic carbon |
| C.1 | sp carbon |
| N.3 | sp3 nitrogen |
| N.2 | sp2 nitrogen |
| N.1 | sp nitrogen |
| O.3 | sp3 oxygen |
| O.2 | sp2 oxygen |
| S.3 | sp3 sulfur |
| N.ar | aromatic nitrogen |
| P.3 | sp3 phosphorous |
| H | hydrogen |
| Br | bromine |
| Cl | chlorine |
| F | fluorine |
| I | iodine |
| S.2 | sp2 sulfur |
| N.pl3 | pl3 trigonal planar nitrogen |
| LP | lone pair |
| Na | sodium |
| K | potassium |
| Ca | calcium |
| Li | lithium |
| Al aluminum | aluminum |
| Si | silicon |
| N.am | amide nitrogen |
| S.o | sulfoxide sulfur |
| S.o2 | sulfone sulfur |
| N.4 | positively charged nitrogen |
| O.co2 | oxygen in carboxylate or phosphate group |
| C.cat | carbocation, used only in a guadinium group |

TABLE 1-continued

| SYBYL Atom Types | |
|---|---|
| SYBYL ATOM TYPE | DESCRIPTION |
| H.spc | hydrogen in SPC water model |
| O.spc | oxygen in SPC water model |
| H.t3p | hydrogen in TIP3P water model |
| O.t3p | oxygen in TIP3P water model |
| ANY | any atom |
| HEV | heavy (non H) atom |
| HET | heteroatom (N, O, S, P) |
| HAL | halogen |
| Mg | magnesium |
| Cr.oh | hydroxy chromium |
| Cr.th | chromium |
| Se | selenium |
| Fe | iron |
| Cu | copper |
| Zn | zinc |
| Sn | tin |
| Mo | molybdenum |
| Mn | manganese |
| Co.oh | hydroxy cobalt |

In some embodiments, each voxel comprises ten or more input channels, fifteen or more input channels, or twenty or more input channels selected from the descriptors found in Table 1 above. In some embodiments, each voxel includes a channel for halogens.

In some embodiments, a structural protein-ligand interaction fingerprint (SPLIF) score is generated for each pose of a given test object (or training object) to a target object and this SPLIF score is used as additional input into the underlying neural network or is individually encoded in the voxel map. For a description of SPLIFs, see Da and Kireev, 2014, J. Chem. Inf. Model. 54, pp. 2555-2561, "Structural Protein-Ligand Interaction Fingerprints (SPLIF) for Structure-Based Virtual Screening: Method and Benchmark Study," which is hereby incorporated by reference. A SPLIF implicitly encodes all possible interaction types that may occur between interacting fragments of the test (or training) object and the target object (e.g., π-π, CH-π, etc.). In the first step, a test (or training) object-target object complex (pose) is inspected for intermolecular contacts. Two atoms are deemed to be in a contact if the distance between them is within a specified threshold (e.g., within 4.5 Å). For each such intermolecular atom pair, the respective test (or training) atom and target object atoms are expanded to circular fragments, e.g., fragments that include the atoms in question and their successive neighborhoods up to a certain distance. Each type of circular fragment is assigned an identifier. In some embodiments, such identifiers are coded in individual channels in the respective voxels. In some embodiments, the Extended Connectivity Fingerprints up to the first closest neighbor (ECFP2) as defined in the Pipeline Pilot software can be used. See, Pipeline Pilot, ver. 8.5, Accelrys Software Inc., 2009, which is hereby incorporated by reference. ECFP retains information about all atom/bond types and uses one unique integer identifier to represent one substructure (i.e., circular fragment). The SPLIF fingerprint encodes all the circular fragment identifiers found. In some embodiments, the SPLIF fingerprint is not encoded individual voxels but serves as a separate independent input in the first classifier discussed below.

In some embodiments, rather than or in addition to SPLIFs, structural interaction fingerprints (SIFt) are computed for each pose of a given test object (or training object) to a target object and independently provided as input into the first classifier discussed below or are encoded in the voxel map. For a computation of SIFts, see Deng et al., 2003, "Structural Interaction Fingerprint (SIFt): A Novel Method for Analyzing Three-Dimensional Protein-Ligand Binding Interactions," J. Med. Chem. 47 (2), pp. 337-344, which is hereby incorporated by reference.

In some embodiments, rather than or in addition to SPLIFs and SIFTs, atom-pairs-based interaction fragments (APIFs) are computed for each pose of a given test object (or training object) to a target object and independently provided as input into the first classifier or is individually encoded in the voxel map. For a computation of APIFs, see Perez-Nueno et al., 2009, "APIF: a new interaction fingerprint based on atom pairs and its application to virtual screening," J. Chem. Inf. Model. 49(5), pp. 1245-1260, which is hereby incorporated by reference.

Figure 4:
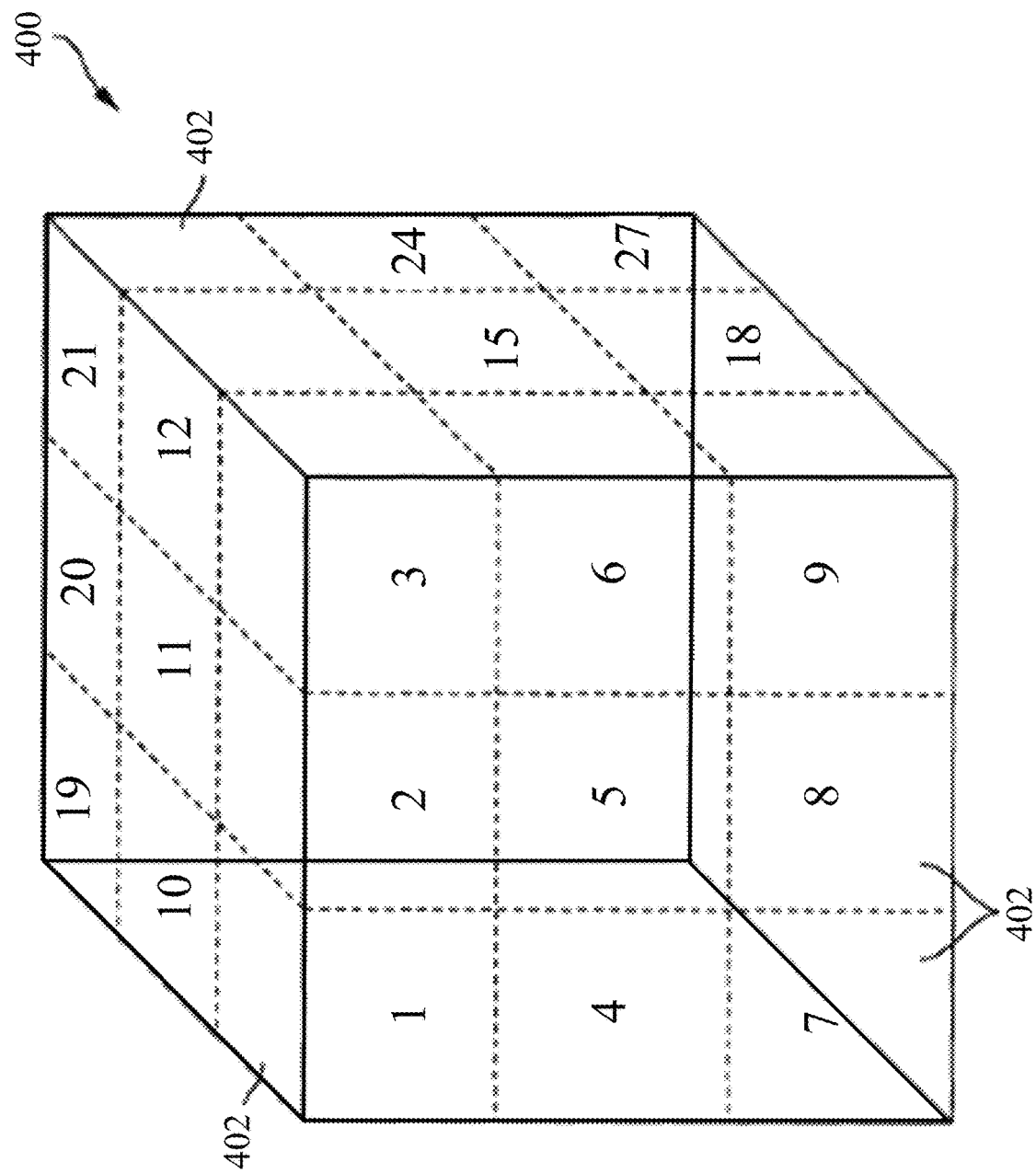
FIG. 4 is a schematic view of a geometric representation of input features in the form of a three-dimensional grid of voxels (voxel map), according to an embodiment.

The data representation may be encoded with the biological data in a way that enables the expression of various structural relationships associated with molecules/proteins for example. The geometric representation may be implemented in a variety of ways and topographies, according to various embodiments. The geometric representation is used for the visualization and analysis of data. For example, in an embodiment, geometries may be represented using voxels laid out on various topographies, such as 2-D, 3-D Cartesian/Euclidean space, 3-D non-Euclidean space, manifolds, etc. For example, FIG. 4 illustrates a sample three-dimensional grid structure 400 including a series of sub-containers, according to an embodiment. Each sub-container 402 may correspond to a voxel. A coordinate system may be defined for the grid, such that each sub-container has an identifier. In some embodiments of the disclosed systems and methods, the coordinate system is a Cartesian system in 3-D space, but in other embodiments of the system, the coordinate system may be any other type of coordinate system, such as an oblate spheroid, cylindrical or spherical coordinate systems, polar coordinates systems, other coordinate systems designed for various manifolds and vector spaces, among others. In some embodiments, the voxels may have particular values associated to them, which may, for example, be represented by applying labels, and/or determining their positioning, among others.

Because some forms of first classifiers 102, such as neural networks, require a fixed input size, some embodiments of the disclosed systems and methods crop the geometric data (the target-test or target-training object complex) to fit within an appropriate bounding box. For example, a cube of 25-40 Å to a side, may be used. In some embodiments in which the target and/or test objects have been docketed into the active site of target objects 58, the center of the active site serves as the center of the cube.

While in some embodiments a square cube of fixed dimensions centered on the active site of the target object is used to partition the space into the voxel grid, the disclosed systems are not so limited. In some embodiments, any of a variety of shapes is used to partition the space into the voxel grid. In some embodiments, polyhedra, such as rectangular prisms, polyhedra shapes, etc. are used to partition the space.

In an embodiment, the grid structure may be configured to be similar to an arrangement of voxels. For example, each sub-structure may be associated with a channel for each atom being analyzed. Also, an encoding method may be provided for representing each atom numerically.

In some embodiments, the voxel map takes into account the factor of time and may thus be in four dimensions (X, Y, Z, and time).

In some embodiments, other implementations such as pixels, points, polygonal shapes, polyhedrals, or any other type of shape in multiple dimensions (e.g. shapes in 3D, 4D, and so on) may be used instead of voxels.

In some embodiments, the geometric data is normalized by choosing the origin of the X, Y and Z coordinates to be the center of mass of a binding site of the target object as determined by a cavity flooding algorithm. For representative details of such algorithms, see Ho and Marshall, 1990, "Cavity search: An algorithm for the isolation and display of cavity-like binding regions," Journal of Computer-Aided Molecular Design 4, pp. 337-354; and Hendlich et al., 1997, "Ligsite: automatic and efficient detection of potential small molecule-binding sites in proteins," J. Mol. Graph. Model 15, no. 6, each of which is hereby incorporated by reference. Alternatively, in some embodiments, the origin of the voxel map is centered at the center of mass of the entire co-complex (of the test object bound to the target object or training object bound to the target object, of just the target object, or of just the test objector training object). The basis vectors may optionally be chosen to be the principal moments of inertia of the entire co-complex, of just the target, or of just the test object/training object. In some embodiments, the target object 58 is a polymer having an active site, and the sampling samples the test object 72 (or training object 66), in each of the respective poses in the plurality of different poses for the test object 72 (or training object 66), and the active site on the three-dimensional grid basis in which a center of mass of the active site is taken as the origin and the corresponding three dimensional uniform honeycomb for the sampling represents a portion of the polymer and the test object 72 (or training object 66) centered on the center of mass. In some embodiments, the uniform honeycomb is a regular cubic honeycomb and the portion of the polymer and the test object is a cube of predetermined fixed dimensions. Use of a cube of predetermined fixed dimensions, in such embodiments, ensures that a relevant portion of the geometric data is used and that each voxel map is the same size. In some embodiments, the predetermined fixed dimensions of the cube are N Å×N Å×N Å, where N is an integer or real value between 5 and 100, an integer between 8 and 50, or an integer between 15 and 40. In some embodiments, the uniform honeycomb is a rectangular prism honeycomb and the portion of the polymer and the test object is a rectangular prism predetermined fixed dimensions Q Å×R Å×S Å, wherein Q is a first integer between 5 and 100, R is a second integer between 5 and 100, S is a third integer or real value between 5 and 100, and at least one number in the set {Q, R, S} is not equal to another value in the set {Q, R, S}.

In an embodiment, every voxel has one or more input channels, which may have various values associated with them, which in a simple implementation could be on/off, and may be configured to encode for a type of atom. Atom types may denote the element of the atom, or atom types may be further refined to distinguish between other atom characteristics. Atoms present may then be encoded in each voxel. Various types of encoding may be utilized using various techniques and/or methodologies. As an example encoding method, the atomic number of the atom may be utilized, yielding one value per voxel ranging from one for hydrogen to 118 for ununoctium (or any other element).

However, as discussed above, other encoding methods may be utilized, such as "one-hot encoding," where every voxel has many parallel input channels, each of which is either on or off and encodes for a type of atom. Atom types may denote the element of the atom, or atom types may be further refined to distinguish between other atom characteristics. For example, SYBYL atom types distinguish singlebonded carbons from double-bonded, triple-bonded, or aromatic carbons. For SYBYL atom types, see Clark et al., 1989, "Validation of the General Purpose Tripos Force Field, 1989, J. Comput. Chem. 10, pp. 982-1012, which is hereby incorporated by reference.

In some embodiments, each voxel further includes one or more channels to distinguish between atoms that are part of the target object 58 or cofactors versus part of the test object 72 or training object 66. For example, in one embodiment, each voxel further includes a first channel for the target object 58 and a second channel for the test object 72 or training object 66 (238). When an atom in the portion of space represented by the voxel is from the target object 58, the first channel is set to a value, such as "1", and is zero otherwise (e.g., because the portion of space represented by the voxel includes no atoms or one or more atoms from the test object 72 or training object 66). Further, when an atom in the portion of space represented by the voxel is from the test object 72 or training object 66, the second channel is set to a value, such as "1", and is zero otherwise (e.g., because the portion of space represented by the voxel includes no atoms or one or more atoms from the target object 58). Likewise, other channels may additionally (or alternatively) specify further information such as partial charge, polarizability, electronegativity, solvent accessible space, and electron density. For example, in some embodiments, an electron density map for the target object overlays the set of three-dimensional coordinates, and the creation of the voxel map further samples the electron density map. Examples of suitable electron density maps include, but are not limited to, multiple isomorphous replacement maps, single isomorphous replacement with anomalous signal maps, single wavelength anomalous dispersion maps, multi-wavelength anomalous dispersion maps, and 2Fo-Fc maps (260). See McRee, 1993, *Practical Protein Crystallography*, Academic Press, which is hereby incorporated by reference.

In some embodiments, voxel encoding in accordance with the disclosed systems and methods may include additional optional encoding refinements. The following two are provided as examples.

In a first encoding refinement, the required memory may be reduced by reducing the set of atoms represented by a voxel (e.g., by reducing the number of channels represented by a voxel) on the basis that most elements rarely occur in biological systems. Atoms may be mapped to share the same channel in a voxel, either by combining rare atoms (which may therefore rarely impact the performance of the system) or by combining atoms with similar properties (which therefore could minimize the inaccuracy from the combination).

An encoding refinement is to have voxels represent atom positions by partially activating neighboring voxels. This results in partial activation of neighboring neurons in the subsequent neural network and moves away from one-hot encoding to a "several-warm" encoding. For example, it may be illustrative to consider a chlorine atom, which has a van der Waals diameter of 3.5 Å and therefore a volume of 22.4 Å$^3$ when a 1 Å$^3$ grid is placed, voxels inside the chlorine atom will be completely filled and voxels on the edge of the atom will only be partially filled. Thus, the channel representing chlorine in the partially-filled voxels will be turned on proportionate to the amount such voxels fall inside the chlorine atom. For instance, if fifty percent of the voxel volume falls within the chlorine atom, the channel in the voxel representing chlorine will be activated fifty percent. This may result in a "smoothed" and more accurate representation relative to the discrete one-hot encoding.

Thus, in some embodiments, the test object is a first compound and the target object is a second compound, a characteristic of an atom incurred in the sampling is spread across a subset of voxels in the respective voxel map 40 and this subset of voxels comprises two or more voxels, three or more voxels, five or more voxels, ten or more voxels, or twenty-five or more voxels. In some embodiments, the characteristic of the atom consists of an enumeration of the atom type (e.g., one of the SYBYL atom types).

Thus, voxelation (rasterization) of the geometric data (the docking of a test or training object onto a target object) that has been encoded is based upon various rules applied to the input data.

Figure 5:
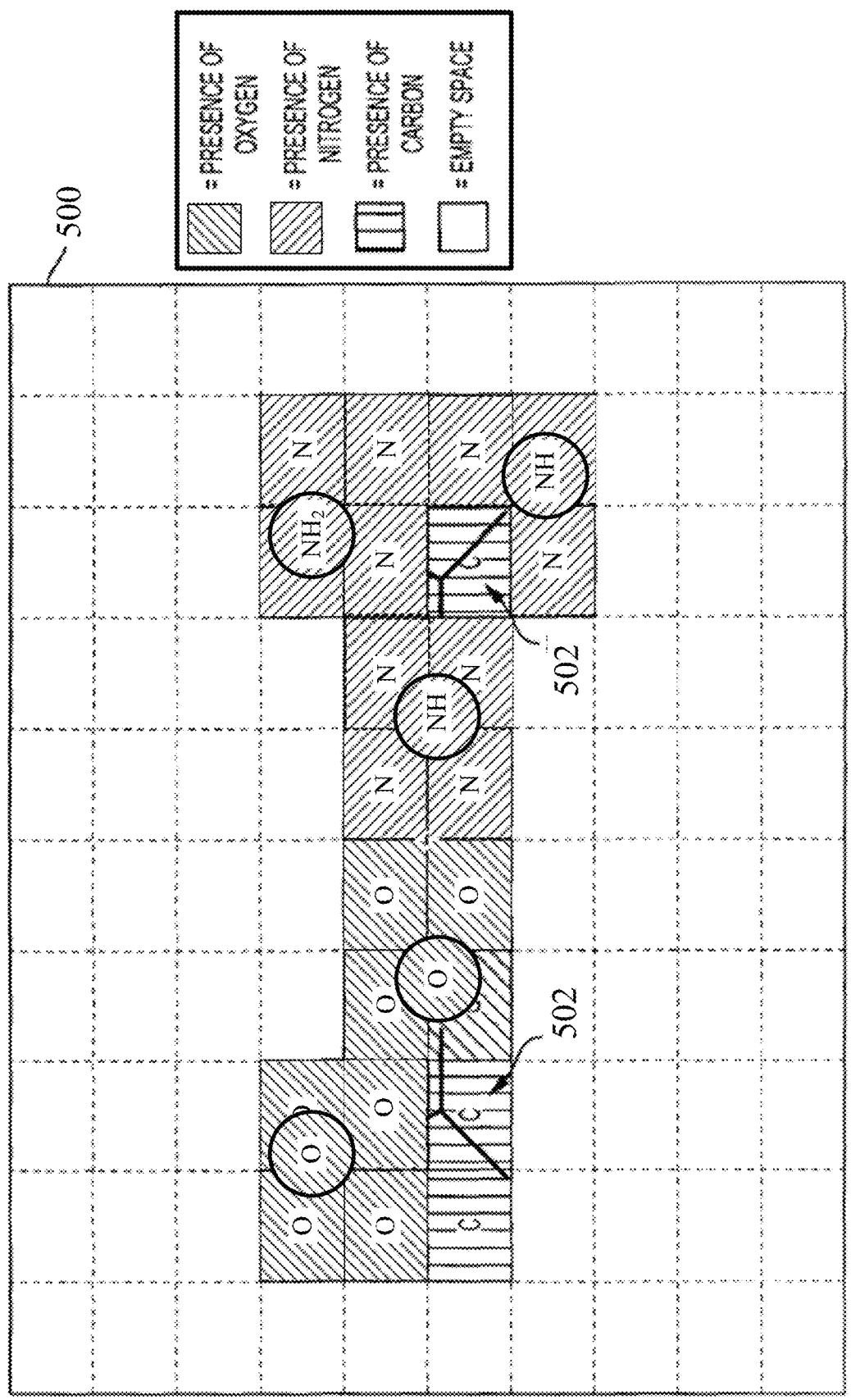
FIG. 5 and FIG. 6 are views of two objects encoded onto a two dimensional grid of voxels, according to an embodiment.
Figure 6:
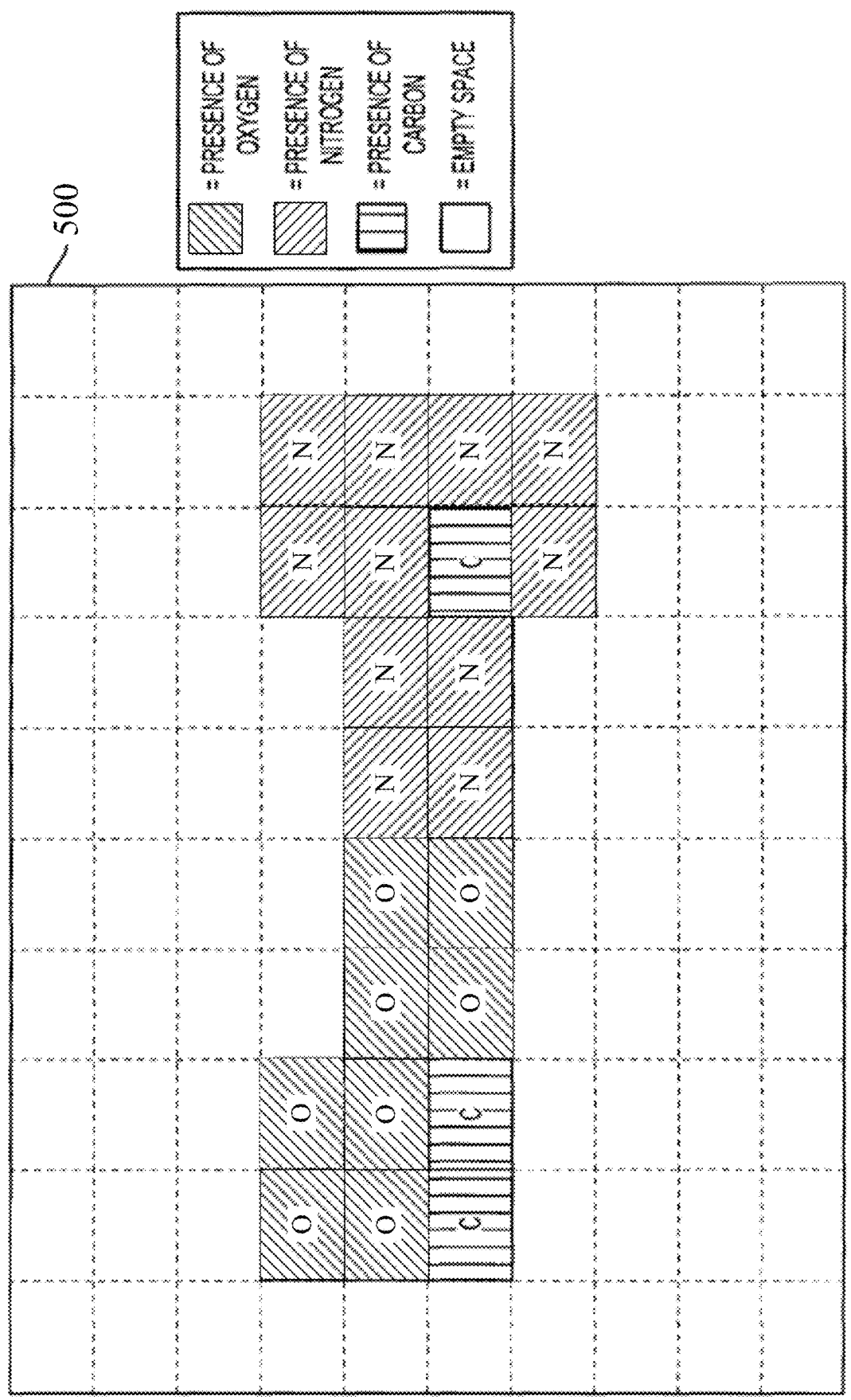
Figure 7:
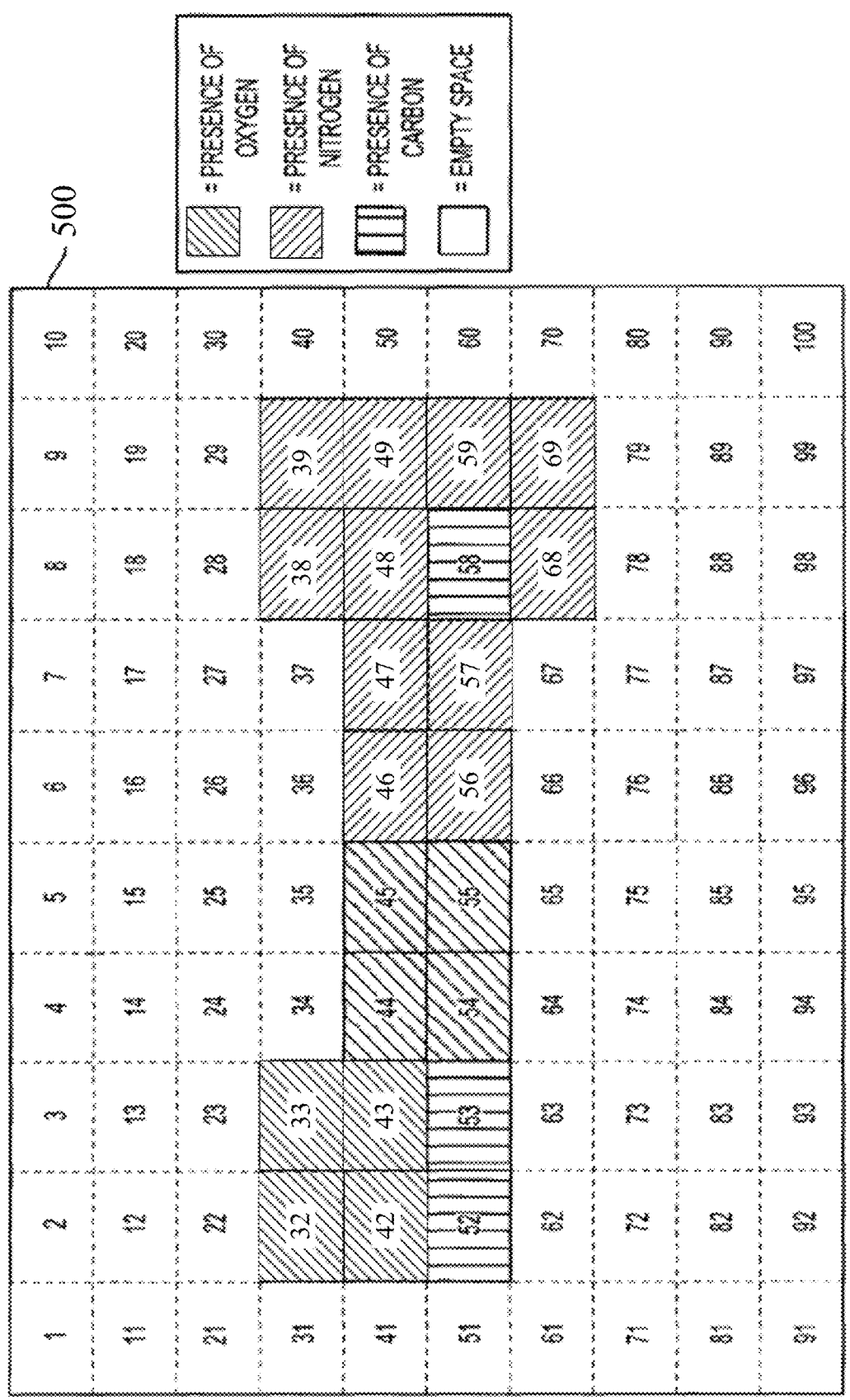
FIG. 7 is the view of the visualization of FIG. 6, in which the voxels have been numbered, according to an embodiment.

FIG. 5 and FIG. 6 provide views of two molecules 502 encoded onto a two dimensional grid 500 of voxels, according to some embodiments. FIG. 5 provides the two molecules superimposed on the two dimensional grid. FIG. 6 provides the one-hot encoding, using the different shading patterns to respectively encode the presence of oxygen, nitrogen, carbon, and empty space. As noted above, such encoding may be referred to as "one-hot" encoding. FIG. 6 shows the grid 500 of FIG. 5 with the molecules 502 omitted. FIG. 7 provides a view of the two dimensional grid of voxels of FIG. 6, where the voxels have been numbered.

Figure 8:
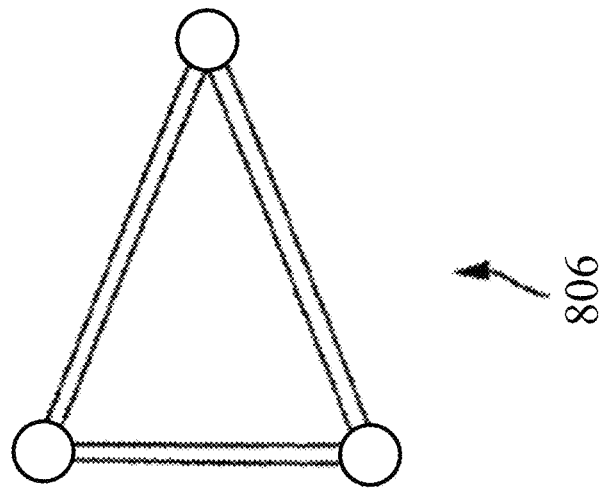
FIG. 8 is a schematic view of geometric representation of input features in the form of coordinate locations of atom centers, according to an embodiment.
Figure 8:
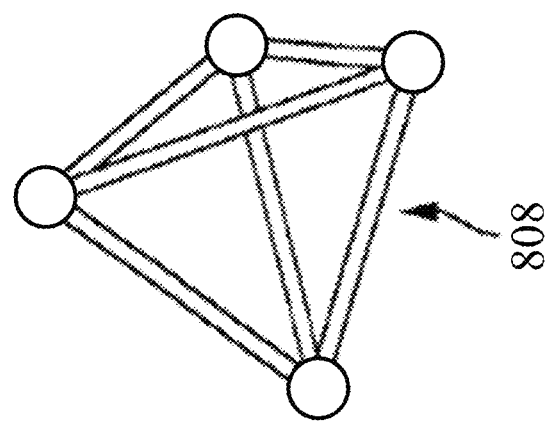
Figure 8:
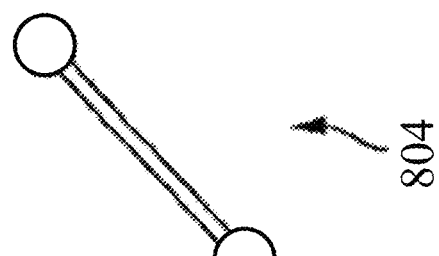
Figure 8:
Figure 9:
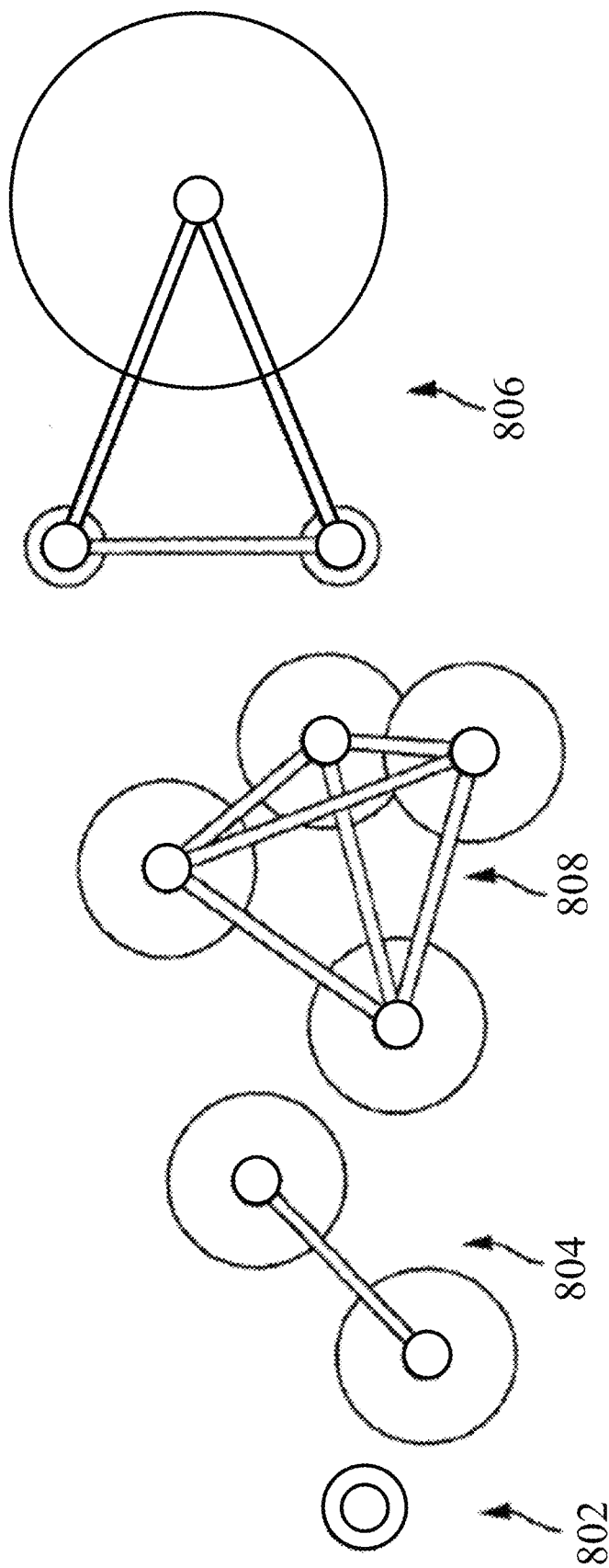
FIG. 9 is schematic view of the coordinate locations of FIG. 8 with a range of locations, according to an embodiment.

In some embodiments, feature geometry is represented in forms other than voxels. FIG. 8 provides view of various representations in which features (e.g., atom centers) are represented as 0-D points (representation 802), 1-D points (representation 804), 2-D points (representation 806), or 3-D points (representation 808). Initially, the spacing between the points may be randomly chosen. However, as the predictive model is trained, the points may be moved closer together, or father apart. FIG. 9 illustrates a range of possible positions for each point.

Referring again to block 228 of FIG. 2B, in some embodiments in which voxel maps are created, each voxel map in the plurality of voxel maps is unfolded into a corresponding first classifier input vector 122, thereby creating a plurality of first classifier input vectors. In some embodiments, each first classifier input vector 122 in the plurality of first classifier input vectors is one-dimensional (block 230). In other words, in some embodiments, each vector in the plurality of vectors is a one-dimensional vector. For instance, in some embodiments, a cube of 20 Å on each side is centered on the active site of the target object 58 and is sampled with a three-dimensional fixed grid spacing of 1 Å to form corresponding voxels of a voxel map that hold in respective channels basic of the voxel structural features such as atom types as well as, optionally, more complex test object-target object descriptors, as discussed above. In some embodiments, the voxels of this three-dimensional voxel map are unfolded into a one-dimensional floating point vector.

In some embodiments, the voxel maps are not vectorized before being input into a first classifier 102.

In some such embodiments, each first classifier input vector in the plurality of first classifier input vectors is the same size. In such embodiments, the inputting the description of the interaction between the test object and the respective target object to a first classifier comprises inputting each respective first classifier input vector in the plurality of first classifier input vectors into the first classifier 102.

Figure 2C:
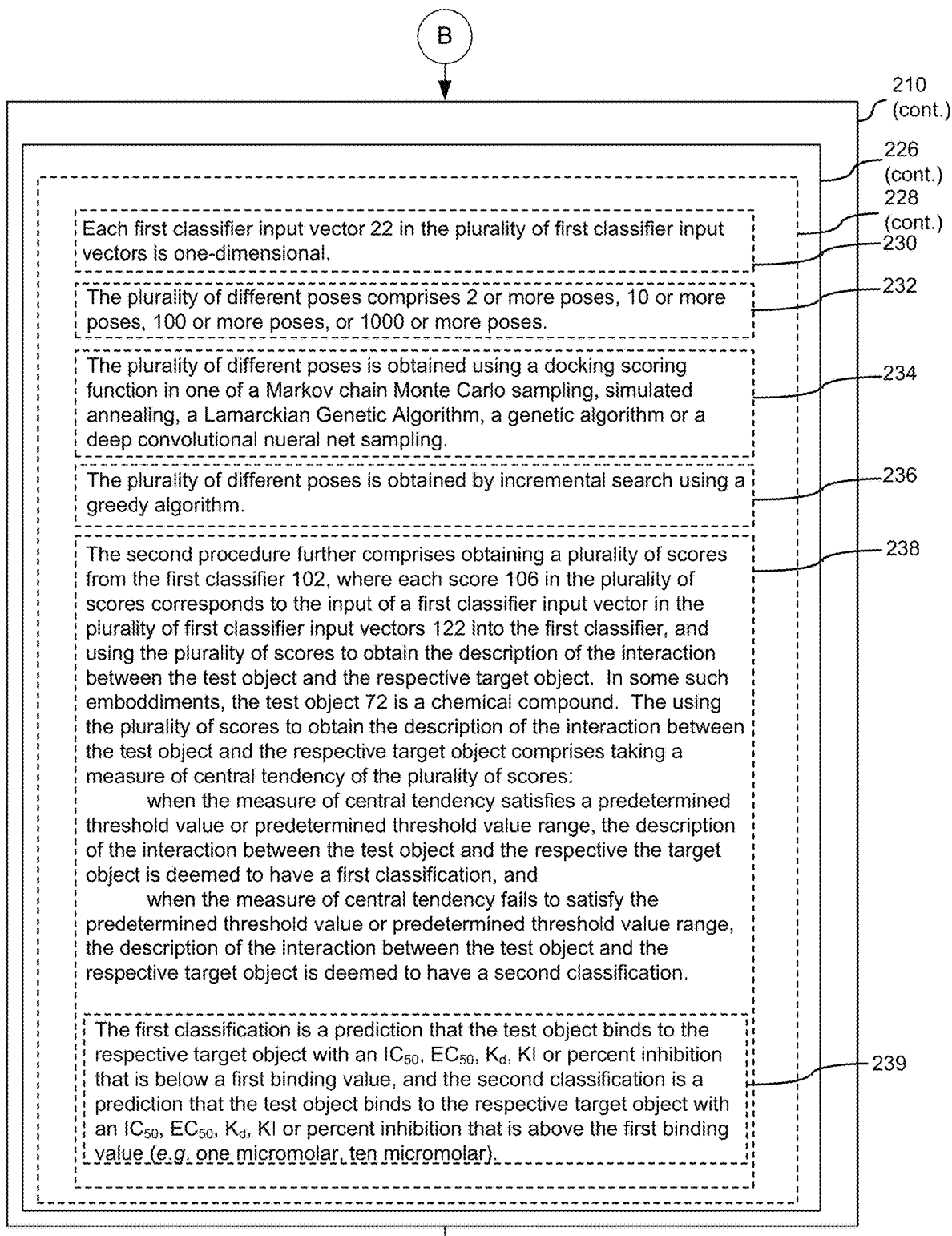

Referring to block 238 of FIG. 2C, when a plurality of poses is sampled for a given test object 72, the second procedure of block 228 further comprises obtaining a plurality of scores from the first classifier 102, where each score 106 in the plurality of scores corresponds to the input of a first classifier input vector in the plurality of first classifier input vectors 122 into the first classifier. This plurality of scores is used to obtain the description of the interaction between the test object 72 and the respective target object 58. In some such embodiments, the test object 72 is a chemical compound.

In some embodiments the plurality of scores is used to obtain the description of the interaction between the test object and the respective target object by taking a measure of central tendency (e.g., an arithmetic mean, weighted mean, midrange, midhinge, trimean, Winsorized mean, median, or mode of the remaining filtered signal measurements in the plurality of filtered signal measurements) of the plurality of scores. In some such embodiments, when the measure of central tendency satisfies a predetermined threshold value or predetermined threshold value range, the description of the interaction between the test object and the respective the target object is deemed to have a first classification. When the measure of central tendency fails to satisfy the predetermined threshold value or predetermined threshold value range, the description of the interaction between the test object and the respective target object is deemed to have a second classification. In some embodiments, the first classification is a prediction that the test object binds to the respective target object with an $IC_{50}$, $EC_{50}$, $K_d$, KI, or percent inhibition that is below a first binding value, and the second classification is a prediction that the test object binds to the respective target object with an $IC_{50}$, $EC_{50}$, $K_d$, KI, or percent inhibition that is above the first binding value (e.g. one nanomolar, ten nanomolar, one hundred nanomolar, one micromolar, ten micromolar, one hundred micromolar, or one millimolar) (block 239). In some such embodiments, the measure of central tendency is not classified and is ultimately passed on to the second classifier in the form of an element (score 106) in a test vector 104. In embodiments, the measure of central tendency is classified and this classification, as opposed to the raw score from the first classifier 102 is ultimately passed on to the second classifier in the form of an element (score 106) in a test vector 104.

In an embodiment where the first classifier has numerous outputs, such as some convolutional neural networks, the outputs may be combined using any of the activation functions described herein are that are known or developed. Examples include, but are not limited to, a non-saturating activation function $f(x)=\max(0,x)$, a saturating hyperbolic tangent function $f(x)=\tan h$, $f(x)=|\tan h(x)|$, the sigmoid function $f(x)=(1+e^{-x})^{-1}$, logistic (or sigmoid), softmax, Gaussian, Boltzmann-weighted averaging, absolute value, linear, rectified linear, bounded rectified linear, soft rectified linear, parameterized rectified linear, average, max, min, some vector norm LP (for $p=1, 2, 3, \ldots, \infty$), sign, square, square root, multiquadric, inverse quadratic, inverse multiquadric, polyharmonic spline, and thin plate spline. In some embodiments of the present disclosure, a Boltzmann distribution is utilized to combine outputs, as this matches the physical probability of poses if the outputs are interpreted as indicative of binding energies. In other embodiments of the invention, the max( ) function may also provide a reasonable approximation to the Boltzmann and is computationally efficient.

In an embodiment where the output of the first classifier is not numeric, the first classifier may be configured to combine the outputs using utilize various ensemble voting schemes, which may include, as illustrative, non-limiting examples, majority, weighted averaging, Condorcet methods, Borda count, among others.

In an embodiment, the system may be configured to apply an ensemble of first classifier to generate indicators of binding affinity.

In some embodiments using a plurality of scores to characterize a test object 72 (or training object 66) comprises taking a weighted average of a plurality of scores (from the plurality of poses for the test or training object). When the weighted average satisfies a predetermined threshold value or predetermined threshold value range, the test object is deemed to have a first classification. When the weighted average fails to satisfy the predetermined threshold value or predetermined threshold value range, the test object is deemed to have a second classification. In some embodiments, the weighted average is a Boltzman average of the plurality of scores.

Figure 2D:
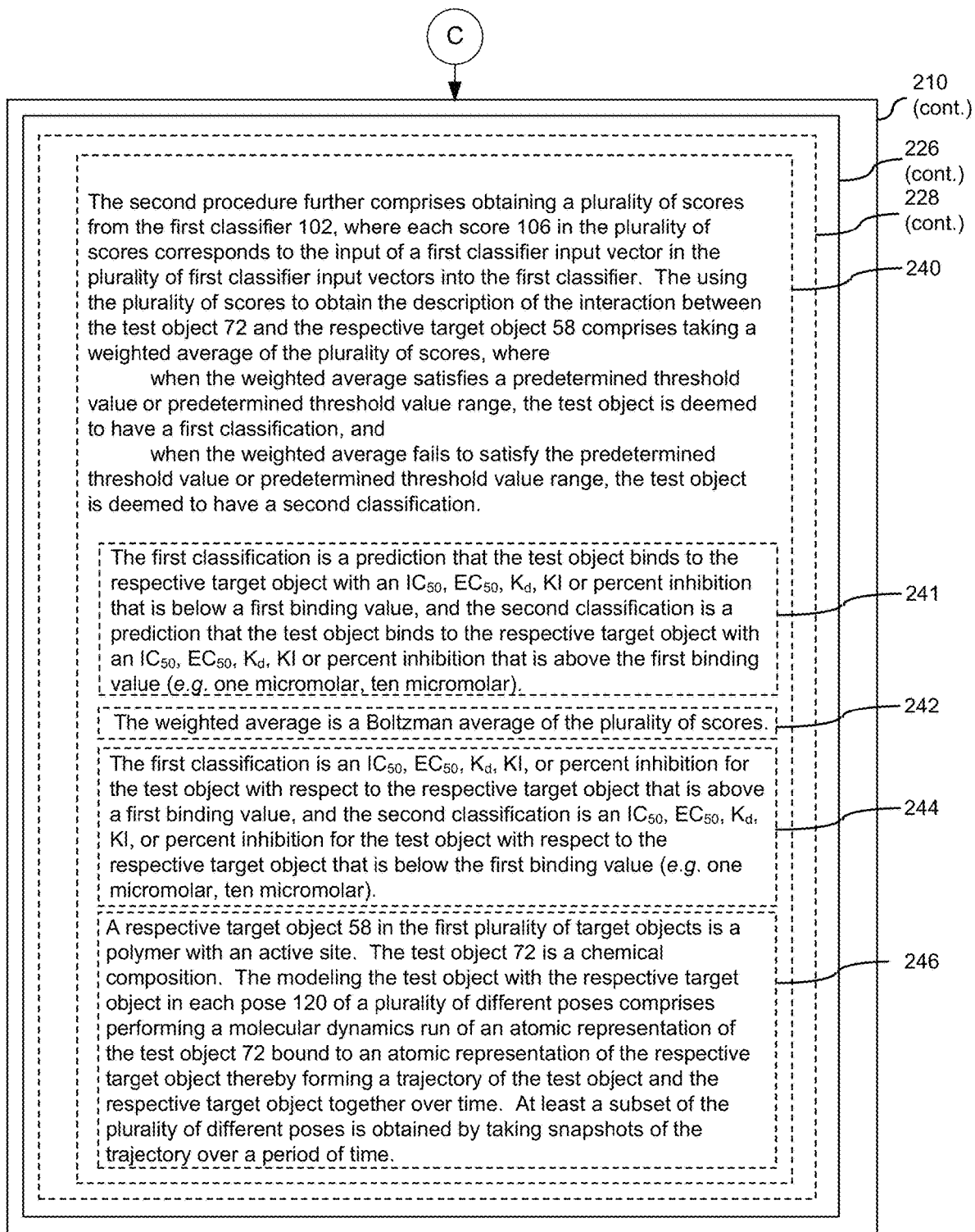

Referring to block 240 of FIG. 2D, in some embodiments the second procedure of block 228 further comprises obtaining a plurality of scores from the first classifier 102, where each score 106 in the plurality of scores corresponds to the input of a first classifier input vector in the plurality of first classifier input vectors into the first classifier. The using the plurality of scores to obtain the description of the interaction between the test object and the respective target object comprises taking a weighted average of the plurality of scores. When the weighted average satisfies a predetermined threshold value or predetermined threshold value range, the test object is deemed to have a first classification. When the weighted average fails to satisfy the predetermined threshold value or predetermined threshold value range, the test object is deemed to have a second classification.

In some such embodiments in accordance with block 240, the first classification is a prediction that the test object 72 binds to the respective target object 58 with an $IC_{50}$, $EC_{50}$, $K_d$, KI, or percent inhibition that is below a first binding value, and the second classification is a prediction that the test object 72 binds to the respective target object 58 with an $IC_{50}$, $EC_{50}$, $K_d$, KI, or percent inhibition that is above the first binding value (e.g. one micromolar, ten micromolar) (block 241).

In some embodiments in accordance with block 240, the first binding value is one nanomolar, ten nanomolar, one hundred nanomolar, one micromolar, ten micromolar, one hundred micromolar, or one millimolar (block 241).

In some embodiments in accordance with block 240, the weighted average is a Boltzman average of the plurality of scores (block 242).

In some embodiments in accordance with block 240, the first classification is an $IC_{50}$, $EC_{50}$, $K_d$, KI, or percent inhibition for the test object with respect to the respective target object that is above a first binding value, and the second classification is an $IC_{50}$, $EC_{50}$, $K_d$, KI, or percent inhibition for the test object with respect to the respective target object that is below the first binding value (e.g. one nanomolar, ten nanomolar, one hundred nanomolar, one micromolar, ten micromolar, one hundred micromolar, or one millimolar) (block 244).

In some embodiments in accordance with block 240, a respective target object 58 in the first plurality of target objects is a polymer with an active site. The test object 72 is a chemical composition. The modeling the test object with the respective target object in each pose 120 of a plurality of different poses comprises performing a molecular dynamics run of an atomic representation of the test object 72 bound to an atomic representation of the respective target object thereby forming a trajectory of the test object and the respective target object together overtime. At least a subset of the plurality of different poses is obtained by taking snapshots of the trajectory over a period of time (block 246).

Referring to block 248, in some embodiments in accordance with block 226, the first classifier 102 comprises a network architecture that includes (i) an input layer 26 for sequentially receiving respective first classifier input vectors in the plurality of first classifier input vectors, (ii) a plurality of convolutional layers 28, and (iii) a scorer 30. The plurality of convolutional layers includes an initial convolutional layer and a final convolutional layer. Each layer in the plurality of convolutional layers is associated with a different set of weights. Responsive to the inputting of a respective first classifier input vector 122 in the plurality of first classifier input vectors to the first classifier 102, the input layer feeds a first plurality of values into the initial convolutional layer as a first function of values in the respective first classifier input vector 22. Each respective convolutional layer 28, other than the final convolutional layer, feeds intermediate values, as a respective second function of (i) the different set of weights associated with the respective convolutional layer and (ii) input values received by the respective convolutional layer, into another convolutional layer in the plurality of convolutional layers. The final convolutional layer 20 feeds final values, as a third function of (i) the different set of weights associated with the final convolutional layer and (ii) input values received by the final convolutional layer, into the scorer. In such embodiments, the second procedure further comprises obtaining a plurality of scores from the scorer 30, where each score in the plurality of scores corresponds to the input of a first classifier input vector 122 in the plurality of first classifier input vectors into the input layer 26, and using the plurality of scores to obtain the description of the interaction between the test object 72 and the respective target object 58.

In some embodiments, referring to FIG. 1B, the respective first classifier input vectors 22, for instance in the form of vectorized representations of voxel maps 22, are stored in the memory 52 of a graphical processing unit along with the first classifier 102 (e.g., a convolutional neural network). This provides the advantage of processing the first classifier input vectors through the first classifier at faster speeds. However, in other embodiments, such as the embodiment of FIG. 1A, any or all of the first classifier input vectors 22, and the first classifier 102 are in memory 92 of system 100A or simply are addressable by system 100A across a network. In some embodiments any or all of the first classifier input vectors 22, the first classifier 102, the second classifier 108, and classifier bias elimination module 56 are in a cloud computing environment.

In some embodiments, referring to FIG. 1B, the plurality of first classifier input vectors 122 is provided to the graphical processing unit memory 52, where the graphical processing unit memory includes a network architecture that includes a first classifier 102 in the form of a convolutional neural network comprising an input layer 26 for sequentially receiving the plurality of vectors, a plurality of convolutional layers 28 and a scorer 30 (block 254). The plurality of convolutional layers includes an initial convolutional layer and a final convolutional layer. In some embodiments, the convolutional neural network 24 is not in GPU memory but rather is in the general purpose memory of system 100.

Details for obtaining a scorer score from the neural network for a complex between a test object 72 (or training object 66) and a target object 58 have been described above. As discussed above, the test object 72 (or training object 66) is docked into a plurality of poses with respect to the target object. To present all such poses at once to the convolutional neural network may require a prohibitively large input field (e.g., an input field of size equal to number of voxels*number of channels*number of poses). While in some embodiments all poses are concurrently presented to the network 24, in preferred embodiments each such pose is processed into a voxel map, vectorized, and serves as sequential input into convolutional neural network. In this way, a plurality of scores are obtained from the scorer 30, where each score in the plurality of scores corresponds to the input of a vector in the plurality of vectors into the input layer 26 of the scorer 30. In some embodiments, the scores for each of the poses of a given test object 72 (or training object 66) with a given target object 58 are combined together to produce a final score 106 for the entire test object 72 (or training object 66). Start here In some embodiments, a convolutional layer 28 in the plurality of convolutional layers comprises a set of learnable filters (also termed kernels). Each filter has fixed three-dimensional size that is convolved (stepped at a predetermined step rate) across the depth, height and width of the input volume of the convolutional layer, computing a dot product (or other functions) between entries (weights) of the filter and the input thereby creating a multi-dimensional activation map of that filter. In some embodiments, the filter step rate is one element, two elements, three elements, four elements, five elements, six elements, seven elements, eight elements, nine elements, ten elements, or more than ten elements of the input space. Thus, consider the case in which a filter has size $5^3$. In some embodiments, this filter will compute the dot product (or other mathematical function) between a contiguous cube of input space that has a depth of five elements, a width of five elements, and a height of five elements, for a total number of values of input space of 125 per voxel channel.

The input space to the initial convolutional layer (e.g., the output from the input layer 26) is formed from either a voxel map 40 or a vectorized representation of the voxel map 22. In some embodiments, the vectorized representation of the voxel map is a one-dimensional vectorized representation of the voxel map which serves as the input space to the initial convolutional layer. Nevertheless, when a filter convolves its input space and the input space is a one-dimensional vectorized representation of the voxel map, the filter still obtains from the one-dimensional vectorized representation those elements that represent a corresponding contiguous cube of fixed space in the target object-test (or training) object complex. In some embodiments, the filter uses standard bookkeeping techniques to select those elements from within the one-dimensional vectorized representation that form the corresponding contiguous cube of fixed space in the target object-test (or training) object complex. Thus, in some instances, this necessarily involves taking a non-contiguous subset of element in the one-dimensional vectorized representation in order to obtain the element values of the corresponding contiguous cube of fixed space in the target object-test (or training) object complex.

In some embodiments, the filter is initialized (e.g., to Gaussian noise) or trained to have 125 corresponding weights (per input channel) in which to take the dot product (or some other form of mathematical operation such as the function disclosed in FIG. 10) of the 125 input space values in order to compute a first single value (or set of values) of the activation layer corresponding to the filter. In some embodiment the values computed by the filter are summed, weighted, and/or biased. To compute additional values of the activation layer corresponding to the filter, the filter is then stepped (convolved) in one of the three dimensions of the input volume by the step rate (stride) associated with the filter, at which point the dot product (or some other form of mathematical operation such as the mathematical function disclosed in FIG. 10) between the filter weights and the 125 input space values (per channel) is taken at the new location in the input volume is taken. This stepping (convolving) is repeated until the filter has sampled the entire input space in accordance with the step rate. In some embodiments, the border of the input space is zero padded to control the spatial volume of the output space produced by the convolutional layer. In typical embodiments, each of the filters of the convolutional layer canvas the entire three-dimensional input volume in this manner thereby forming a corresponding activation map. The collection of activation maps from the filters of the convolutional layer collectively form the three-dimensional output volume of one convolutional layer, and thereby serves as the three-dimensional (three spatial dimensions) input of a subsequent convolutional layer. Every entry in the output volume can thus also be interpreted as an output of a single neuron (or a set of neurons) that looks at a small region in the input space to the convolutional layer and shares parameters with neurons in the same activation map. Accordingly, in some embodiments, a convolutional layer in the plurality of convolutional layers has a plurality of filters and each filter in the plurality of filters convolves (in three spatial dimensions) a cubic input space of $N^3$ with stride Y, where N is an integer of two or greater (e.g., 2, 3, 4, 5, 6, 7, 8, 9, 10, or greater than 10) and Y is a positive integer (e.g. 1, 2, 3, 4, 5, 6, 7, 8, 9, 10, or greater than 10).

In some embodiments, each layer in the plurality of convolutional layers 28 is associated with a different set of weights. With more particularity, each layer in the plurality of convolutional layers includes a plurality of filters and each filter comprises an independent plurality of weights (270). In some embodiments, a convolutional layer has 128 filters of dimension $5^3$ and thus the convolutional layer has 128×5×5×5 or 16,000 weights per channel in the voxel map. Thus, if there are five channels in the voxel map, the convolutional layer will have 16,000×5 weights, or 80,000 weights. In some embodiments some or all such weights (and, optionally, biases) of every filter in a given convolutional layer may be tied together, i.e. constrained to be identical.

Responsive to input of a respective vector 122 in the plurality of vectors, the input layer 26 feeds a first plurality of values into the initial convolutional layer as a first function of values in the respective vector, where the first function is optionally computed using the graphical processing unit 50.

Each respective convolutional layer 28, other than the final convolutional layer, feeds intermediate values, as a respective second function of (i) the different set of weights associated with the respective convolutional layer and (ii) input values received by the respective convolutional layer, into another convolutional layer in the plurality of convolutional layers, where the second function is computed using the graphical processing unit 50. For instance, each respective filter of the respective convolutional layer 28 canvasses the input volume (in three spatial dimensions) to the convolutional layer in accordance with the characteristic three-dimensional stride of the convolutional layer and at each respective filter position, takes the dot product (or some other mathematical function) of the filter weights of the respective filter and the values of the input volume (contiguous cube that is a subset of the total input space) at the respect filter position thereby producing a calculated point (or a set of points) on the activation layer corresponding to the respective filter position. The activation layers of the filters of the respective convolutional layer collectively represent the intermediate values of the respective convolutional layer.

The final convolutional layer feeds final values, as a third function of (i) the different set of weights associated with the final convolutional layer and (ii) input values received by the final convolutional layer that is optionally computed using the graphical processing unit 50, into the scorer. For instance, each respective filter of the final convolutional layer 28 canvasses the input volume (in three spatial dimensions) to the final convolutional layer in accordance with the characteristic three-dimensional stride of the convolutional layer and at each respective filter position, takes the dot product (or some other mathematical function) of the filter weights of the filter and the values of the input volume at the respect filter position thereby calculating a point (or a set of points) on the activation layer corresponding to the respective filter position. The activation layers of the filters of the final convolutional layer collectively represent the final values that are fed to scorer 30.

In some embodiments, the convolutional neural network has one or more activation layers. In some embodiments, the activation layer is a layer of neurons that applies the non-saturating activation function $f(x)=\max(0, x)$. It increases the nonlinear properties of the decision function and of the overall network without affecting the receptive fields of the convolution layer. In other embodiments, the activation layer has other functions to increase nonlinearity, for example, the saturating hyperbolic tangent function $f(x)=\tan h$, $f(x)=|\tan h(x)|$, and the sigmoid function $f(x)=(1+e^{-x})^{-1}$. Nonlimiting examples of other activation functions found in other activation layers in some embodiments for the neural network may include, but are not limited to, logistic (or sigmoid), softmax, Gaussian, Boltzmann-weighted averaging, absolute value, linear, rectified linear, bounded rectified linear, soft rectified linear, parameterized rectified linear, average, max, min, some vector norm LP (for p= 1, 2, 3, . . . , ∞), sign, square, square root, multiquadric, inverse quadratic, inverse multiquadric, polyharmonic spline, and thin plate spline.

The convolutional neural network learns filters within the convolutional layers 28 that activate when they see some specific type of feature at some spatial position in the input. In some embodiments, the initial weights of each filter in a convolutional layer are obtained by training the convolutional neural network against a training data set for the first classifier 63. Accordingly, the operation of the convolutional neural network may yield more complex features than the features historically used to conduct binding affinity prediction. For example, a filter in a given convolutional layer of the network that serves as a hydrogen bond detector may be able to recognize not only that a hydrogen bond donor and acceptor are at a given distance and angles, but also recognize that the biochemical environment around the donor and acceptor strengthens or weakens the bond. Additionally, the filters within the network may be trained to effectively discriminate binders from non-binders in the underlying data.

In some embodiments, the convolutional neural network is configured to adapt for dynamic systems, such as the alternative positions that may be encountered as both the target object and the test object move. In such a target object-test object complex, a number of different configurations may be adopted, with the relative proportion based on the Boltzmann distribution of the free energy of each shape. Both the enthalpic and entropic components of the free energy of the target object-test object complex can depend on the poses adopted by the object ($\Delta G = \Delta H - T \Delta S$). The final binding affinity may be found to be a function of the weighted average of the energies of the set of poses available to the target object-test object complex. To model this physical phenomenon, the convolutional neural network may be configured to sample a large number of alternative positions due to target object and test object motion and to base its binding affinity predictions on this sampled set of configurations of the complex (e.g., by taking the weighted average of all the network 24 scores of these various alternative positions).

As described above, in some embodiments the neural network is configured to develop three-dimensional convolutional layers. The input region to the lowest level convolutional layer 28 may be a cube (or other contiguous region) of voxel channels from the receptive field. Higher convolutional layers evaluate the output from lower convolutional layers, while still having their output be a function of a bounded region of voxels which are close together (in 3-D Euclidean distance).

Biological activity may be invariant under rotation, as well as translation, so the network may be optionally configured to generate rotated feature maps that take advantage of the rotational symmetries of space partitioning. For example, if the system was configured to use cubes to partition the input data, the system could be configured to generate rotated feature maps by tying the weights of the function computations together after a 90 degree rotation.

It may be illustrative to consider a cube which is rotated clockwise: the weights in the upper face of one filter become tied to the weights in the right face of a different filter; in other words, the weights may be constrained to be identical. Rotation may generate 24 feature maps by rotating clockwise by 90 degrees, 180 degrees, 270 degrees, for each of the three XY/XZ/YZ planes. This arrangement reduces the number of parameters to ¹⁄₂₄th of without rotational weight tying, since without weight tying every filter has its own weights.

As an alternative example, if the system were configured to use other polyhedra to partition the input data, the system may be configured to use other rotations to access the isometries appropriate to their symmetry groups. For example, where space has been partitioned using truncated octahedrons, there would be 3 axes of 90 degree rotational symmetry, 4 axes of 120 degree rotational symmetry, and six axes of 180 degree symmetry.

In an embodiment, the convolutional neural network is configured to apply regularization techniques to reduce the tendency of the models to overfit the training objects 66 and training binding data 68.

Zero or more of the network layers in the convolutional neural network may consist of pooling layers. As in a convolutional layer, a pooling layer is a set of function computations that apply the same function over different spatially-local patches of input. For pooling layers, the output is given by a pooling operators, e.g. some vector norm LP for p=1, 2, 3, . . . , ∞, over several voxels. Pooling is typically done per channel, rather than across channels. Pooling partitions the input space into a set of three-dimensional boxes and, for each such sub-region, outputs the maximum. The pooling operation provides a form of translation invariance. The function of the pooling layer is to progressively reduce the spatial size of the representation to reduce the amount of parameters and computation in the network, and hence to also control overfitting. In some embodiments a pooling layer is inserted between successive convolutional 28 layers in a convolutional neural network. Such a pooling layer operates independently on every depth slice of the input and resizes it spatially. In addition to max pooling, the pooling units can also perform other functions, such as average pooling or even L2-norm pooling.

Zero or more of the layers in a convolutional neural network may consist of normalization layers, such as local response normalization or local contrast normalization, which may be applied across channels at the same position or for a particular channel across several positions. These normalization layers may encourage variety in the response of several function computations to the same input.

Neurons in a fully connected layer have full connections to all activations in the previous layer, as seen in regular neural networks. Their activations can hence be computed with a matrix multiplication followed by a bias offset. In some embodiments, each fully connected layer has 512 hidden units, 1024 hidden units, or 2048 hidden units. In some embodiments there are no fully connected layers, one fully connected layer, two fully connected layers, three fully connected layers, four fully connected layers, five fully connected layers, six or more fully connected layers or ten or more fully connected layers in the scorer.

In some embodiments, the scorer comprises a plurality of fully-connected layers and an evaluation layer, and a fully-connected layer in the plurality of fully-connected layers feeds into the evaluation layer. In some embodiments, the evaluation layer is a logistic regression cost layer (block 258). In some embodiments, the evaluation layer discriminates between a plurality of activity classes. In some embodiments, the evaluation layer comprises a logistic regression cost layer over a two activity classes, three activity classes, four activity classes, five activity classes, or six or more activity classes. In some embodiments, the evaluation layer comprises a logistic regression cost layer over a plurality of activity classes. In some embodiments, the evaluation layer comprises a logistic regression cost layer over a two activity classes, three activity classes, four activity classes, five activity classes, or six or more activity classes.

Figure 2E:
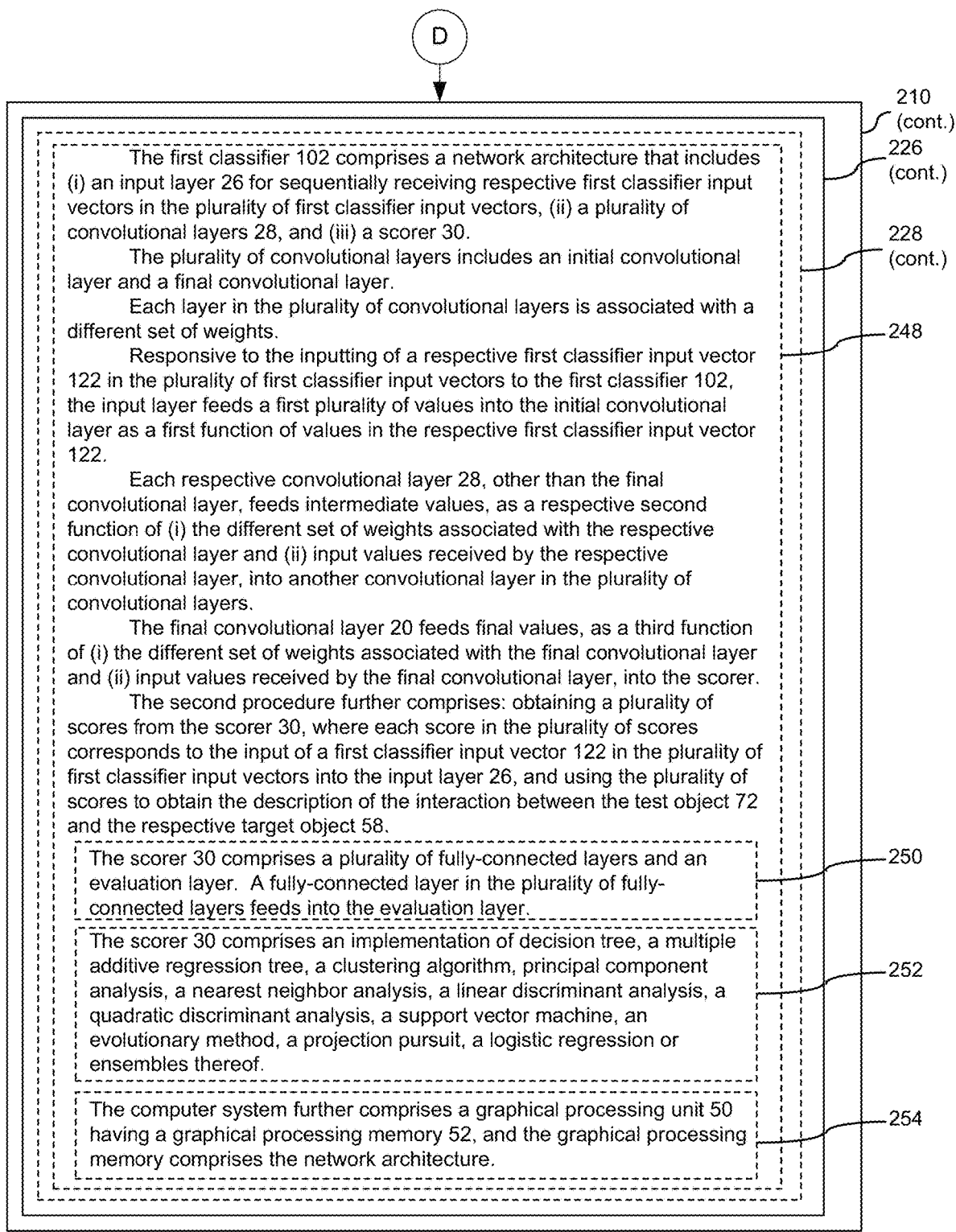

Referring to block 250 of FIG. 2E, in some embodiments of block 248, the scorer 30 comprises a plurality of fully-connected layers and an evaluation layer. A fully-connected layer in the plurality of fully-connected layers feeds into the evaluation layer. For instance, in some embodiments, the evaluation layer comprises a logistic regression cost layer over two activity classes and the first activity classes (first classification) represents an $IC_{50}$, $EC_{50}$, $K_D$ or KI for the test object 72 (or training object) with respect to a respective target object 58 that is above a first binding value, and the second activity class (second classification) is an $IC_{50}$, $EC_{50}$, $K_D$ or KI for the test object (or training object) with respect to a respective target object 58 that is below the first binding value. In some such embodiments, the first binding value is one nanomolar, ten nanomolar, one hundred nanomolar, one micromolar, ten micromolar, one hundred micromolar, or millimolar.

Referring to block 252 of FIG. 2E, in some embodiments of block 248, the scorer 30 comprises an implementation of a decision tree, a multiple additive regression tree, a clustering algorithm, principal component analysis, a nearest neighbor analysis, a linear discriminant analysis, a quadratic discriminant analysis, a support vector machine, an evolutionary method, a projection pursuit, a logistic regression, or ensembles thereof.

In some embodiments, the scorer 30 comprises a fully connected single layer or multilayer perceptron. In some embodiments the scorer comprises a support vector machine, random forest, nearest neighbor. In some embodiments, the scorer 30 assigns a numeric score indicating the strength (or confidence or probability) of classifying the input into the various output categories. In some cases, the categories are binders and nonbinders or, alternatively, the potency level ($IC_{50}$, $EC_{50}$ or KI potencies of e.g., <1 molar, <1 millimolar, <100 micromolar, <10 micromolar, <1 micromolar, <100 nanomolar, <10 nanomolar, <1 nanomolar).

In some embodiments, the evaluation layer discriminates between three activity classes and the first activity classes (first classification) represents an $IC_{50}$, $EC_{50}$ or KI for the test object (or training object) with respect to the target object that is above a first binding value, the second activity class (second classification) is an $IC_{50}$, $EC_{50}$, or KI for the test object (or training object) with respect to the target object that is between the first binding value and a second binding value, and the third activity class (third classification) is an $IC_{50}$, $EC_{50}$, or KI for the test object (or training object) with respect to the target object that is below the second binding value, where the first binding value is other than the second binding value.

In some embodiments, the evaluation layer comprises a logistic regression cost layer over three activity classes and the first activity classes (first classification) represents an $IC_{50}$, $EC_{50}$ or KI for the test object (or training object) with respect to the target object that is above a first binding value, the second activity class (second classification) is an $IC_{50}$, $EC_{50}$, or KI for the test object (or training object) with respect to the target object that is between the first binding value and a second binding value, and the third activity class (third classification) is an $IC_{50}$, $EC_{50}$, or KI for the test object (or training object) with respect to the target object that is below the second binding value, where the first binding value is other than the second binding value.

Figure 2F:
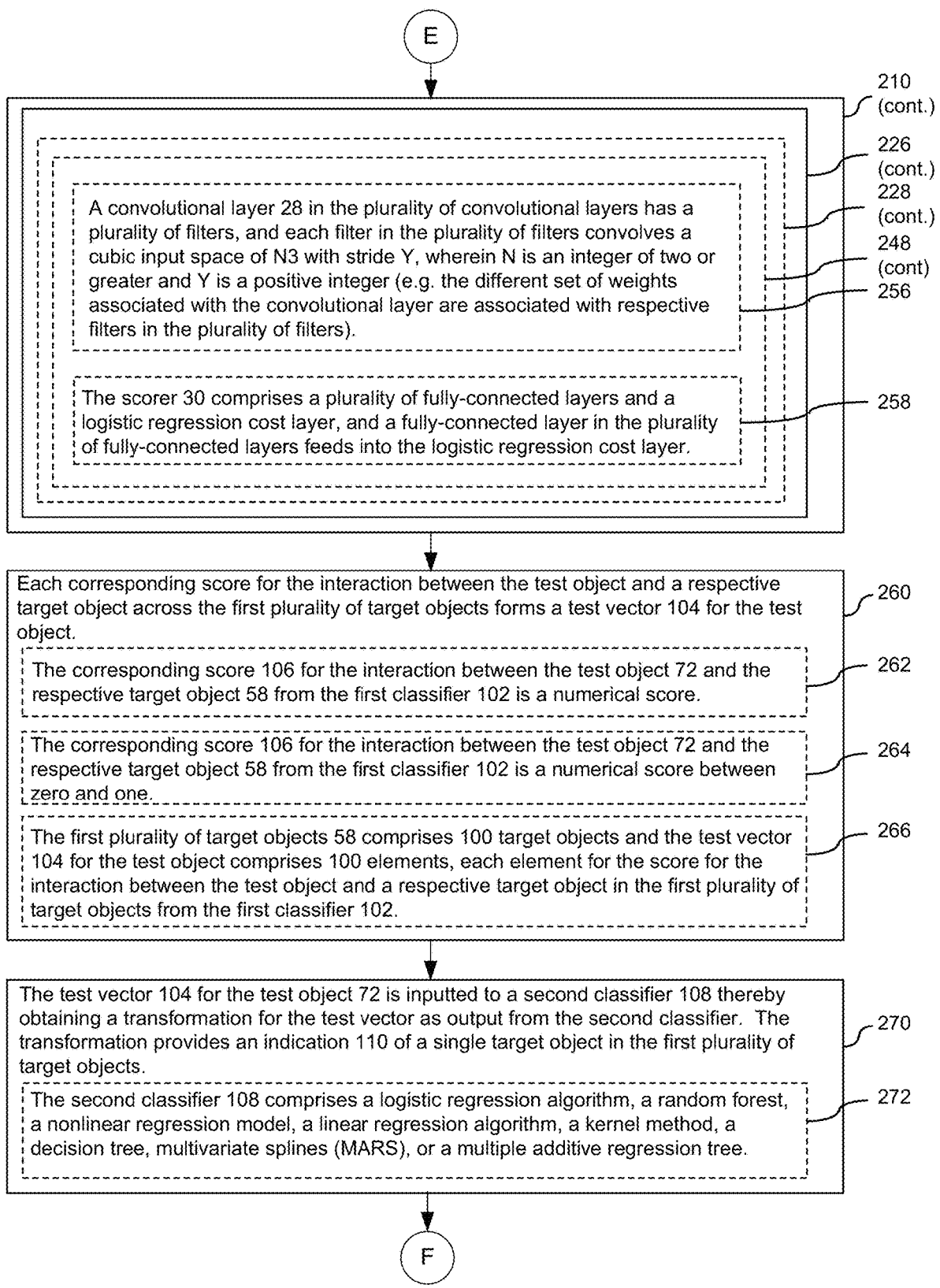
Figure 2H:
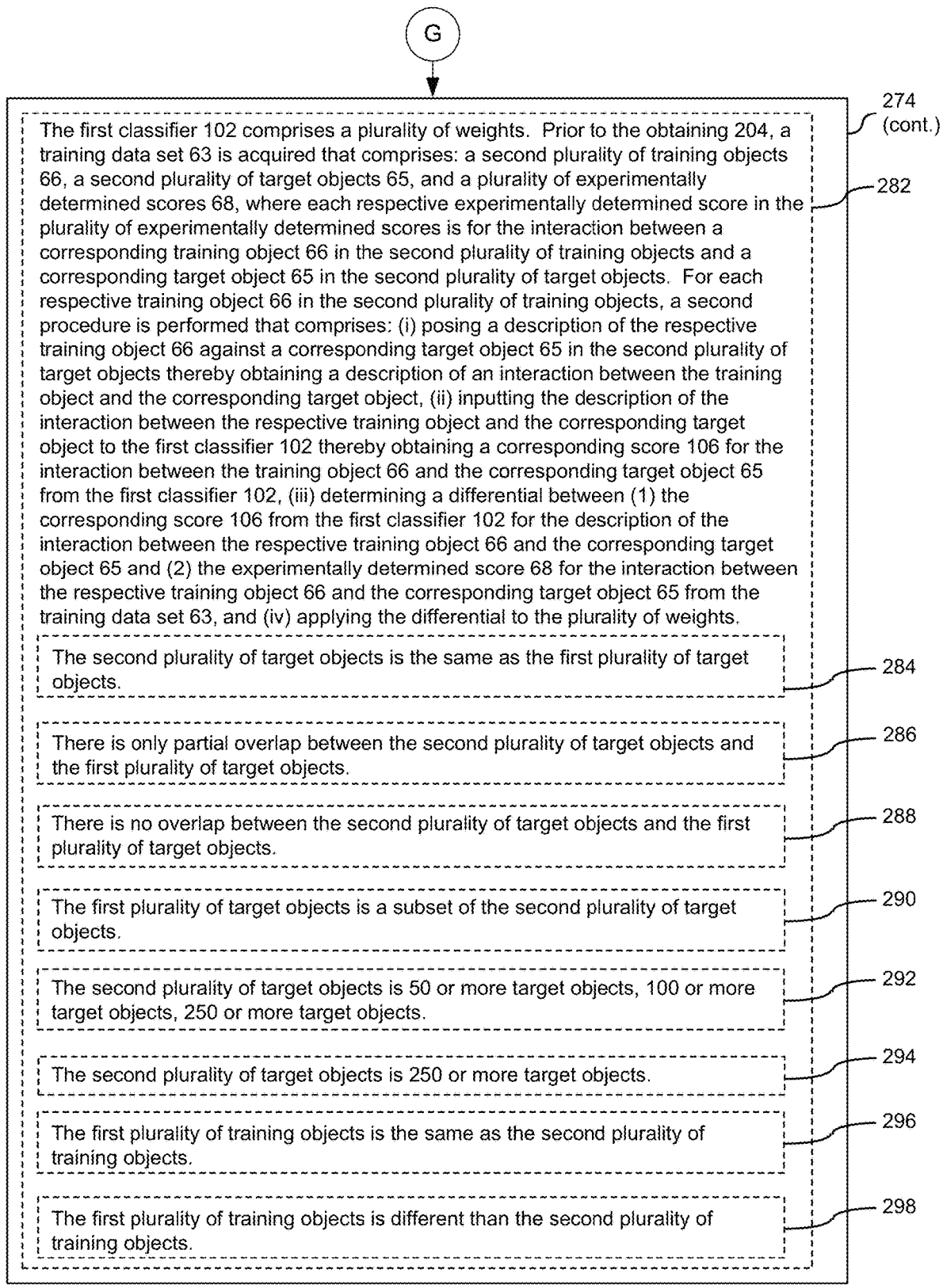

Referring to block 256 of FIG. 2F, in some embodiments of block 248, a convolutional layer 28 in the plurality of convolutional layers has a plurality of filters, and each filter in the plurality of filters convolves a cubic input space of N3 with stride Y, where N is an integer of two or greater and Y is a positive integer (e.g. the different set of weights associated with the convolutional layer are associated with respective filters in the plurality of filters).

Referring to block 260, each corresponding score 106 for the interaction between the test object 72 and a respective target object 58 across the first plurality of target objects forms a test vector 104 for the test object. For instance, consider the case where there are 100 target objects. In this case, the interaction between the test object and each target object is evaluated using the first classifier 102. To do this, the interaction between the test object and the first target object is input into the first classifier using any of the techniques provided in the present disclosure thereby obtaining a first corresponding score 106-1 from the first classifier for this interaction. Next, the interaction between the test object and the second target object is input into the first classifier using any of the techniques provided in the present disclosure thereby obtaining a second corresponding score 106-2 from the first classifier for this interaction. This process is sequentially repeated until a score has been computed by the first classifier for the interaction of the test object against each target object 58. This set of corresponding scores 106 constitutes a test vector, which can be illustrated as:

| Score 106-1-1 | Score 106-1-2 | Score 106-1-3 | Score 106-1-4 | ... | Score 106-1-M |
| --- | --- | --- | --- | --- | --- |

That is, each element of the test vector is for a corresponding score 106 between the test object and a target object. As discussed above, each corresponding score can be numeric or categorical. Furthermore, each corresponding score can be a measure of central tendency for a plurality of poses of the test object against a particular target object. Thus, in some embodiments, the corresponding score 106 for the interaction between the test object 72 and the respective target object 58 from the first classifier 102 is a numerical score (block 262). Referring to block 264, in some embodiments, the corresponding score 106 for the interaction between the test object 72 and the respective target object 58 from the first classifier 102 is a numerical score between zero and one. Referring to block 266, in some embodiments, the first plurality of target objects 58 comprises 50 or more target object, 100 or more target objects or 200 or more target objects and the test vector 104 for the test object comprises 50 or more corresponding elements, 100 or more corresponding elements, or 200 more corresponding elements, each such element for the score for the interaction between the test object and a respective target object in the first plurality of target objects from the first classifier 102.

Referring to block 270 of FIG. 2F, the method continues with the inputting of the test vector 104 for the test object 72 into to a second classifier 108 thereby obtaining a transformation for the test vector as output from the second classifier. The transformation provides an indication 110 of a single target object in the first plurality of target objects. Referring to block 272, in some embodiments, the second classifier 108 comprises a logistic regression algorithm, a random forest, a nonlinear regression model, a linear regression algorithm, a kernel method, a decision tree, multivariate splines (MARS), or a multiple additive regression tree.

A benefit of the second classifier, and the inputting of the test vector 104 from the first classifier into the second classifier, is to correct for error, such as bias, in the first classifier. As such, one aspect of the present disclosure is to train the second classifier against the output of the first classifier so that the second classifier may correct the error in the first classifier.

Referring to block 274 of FIG. 2G, one way such training of the second classifier occurs in some embodiments is to train the second classifier 104 on an object training library 112 for the second classifier 112. The object training library comprises a plurality of training objects 113. The training objects 113 can have any of the characteristics disclosed in the present disclosure for the target object. For instance, in some embodiments, each training object 113 is a chemical compound. A training vector 116 is generated for each training object 113 in the object training library 112. Each respective training vector 116 in the plurality of training vectors is the output from the first classifier 102 after inputting the corresponding training object 113 as a test object in accordance with the first procedure outlined above in blocks 210 through 258. That is, in any of blocks 210 through 258 described above, rather than using the test object, a training object 113 is used. Thus, for a given training object 113, the training vector of the following form is created:

| Score 118-1-1 | Score 118-1-2 | Score 118-1-3 | Score 118-1-4 | ... | Score 118-1-M |
|---|---|---|---|---|---|

In this test vector, each element corresponds to a score by the first classifier for the interaction of a training object 113 with a target object 58. In some embodiments, each score 118 is a scalar score, for instance a real number between 0 and 1. In some embodiments, the score 118 is a categorical score. For instance, in some embodiments, the score 118 is one of two possible values (e.g., "0" or "1"). In some embodiments, the score 118 is one of two possible categories ("not binding" or "binding"). In some embodiments, the score 118 is one of three possible categories ("not binding," "medium binding," and "strongly binding"). Any number of categories for the score 118 are contemplated and all such categories are with the scope of the present disclosure.

For purposes of training the first classifier against all the possible target objects, in some embodiments the object training library includes, for each respective target object, a subset of training objects 113 that are associated with the respective target object. For instance, consider the case where there are five target objects and the first classifier outputs a categorical "binds" or "does not bind" upon input of the interaction between a training object and a target object. In this instance, a first subset of the target objects will include target objects that the first classifier deems to only bind to the first target, a second subset of the target objects will include target objects that the first classifier deems to only bind to the second target, a third subset of the target objects will include target objects that the first classifier deems to only bind to the third target, a fourth subset of the target objects will include target objects that the first classifier deems to only bind to the fourth target, and a fifth subset of the target objects will include target objects that the first classifier deems to only bind to the fifth target. As such, each training object 113 in a first portion of the plurality of training objects in the object training library for the second classifier are uniquely associated with a corresponding target object in the first plurality of target objects.

Moreover, to further train the second classifier, another portion of the training objects in the object training library for the second classifier will include training objects 113 that are not associated with any target object 58. For instance, in the example above where there are five target objects and the first classifier outputs a categorical "binds" or "does not bind" upon input of the interaction between a training object and a target object, each target object in this second portion of the training objects in library 112 will cause the first classifier to call "does not bind" for all five target objects. In some embodiments the training object association 114 of FIG. 1A serves as the class label for each training object. In typical embodiments, this class label is for bookkeeping purposes only and is not used to train the second classifier. For instance, the object association (label) 114 can be used to specify which of the target objects 58 a given training object 113 is associated with. In some embodiments, a training object is only associated with a single target object, at most, and is not associated with the other target objects.

As used here, the term "associated" is context dependent and the exact quantitative value for what it means to be associated or not associated will vary. In one example, a training object 113 is deemed to be associated with a target object when the $IC_{50}$, $EC_{50}$, Kd, KI, or percent inhibition of the training object against the target object is one nanomolar or less and the target object is deemed to be not associated with the target object when the $IC_{50}$ of the training object against the target object is greater than 1 nanomolar. In another example, a training object 113 is deemed to be associated with a target object when the $IC_{50}$, $EC_{50}$, Kd, KI, or percent inhibition of the training object against the target object is ten nanomolar or less and the target object is deemed to be not associated with the target object when the IC50 of the training object against the target object is greater than ten nanomolar. In another example, a training object 113 is deemed to be associated with a target object when the $IC_{50}$, $EC_{50}$, Kd, KI or percent inhibition of the training object against the target object is one hundred nanomolar or less and the target object is deemed to be not associated with the target object when the IC50 of the training object against the target object is greater than one hundred nanomolar. In another example, a training object 113 is deemed to be associated with a target object when the $IC_{50}$, $EC_{50}$, Kd, KI, or percent inhibition of the training object against the target object is one micromolar or less and the target object is deemed to be not associated with the target object when the IC50 of the training object against the target object is greater than ten micromolar. In another example, a training object 113 is deemed to be associated with a target object when the $IC_{50}$, $EC_{50}$, Kd, KI, or percent inhibition of the training object against the target object is one micromolar or less and the target object is deemed to be not associated with the target object when the IC50 of the training object against the target object is greater than one micromolar. In another example, a training object 113 is deemed to be associated with a target object when the $IC_{50}$, $EC_{50}$, Kd, KI, or percent inhibition of the training object against the target object is ten micromolar or less and the target object is deemed to be not associated with the target object when the IC50 of the training object against the target object is greater than ten micromolar. In another example, a training object 113 is deemed to be associated with a target object when the $IC_{50}$, $EC_{50}$, Kd, KI, or percent inhibition of the training object against the target object is one hundred micromolar or less and the target object is deemed to be not associated with the target object when the IC50 of the training object against the target object is greater than one hundred micromolar. In another example, a training object 113 is deemed to be associated with a target object when the $IC_{50}$, $EC_{50}$, Kd, KI, or percent inhibition of the training object against the target object is one millimolar or less and the target object is deemed to be not associated with the target object when the IC50 of the training object against the target object is greater than one millimolar.

In some embodiments, referring to block 276 of FIG. 2G as an illustrative example, in some embodiments the first subset of the first plurality of training objects (the subset in which each training object is associated with only one of the target objects and not the other target objects) comprises 1000 training objects 113, and the first plurality of target objects 72 comprises 100 target objects. For each respective target object in the first plurality of target objects, the first subset of the first plurality of training objects includes at least five training objects that are uniquely associated with the respective target object, and the second subset (the subset in which each training object is not associated with any of the target objects) of the first plurality of training objects comprises 10000 training objects.

Referring to block 278, in some embodiments, effort is made to ensure that the training library does not incorrectly train a particular training object type. In one such embodiment, each respective training object 113 in the first plurality of training objects (the subset in which each training object is associated with only one of the target objects and not the other target objects) is a chemical compound with a corresponding molecular fingerprint (e.g., a Daylight fingerprint, a BCI fingerprint, an ECFP fingerprint, an ECFC fingerprint, an MDL fingerprint, an APFP fingerprint, a TTFP fingerprint, or a UNITY 2D fingerprint) that is dissimilar to the molecular fingerprint of any training object in the object training library 112 for the second classifier that is not uniquely associated with the same target object as the respective training object (block 278). See Franco, 2014, "The Use of 2D fingerprint methods to support the assessment of structural similarity in orphan drug legislation," J. Cheminform 6, p. 5, and Rensi and Altman, 2017, "Flexible Analog Search with Kernel PCA Embedded Molecule Vectors," Computational and Structural Biotechnology Journal, doi:10.1016/j.csbj.2017.03.003, each of which is hereby incorporated by reference. For instance, consider the case where some of the training objects are associated with a first target object and some of the training objects are associated with a second target object. In such embodiments, care is taken to make sure that none of the training objects that are associated with the first target object have a molecular fingerprint that is similar to the molecular fingerprint of any of the training objects that are associated with the second target object. In some embodiments, the molecular fingerprint of one training object is deemed to be dissimilar to the molecular fingerprint of another training object in the object training library 112 when the Tanimoto coefficient between the respective training object and the molecular fingerprint of the other training object is less than 0.70, less than 0.60 or less than 0.50 (block 280).

Referring to block 274 of FIG. 2G, some embodiments of the present disclosure encompass training the first classifier 102 as well. In some such embodiments, the first classifier 102 comprises a plurality of weights, e.g., in the case of a convolutional neural network or a classical neural network, etc. Prior to running the obtaining of block 204, a training data set 63 for the first classifier 102 is acquired that comprises a second plurality of training objects 66, a second plurality of target objects 65, and a plurality of experimentally determined scores 68, where each respective experimentally determined score in the plurality of experimentally determined scores is for the interaction between a corresponding training object 66 in the second plurality of training objects and a corresponding target object 65 in the second plurality of target objects. In some embodiments, the experimentally determined scores 68 include binding data against one or more of the target objects 58. For instance, in some embodiments, this binding data is obtained from wet lab experiments in which an $IC_{50}$, $EC_{50}$, Kd, KI, or percent inhibition for the training object 66 against a target object 65 is measured. Example binding assays that may be used to acquire binding data 68 are disclosed in Khan and Findlay, 2010, *Ligand-Binding Assays*, 2010, John Wiley & Sons, Inc., New York, which is hereby incorporated by reference.

For each respective training object 66 in the second plurality of training objects, a second procedure is performed that comprises: (i) posing a description of the respective training object 66 against a corresponding target object 65 in the second plurality of target objects thereby obtaining a description of an interaction between the training object and the corresponding target object, (ii) inputting the description of the interaction between the respective training object and the corresponding target object to the first classifier 102 thereby obtaining a corresponding score 106 for the interaction between the training object 66 and the corresponding target object 65 from the first classifier 102, (iii) determining a differential between (1) the corresponding score 106 from the first classifier 102 for the description of the interaction between the respective training object 66 and the corresponding target object 65 and (2) the experimentally determined score 68 for the interaction between the respective training object 66 and the corresponding target object 65 from the training data set 63, and (iv) applying the differential to the plurality of weights. There is no requirement that a training object 66 include binding data 68 against all the target objects 63. In some embodiments, the interaction between a respective training object 66 and target objects is only evaluated with the first classifier 102 for those target objects for which there is binding data 68.

In some embodiments, the target objects 65 in the training data set 63 are the same as the first plurality of target objects 58 discussed above in conjunction with blocks 210 through 258 (block 284). In some embodiments, there is only partial overlap between the plurality of target objects 65 in the training data set 63 for the first classifier and the first plurality of target objects discussed above in conjunction with blocks 210 through 258 (block 286). In some embodiments, there is no overlap between the second plurality of target objects of the training data set 63 and the first plurality of target objects discussed above in conjunction with blocks 210 through 258 (block 288). In some embodiments, the first plurality of target objects discussed above in conjunction with blocks 210 through 258 is a subset of the plurality of target objects 65 in the training data set 63 for the first classifier (block 290). In some embodiments, the second plurality of target objects 65 in the training data set 63 for the first classifier comprises 50 or more target objects, 100 or more target objects, 250 or more target objects (block 292). In some embodiments, the second plurality of target objects 65 in the training data set 63 for the first classifier is 250 or more target objects (block 294).

In some embodiments, the first plurality of training objects 113 in the object training library 112 for the second classifier is the same as the second plurality of training objects 66 in the training data set 63 for the first classifier (block 296). In some embodiments, the first plurality of training objects 113 in the object training library 112 for the second classifier is different than the second plurality of training objects 66 in the training data set 63 for the first classifier (block 298).

In some embodiments, the first classifier 102 is treated as a trained black box and no further training of the first classifier is performed other than conventional training of the first classifier by methods not disclosed herein. In such embodiments, the trained black box is still used to train the second classifier so that the second classifier may reduce error in the first classifier.

In some such embodiments, the first classifier outputs one of two possible activity classes for each training object against a given target object. For instance, the single value provided for each respective training object by the first classifier is in a first activity class (e.g., binders) when it is below a predetermined threshold value and is in a second activity class (e.g., nonbinders) when the number is above the predetermined threshold value. The activity classes assigned by the first classifier are compared to the actual activity classes as represented by the training object binding data 68. In typical non-limiting embodiments, such training object binding data 68 is from independent web lab binding assays. Errors in activity class assignments made by the first classifier, as verified against the binding data 68, are then back-propagated through the weights of the first classifier in order to train the first classifier. For instance, in the case where the first classifier is a convolutional neural network such as the one illustrated in FIG. 1B, the filter weights of respective filters in the convolutional layers 28 of the network are adjusted in such back-propagation. In an exemplary embodiment, the first classifier is trained against the errors in the activity class assignments made by the first classifier, in view of the binding data 68, by stochastic gradient descent with the AdaDelta adaptive learning method (Zeiler, 2012 "ADADELTA: an adaptive learning rate method," CoRR, vol. abs/1212.5701, which is hereby incorporated by reference), and the back propagation algorithm provided in Rumelhart et al., 1988, "Neurocomputing: Foundations of research," ch. Learning Representations by Back-propagating Errors, pp. 696-699, Cambridge, MA, USA: MIT Press, which is hereby incorporated by reference. In some such embodiments the two possible activity classes are respectively a binding constant greater than a given threshold amount (e.g., an $IC_{50}$, $EC_{50}$, or KI for the training object with respect to the target object that is greater than one nanomolar, ten nanomolar, one hundred nanomolar, one micromolar, ten micromolar, one hundred micromolar, or one millimolar) and a binding constant that is below the given threshold amount (e.g., an $IC_{50}$, $EC_{50}$, or KI for the training object with respect to the target object that is less than one nanomolar, ten nanomolar, one hundred nanomolar, one micromolar, ten micromolar, one hundred micromolar, or one millimolar). In some such embodiments, a plurality of poses for each training object against a given target object are sequentially run through the first classifier and the weighted average of the scores for these poses as computed by the first classifier is compared to binding data 68 that is acquired by wet lab binding assays.

In some such embodiments, the first classifier outputs one of a plurality of possible activity classes (e.g., three or more activity classes, four or more activity classes, five or more activity classes) for each training object against a given target object. For instance, the single value provided for each respective training object by the first classifier (e.g., the weighted average of a plurality of poses or a single value from a single pose) is in a first activity class when the number falls into a first range, is in a second activity class when the number falls into a second range, is in a third activity class when the number falls into a third range, and so forth. The activity classes assigned by the first classifier are compared to the actual activity classes as represented by the training object binding data 68. Errors in activity class assignments made by the first classifier, as verified against the binding data 68, are then used to train the first classifier using the techniques discussed above. In some embodiments, each respective classification in the plurality of classifications is an $IC_{50}$, $EC_{50}$ or KI range for the training object with respect to the target object.

In some embodiments, a single pose for each respective training object against a given target object is run through the first classifier and the resulting respective score assigned by the first classifier for each respective training object is compared to binding data 68 for the respective training object that has been separately acquired by one or more wet lab binding assay techniques. Then, errors in activity class assignments made by the first classifier for the training objects, as verified against the binding data 68 for the training objects, are used to train the first classifier using the techniques discussed above.

In some embodiments, the weighted mean average of one or more poses of a training object against each of a plurality of target objects 65 evaluated by the classifier using the techniques disclosed herein is compared to the binding data 68 for the respective training objects that is separately acquired by one or more wet lab binding assay techniques. For instance, in some embodiments, the plurality of target objects 65 are taken from a molecular dynamics run in which each target object in the plurality of target objects represents the same polymer at a different time step during the molecular dynamics run. Discrepancies between target object classification by the first classifier and the object classification by the wet lab binding assays are then used to train the first classifier using the techniques discussed above.

In some embodiments, first classifier classification of a plurality of training objects is compared to the binding data 68 using non-parametric techniques. For instance, the classifier is used to rank order the plurality of training objects 66 with respect to a given property (e.g., binding against a given target object 65) and this rank order is compared to the rank order provided by the binding data 68 that is acquired by wet lab binding assays for the plurality of training objects. This gives rise to the ability to train the first classifier 102 on the errors in the calculated rank order using the first classifier error correction techniques discussed above. In some embodiments, the error (differences) between the ranking by the training objects by the first classifier 102 and the ranking of the training objects as determined by the binding data 68 is computed using a Wilcoxon Mann Whitney function (Wilcoxon signed-rank test) or other non-parametric test and this error is back-propagated through the first classifier in order to further train the network using the first classifier error correction techniques discussed above.

In an embodiment where the first classifier is a convolutional neural network, first classifier may be configured to be trained to improve the accuracy of its prediction by modifying the weights in the filters in the convolutional layers 28 as well as the biases in the network layers. The weights and biases may be further constrained with various forms of regularization such as L1, L2, weight decay, and dropout. In some such embodiments, the first classifier, in the form of a convolutional neural network, may optionally be configured to tune the weights of the network to model the input distribution of the training data through greedy, layerwise, generative pre-training against the training objects using the contrastive divergence algorithm.

In an embodiment, the first classifier may optionally, where training data is labeled (e.g., with the binding data 68), tune the weights within the first classifier to potentially minimize the error between the neural network's predicted binding affinities and/or categorizations and the training data's reported binding affinities and/or categorizations. Various methods may be used to minimize error function, such as gradient descent methods, which may include, but are not limited to, log-loss, sum of squares error, hinge-loss methods. These methods may include second-order methods or approximations such as momentum, Hessian-free estimation, Nesterov's accelerated gradient, adagrad, etc. Unlabelled generative pretraining and labeled discriminative training may also be combined.

Input geometric data may be grouped into training examples. For example, it is often the case that a single set of molecules, cofactors, and protein has multiple geometric measurements, where each "snapshot" describes alternative conformations and poses that the target object and the training objects (or test objects) may adopt. Similarly, in instances where the target object is a protein, different tautomers for the protein sidechains, cofactors, and the training (or test) objects may also be sampled. Because these states all contribute to the behavior of the biological system, as per the Boltzmann distribution, a system to predict binding affinity may be configured to consider these states together (for instance by taking the weighted average of these samplings). Optionally, these training examples may be labeled with binding information. If quantitative binding information is available (e.g., binding data 68), the labels may be the numerical binding affinities. Alternatively, the training examples may be assigned labels from a set of two or more ordered categories (e.g., two categories of binders and nonbinders, or several possibly-overlapping categories describing the ligands as binders of potencies<1 molar, <1 millimolar, <100 micromolar, <10 micromolar, <1 micromolar, <100 nanomolar, <10 nanomolar, <1 nanomolar). Binding data 68 may be derived or received from a variety of sources, such as experimental measurements, computed estimates, expert insight, or presumption (for example, a random pair of molecule and protein are highly unlikely to bind).

Example 1—Use Cases

The following are sample use cases provided for illustrative purposes only that describe some applications of some embodiments of the present disclosure. Other uses may be considered, and the examples provided below are non-limiting and may be subject to variations, omissions, or may contain additional elements.

While each example below illustrates binding affinity prediction, the examples may be found to differ in whether the predictions are made over a single molecule, a set, or a series of iteratively modified molecules; whether the predictions are made for a single target or many, whether activity against the targets is to be desired or avoided, and whether the important quantity is absolute or relative activity; or, if the molecules or targets sets are specifically chosen (e.g., for molecules, to be existing drugs or pesticides; for proteins, to have known toxicities or side-effects).

Hit Discovery

Pharmaceutical companies spend millions of dollars on screening compounds to discover new prospective drug leads. Large compound collections are tested to find the small number of compounds that have any interaction with the disease target of interest. Unfortunately, wet lab screening suffers experimental errors and, in addition to the cost and time to perform the assay experiments, the gathering of large screening collections imposes significant challenges through storage constraints, shelf stability, or chemical cost. Even the largest pharmaceutical companies have only between hundreds of thousands to a few millions of compounds, versus the tens of millions of commercially available molecules and the hundreds of millions of simulate-able molecules.

A potentially more efficient alternative to physical experimentation is virtual high throughput screening. In the same manner that physics simulations can help an aerospace engineer to evaluate possible wing designs before a model is physically tested, computational screening of molecules can focus the experimental testing on a small subset of high-likelihood molecules. This may reduce screening cost and time, reduces false negatives, improves success rates, and/or covers a broader swath of chemical space.

In this application, a protein target may be provided as input to the system. A large set of molecules may also be provided. For each molecule, a binding affinity is predicted against the protein target using the disclosed method. The resulting scores, from the second classifier, may be used to rank the molecules, with the best-scoring molecules being most likely to bind the target protein. Optionally, the ranked molecule list may be analyzed for clusters of similar molecules; a large cluster may be used as a stronger prediction of molecule binding, or molecules may be selected across clusters to ensure diversity in the confirmatory experiments.

Off-Target Side-Effect Prediction

Many drugs may be found to have side-effects. Often, these side-effects are due to interactions with biological pathways other than the one responsible for the drug's therapeutic effect. These off-target side-effects may be uncomfortable or hazardous and restrict the patient population in which the drug's use is safe. Off-target side effects are therefore an important criterion with which to evaluate which drug candidates to further develop. While it is important to characterize the interactions of a drug with many alternative biological targets, such tests can be expensive and time-consuming to develop and run. Computational prediction can make this process more efficient.

In applying an embodiment of the invention, a panel of biological targets may be constructed that are associated with significant biological responses and/or side-effects. The system may then be configured to predict binding against each protein in the panel in turn. Strong activity (that is, activity as potent as compounds that are known to activate the off-target protein) against a particular target as determined by the second classifier may implicate the molecule in side-effects due to off-target effects.

Toxicity Prediction

Toxicity prediction is a particularly-important special case of off-target side-effect prediction. Approximately half of drug candidates in late stage clinical trials fail due to unacceptable toxicity. As part of the new drug approval process (and before a drug candidate can be tested in humans), the FDA requires toxicity testing data against a set of targets including the cytochrome P450 liver enzymes (inhibition of which can lead to toxicity from drug-drug interactions) or the hERG channel (binding of which can lead to QT prolongation leading to ventricular arrhythmias and other adverse cardiac effects).

In toxicity prediction, the system may be configured to constrain the off-target proteins to be key antitargets (e.g. CYP450, hERG, or 5-HT$_{2B}$ receptor). The binding affinity for a drug candidate may then predicted against these proteins. Optionally, the molecule may be analyzed to predict a set of metabolites (subsequent molecules generated by the body during metabolism/degradation of the original molecule), which can also be analyzed for binding against the antitargets. Problematic molecules may be identified by the second classifier and modified to avoid the toxicity or development on the molecular series may be halted to avoid wasting additional resources.

Potency Optimization

One of the key requirements of a drug candidate is strong binding against its disease target. It is rare that a screen will find compounds that bind strongly enough to be clinically effective. Therefore, initial compounds seed a long process of optimization, where medicinal chemists iteratively modify the molecular structure to propose new molecules with increased strength of target binding. Each new molecule is synthesized and tested, to determine whether the changes successfully improved binding. The system may be configured to facilitate this process by replacing physical testing with computational prediction.

In this application, the disease target and a set of lead molecules may be input into the system. The second classifier may be configured to produce binding affinity predictions for the set of leads. Optionally, the second classifier could highlight differences between the candidate molecules that could help inform the reasons for the predicted differences in binding affinity. The medicinal chemist user can use this information to propose a new set of molecules with, hopefully, improved activity against the target. These new alternative molecules may be analyzed in the same manner.

Selectivity Optimization

As discussed above, molecules tend to bind a host of proteins at a variety of strengths. For example, the binding pockets of protein kinases (which are popular chemotherapy targets) are very similar and most kinase inhibitors affect many different kinases. This means that various biological pathways are simultaneously modified, which yields a "dirty" medicinal profile and many side-effects. The critical challenge in the design of many drugs, therefore, is not activity per se but specificity: the ability to selectively target one protein (or a subset of proteins) out from a set of possibly-closely related proteins.

Our system can reduce the time and cost of optimizing the selectivity of a candidate drug. In this application, a user may input two sets of proteins. One set describes proteins against which the compound should be active, while the other set describes proteins against which the compound should be inactive. The system may be configured so that the second classifier makes predictions for the molecule against all of the proteins in both sets, establishing a profile of interaction strengths. Optionally, these profiles could be analyzed to suggest explanatory patterns in the proteins. The user can use the information generated by the system to consider structural modifications to a molecule that would improve the relative binding to the different protein sets, and to design new candidate molecules with better specificity. Optionally, the system could be configured to highlight differences between the candidate molecules that could help inform the reasons for the predicted differences in selectivity. The proposed candidates can be analyzed iteratively, to further refine the specificity of their activity profiles.

Fitness Function for Automated Molecular Design

Automated tools to perform the preceding optimizations are valuable. A successful molecule requires optimization and balance among potency, selectivity, and toxicity. "Scaffold hopping" (when the activity of a lead compound is preserved but the chemical structure is significantly altered) can yield improved pharmacokinetics, pharmacodynamics, toxicity, or intellectual property profiles. Algorithms exist to iteratively suggest new molecules, such as random generation of molecules, growth of molecular fragments to fill a given binding site, genetic algorithms to "mutate" and "cross-breed" a population of molecules, and swapping of pieces of a molecule with bioisosteric replacements. The drug candidates generated by each of these methods must be evaluated against the multiple objectives described above (potency, selectivity, toxicity) and, in the same way that the technology can be informative on each of the preceding manual settings (binding prediction, selectivity, side-effect and toxicity prediction), it can be incorporated in an automated molecular design system.

Drug Repurposing

All drugs have side-effects and, from time to time, these side-effects are beneficial. The best known example might be aspirin, which is generally used as a headache treatment but is also taken for cardiovascular health. Drug repositioning can significantly reduce the cost, time, and risk of drug discovery because the drugs have already been shown to be safe in humans and have been optimized for rapid absorption and favorable stability in patients. Unfortunately, drug repositioning has been largely serendipitous. For example, sildenafil (Viagra), was developed as a hypertension drug and was unexpectedly observed to be an effective treatment for erectile dysfunction. Computational prediction of off-target effects can be used in the context of drug repurposing to identify compounds that could be used to treat alternative diseases.

In this application, as in off-target side-effect prediction, the user may assemble a set of possible target proteins, where each protein is linked to a disease. That is, inhibition of each protein would treat a (possibly different) disease; for example, inhibitors of Cyclooxygenase-2 can provide relief from inflammation, whereas inhibitors of Factor Xa can be used as anticoagulants. These proteins are annotated with the binding affinity of approved drugs, if any exist. We then assemble a set of molecules, restricting the set to molecules that have been approved or investigated for use in humans. Finally, for each pair of protein and molecule, the user may use the system, including the second classifier, to predict the binding affinity. Candidates for drug repurposing may be identified if the predicted binding affinity of the molecule is close to the binding affinity of effective drugs for the protein.

Drug Resistance Prediction

Drug resistance is an inevitable outcome of pharmaceutical use, which puts selection pressure on rapidly dividing and mutating pathogen populations. Drug resistance is seen in such diverse disease agents as viruses (HIV), exogenous microorganisms (MRSA), and disregulated host cells (cancers). Over time, a given medicine will become ineffective, irrespective of whether the medicine is antibiotics or chemotherapies. At that point, the intervention can shift to a different medicine that is, hopefully, still potent. In HIV, there are well-known disease progression pathways that are defined by which mutations the virus will accumulate while the patient is being treated.

There is considerable interest in predicting how disease agents adapt to medical intervention. One approach is to characterize which mutations will occur in the disease agent while under treatment. Specifically, the protein target of a medicine needs to mutate so as to avoid binding the drug while simultaneously continue to bind its natural substrate.

In this application, a set of possible mutations in the target protein may be proposed. For each mutation, the resulting protein shape may be predicted. For each of these mutant protein forms, the system may be configured to predict a binding affinity for both the natural substrate and the drug. The mutations that cause the protein to no longer bind to the drug but also to continue binding to the natural substrate are candidates for conferring drug resistance. These mutated proteins may be used as targets against which to design drugs, e.g. by using these proteins as inputs to one of these other prediction use cases.

Personalized Medicine

Ineffective medicines should not be administered. In addition to the cost and hassle, all medicines have side-effects. Moral and economic considerations make it imperative to give medicines only when the benefits outweigh these harms. It may be important to be able to predict when a medicine will be useful. People differ from one another by a handful of mutations. However, small mutations may have profound effects. When these mutations occur in the disease target's active (orthosteric) or regulatory (allosteric) sites, they can prevent the drug from binding and, therefore, block the activity of the medicine. When a particular person's protein structure is known (or predicted), the system can be configured to predict whether a drug will be effective or the system may be configured to predict when the drug will not work.

For this application, the system may be configured to receive as input the drug's chemical structure and the specific patient's particular expressed protein. The system may be configured to predict binding between the drug and the protein and, if the drug's predicted binding affinity that particular patient's protein structure is too weak to be clinically effective, clinicians or practitioners may prevent that drug from being fruitlessly prescribed for the patient.

Drug Trial Design

This application generalizes the above personalized medicine use case to the case of patient populations. When the system can predict whether a drug will be effective for a particular patient phenotype, this information can be used to help design clinical trials. By excluding patients whose particular disease targets will not be sufficiently affected by a drug, a clinical trial can achieve statistical power using fewer patients. Fewer patients directly reduces the cost and complexity of clinical trials.

For this application, a user may segment the possible patient population into subpopulations that are characterized by the expression of different proteins (due to, for example, mutations or isoforms). The system may be configured to predict the binding strength of the drug candidate against the different protein types. If the predicted binding strength against a particular protein type indicates a necessary drug concentration that falls below the clinically-achievable in-patient concentration (as based on, for example, physical characterization in test tubes, animal models, or healthy volunteers), then the drug candidate is predicted to fail for that protein subpopulation. Patients with that protein may then be excluded from a drug trial.

Agrochemical Design

In addition to pharmaceutical applications, the agrochemical industry uses binding prediction in the design of new pesticides. For example, one desideratum for pesticides is that they stop a single species of interest, without adversely impacting any other species. For ecological safety, a person could desire to kill a weevil without killing a bumblebee.

For this application, the user could input a set of protein structures, from the different species under consideration, into the system. A subset of proteins could be specified as the proteins against which to be active, while the rest would be specified as proteins against which the molecules should be inactive. As with previous use cases, some set of molecules (whether in existing databases or generated de novo) would be considered against each target, and the system would return the molecules with maximal effectiveness against the first group of proteins while avoiding the second.

Materials Science

To predict the behavior and properties of new materials, it may be useful to analyze molecular interactions. For example, to study solvation, the user may input a repeated crystal structure of a given small molecule and assess the binding affinity of another instance of the small molecule on the crystal's surface. To study polymer strength, a set of polymer strands may be input analogously to a protein target structure, and an oligomer of the polymer may be input as a small molecule. Binding affinity between the polymer strands may therefore be predicted by the system.

In one specific example, the system may be used to predict the strength of a material such as Kevlar by, e.g., predicting the strength of hydrogen bonds and pi-bond stacks. So, binding affinity prediction as disclosed herein may be used to facilitate the development of improved materials such as KEVLAR.

Simulation

Simulators often measure the binding affinity of a molecule to a protein, because the propensity of a molecule to stay in a region of the protein is correlates to its binding affinity there. An accurate description of the features governing binding could be used to identify regions and poses that have particularly high or low binding energy. The energetic description can be folded into Monte Carlo simulations to describe the motion of a molecule and the occupancy of the protein binding region. Similarly, stochastic simulators for studying and modeling systems biology could benefit from an accurate prediction of how small changes in molecule concentrations impact biological networks.

CONCLUSION

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A method for classification of a test object, method comprising:
   (A) obtaining a description of the test object;
   (B) for each respective target object in a first plurality of target objects, performing a first procedure comprising:
      (i) posing the description of the test object against the respective target object thereby obtaining a description of an interaction between the test object and the respective target object, and
      (ii) inputting the description of the interaction between the test object and the respective target object to a first classifier thereby obtaining a corresponding score for the interaction between the test object and the respective target object from the first classifier, wherein each corresponding score for the interaction between the test object and a respective target object across the first plurality of target objects forms a test vector for the test object; and (C) inputting the test vector for the test object to a second classifier thereby obtaining a transformation for the test vector as output from the second classifier, wherein the transformation provides an indication of a single target object in the first plurality of target objects.

2. The method of claim 1, wherein the second classifier is trained on a plurality of training vectors, each respective training vector in the plurality of training vectors is the output from the first classifier after inputting a corresponding training object in a first plurality of training objects as a test object in accordance with the first procedure, each training object in a first subset of the first plurality training objects is uniquely associated with a corresponding target object in the first plurality of target objects, and each training object in a second subset of the first plurality of training objects is associated with no target object in the first plurality of target objects.

3. The method of claim 1, wherein the posing the description of the test object against the respective target object thereby obtaining a description of an interaction between the test object and the respective target object is performed by a second procedure that comprises:

modeling the test object with the respective target object in each pose of a plurality of different poses, thereby creating a plurality of voxel maps, wherein each respective voxel map in the plurality of voxel maps comprises the test object in a respective pose in the plurality of different poses, and unfolding each voxel map in the plurality of voxel maps into a corresponding first classifier input vector, thereby creating a plurality of first classifier input vectors, wherein each first classifier input vector in the plurality of first classifier input vectors is the same size, and wherein the inputting the description of the interaction between the test object and the respective target object to a first classifier comprises:

inputting each respective first classifier input vector in the plurality of first classifier input vectors to the first classifier.

4. The method of claim 3, wherein the first classifier comprises a network architecture that includes (i) an input layer for sequentially receiving respective first classifier input vectors in the plurality of first classifier input vectors, (ii) a plurality of convolutional layers, and (iii) a scorer, wherein the plurality of convolutional layers includes an initial convolutional layer and a final convolutional layer, each layer in the plurality of convolutional layers is associated with a different set of weights, and responsive to the inputting of a respective first classifier input vector in the plurality of first classifier input vectors to the first classifier, the input layer feeds a first plurality of values into the initial convolutional layer as a first function of values in the respective first classifier input vector, each respective convolutional layer, other than the final convolutional layer, feeds intermediate values, as a respective second function of (i) the different set of weights associated with the respective convolutional layer and (ii) input values received by the respective convolutional layer, into another convolutional layer in the plurality of convolutional layers, and the final convolutional layer feeds final values, as a third function of (i) the different set of weights associated with the final convolutional layer and (ii) input values received by the final convolutional layer, into the scorer;

wherein the second procedure further comprises:

obtaining a plurality of scores from the scorer, wherein each score in the plurality of scores corresponds to the input of a first classifier input vector in the plurality of first classifier input vectors into the input layer, and using the plurality of scores to obtain the description of the interaction between the test object and the respective target object.

5. The method of claim 4, wherein the scorer comprises a plurality of fully-connected layers and an evaluation layer, and a fully-connected layer in the plurality of fully-connected layers feeds into the evaluation layer.

6. The method of claim 4, wherein the scorer comprises an implementation of a decision tree, a multiple additive regression tree, a clustering algorithm, principal component analysis, a nearest neighbor analysis, a linear discriminant analysis, a quadratic discriminant analysis, a support vector machine, an evolutionary method, a projection pursuit, a logistic regression, or ensembles thereof.

7. The method of claim 4, wherein a convolutional layer in the plurality of convolutional layers has a plurality of filters, and each filter in the plurality of filters convolves a cubic input space of $N^3$ with stride Y, wherein N is an integer of two or greater and Y is a positive integer.

8. The method of claim 7, wherein the different set of weights associated with the convolutional layer are associated with respective filters in the plurality of filters.

9. The method of claim 4, wherein the scorer comprises a plurality of fully-connected layers and a logistic regression cost layer, and a fully-connected layer in the plurality of fully-connected layers feeds into the logistic regression cost layer.

10. The method of claim 3, wherein each first classifier input vector in the plurality of first classifier input vectors is one-dimensional.

11. The method of claim 3, wherein the plurality of different poses comprises 2 or more poses, 10 or more poses, 100 or more poses, or 1000 or more poses.

12. The method of claim 3, wherein the plurality of different poses is obtained using a docking scoring function in one of a Markov chain Monte Carlo sampling, simulated annealing, a Lamarckian Genetic Algorithm, a genetic algorithm, or a deep convolutional neural net sampling.

13. The method of claim 3, wherein the plurality of different poses is obtained by incremental search using a greedy algorithm.

14. The method of claim 3, wherein the second procedure further comprises:

obtaining a plurality of scores from the first classifier, wherein each score in the plurality of scores corresponds to the input of a first classifier input vector in the plurality of first classifier input vectors into the first classifier, and using the plurality of scores to obtain the description of the interaction between the test object and the respective target object, and wherein the test object is a chemical compound, and the using the plurality of scores to obtain the description of the interaction between the test object and the respective target object comprises taking a measure of central tendency of the plurality of scores, wherein when the measure of central tendency satisfies a predetermined threshold value or predetermined threshold value range, the description of the interaction between the test object and the respective target object is deemed to have a first classification, and when the measure of central tendency fails to satisfy the predetermined threshold value or predetermined threshold value range, the description of the interaction between the test object and the respective target object is deemed to have a second classification.

15. The method of claim 14, wherein the first classification is a prediction that the test object binds to the respective target object with an $IC_{50}$, $EC_{50}$, Kd, KI, or percent inhibition that is below a first binding value, and the second classification is a prediction that the test object binds to the respective target object with an $IC_{50}$, $EC_{50}$, Kd, KI or percent inhibition that is above the first binding value.

16. The method of claim 15, wherein the first binding value is one micromolar.

17. The method of claim 15, wherein the first binding value is ten micromolar.

18. The method of claim 3, wherein
the second procedure further comprises:
obtaining a plurality of scores from the first classifier, wherein each score in the plurality of scores corresponds to the input of a first classifier input vector in the plurality of first classifier input vectors into the first classifier, and using the plurality of scores to obtain the description of the interaction between the test object and the respective target object, and wherein the using the plurality of scores to obtain the description of the interaction between the test object and the respective target object comprises taking a weighted average of the plurality of scores, wherein when the weighted average satisfies a predetermined threshold value or predetermined threshold value range, the test object is deemed to have a first classification, and when the weighted average fails to satisfy the predetermined threshold value or predetermined threshold value range, the test object is deemed to have a second classification.

19. The method of claim 18, wherein the weighted average is a Boltzman average of the plurality of scores.

20. The method of claim 18, wherein
the first classification is an $IC_{50}$, $EC_{50}$, Kd, KI, or percent inhibition for the test object with respect to the respective target object that is above a first binding value, and the second classification is an $IC_{50}$, $EC_{50}$, Kd, KI or percent inhibition for the test object with respect to the respective target object that is below the first binding value.

* * * * *